(12) United States Patent
Boral et al.

(10) Patent No.: US 8,455,535 B2
(45) Date of Patent: Jun. 4, 2013

(54) HETEROARYL DIHYDROINDOLONES AS KINASE INHIBITORS

(75) Inventors: Sougato Boral, Irvine, CA (US); Xialing Guo, San Clemente, CA (US); Shimiao Wang, Tustin, CA (US); Julie A. Wurster, Irvine, CA (US); Thomas C. Malone, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 13/150,543

(22) Filed: Jun. 1, 2011

(65) Prior Publication Data

US 2011/0257238 A1 Oct. 20, 2011

Related U.S. Application Data

(62) Division of application No. 11/687,408, filed on Mar. 16, 2007, now Pat. No. 7,977,351.

(60) Provisional application No. 60/784,827, filed on Mar. 22, 2006.

(51) Int. Cl.
*A61K 31/4015* (2006.01)
*C07D 209/34* (2006.01)

(52) U.S. Cl.
USPC .......................................... 514/414; 548/466

(58) Field of Classification Search
USPC ....................................................... 548/466
See application file for complete search history.

(56) References Cited

U.S. PATENT DOCUMENTS

| | | | |
|---|---|---|---|
| 4,966,849 A | 10/1990 | Vallee et al. |
| 5,217,999 A | 6/1993 | Levitzki et al. |
| 5,302,606 A | 4/1994 | Spada et al. |
| 5,330,992 A | 7/1994 | Eissenstat et al. |
| 5,792,783 A | 8/1998 | Tang et al. |
| 5,834,504 A | 11/1998 | Tang et al. |
| 5,883,113 A | 3/1999 | Tang et al. |
| 5,883,116 A | 3/1999 | Tang et al. |
| 5,886,020 A | 3/1999 | Tang et al. |
| 6,541,504 B1 | 4/2003 | Andrews et al. |
| 6,559,173 B1 | 5/2003 | Andrews et al. |
| 6,699,863 B1 | 3/2004 | Andrews et al. |
| 6,765,012 B2 | 7/2004 | Andrews et al. |
| 7,005,444 B2 | 2/2006 | Andrews et al. |
| 7,015,220 B2 | 3/2006 | Andrews et al. |

FOREIGN PATENT DOCUMENTS

| | | |
|---|---|---|
| WO | WO 91/15495 | 10/1991 |
| WO | WO 92/20642 | 11/1992 |
| WO | WO 92/21660 | 12/1992 |
| WO | WO 94/03427 | 2/1994 |
| WO | WO 94/10202 | 5/1994 |
| WO | WO 94/14808 | 7/1994 |
| WO | WO03-084951 | 10/2003 |
| WO | WO2004-050621 | 6/2004 |
| WO | WO2005-107708 | 11/2005 |

OTHER PUBLICATIONS

Kendall & Thomas, 1994, Proc. Nat'l Acad. Sci 90: 10705-09.
Jellinek, et al, Biochemistry 33, 1994: 10450-56.
Takano, et al, 1993, Mol. Bio. Cell 4:358A(2076).
Kinsella, et al, 1992, Exp. Cell Res. 199: 56-62.
Wright, et al, 1992, J. Cellular Phys. 152: 448-57.
Mariani, et al, 1994, Proc. Am. Assoc. Cancer Res. 35: 2268.
Kim, et al, 1993, Nature 362: 841-844.
Plowman et al, 1994, DN&P. 7(6): 334-339.
Bolen, 1993, Oncogen 8: 2025-2031.
Abstract-Database Registry-XP002451352-Oct. 20, 2004.
Abstract-Database Registry-XP002451353-Sep. 26, 2004.
Cancer[online], [retrieved on Jul. 6, 2007]. Retrieved from the internet. URL;http://en.wikipedia.orglwikiCancer.
Cancer[online], [retrieved on Jul. 6, 2007]. Retrieved from the internet. URL;http://www.nim.nih.gov/medlineplus/cancer.html>.
Science (1999), vol. 286, 531-537.
Cancer andMetastasis Reviews (1998), 17(1), 91-106.

*Primary Examiner* — Shawquia Young
(74) *Attorney, Agent, or Firm* — Krishna G. Banerjee

(57) ABSTRACT

The present invention provides a compound represented by the formula:

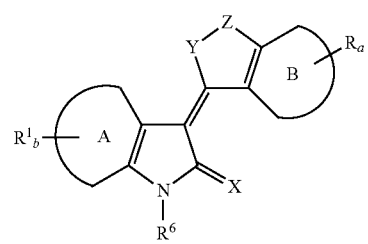

wherein ring systems A and B, and the variables $R^1$, b, $R^6$, Y, Z, X, R and a are defined in the specification. The compounds of the present invention may be used in a method for treating diseases related to unregulated tyrosine kinase signal transduction, such as cancer, blood vessel proliferative disorders, fibrotic disorders, mesangial cell proliferative disorders, and metabolic diseases.

21 Claims, No Drawings

HETEROARYL DIHYDROINDOLONES AS KINASE INHIBITORS

CROSS REFERENCE TO RELATED PATENT APPLICATIONS

This patent application is a divisional, and claims the benefit, of U.S. patent application Ser. No. 11/687,408, which was filed on Mar. 16, 2007 and U.S. Patent Application Ser. No. 60/784,827, which was filed on Mar. 22, 2006, in the names of Boral et al. and is hereby incorporated by reference in its entirety.

BACKGROUND OF THE INVENTION

1. Field of the Invention

The present invention relates to novel compounds capable of modulating, regulating and/or inhibiting tyrosine kinase signal transduction. The present invention is also directed to methods of regulating, modulating or inhibiting tyrosine kinases, whether of the receptor or non-receptor class, for the prevention and/or treatment of disorders related to unregulated tyrosine kinase signal transduction, including cell growth, metabolic, and blood vessel proliferative disorders.

2. Description of the Related Art

Protein tyrosine kinases (PTKs) comprise a large and diverse class of proteins having enzymatic activity. The PTKs play an important role in the control of cell growth and differentiation.

For example, receptor tyrosine kinase mediated signal transduction is initiated by extracellular interaction with a specific growth factor (ligand), followed by receptor dimerization, transient stimulation of the intrinsic protein tyrosine kinase activity and phosphorylation. Binding sites are thereby created for intracellular signal transduction molecules and lead to the formation of complexes with a spectrum of cytoplasmic signaling molecules that facilitate the appropriate cellular response (e.g., cell division, metabolic homeostasis, and responses to the extracellular microenvironment).

With respect to receptor tyrosine kinases, it has been shown also that tyrosine phosphorylation sites function as high-affinity binding sites for SH2 (src homology) domains of signaling molecules. Several intracellular substrate proteins that associate with receptor tyrosine kinases (RTKs) have been identified. They may be divided into two principal groups: (1) substrates which have a catalytic domain; and (2) substrates which lack such domain but serve as adapters and associate with catalytically active molecules. The specificity of the interactions between receptors or proteins and SH2 domains of their substrates is determined by the amino acid residues immediately surrounding the phosphorylated tyrosine residue. Differences in the binding affinities between SH2 domains and the amino acid sequences surrounding the phosphotyrosine residues on particular receptors are consistent with the observed differences in their substrate phosphorylation profiles. These observations suggest that the function of each receptor tyrosine kinase is determined not only by its pattern of expression and ligand availability but also by the array of downstream signal transduction pathways that are activated by a particular receptor. Thus, phosphorylation provides an important regulatory step which determines the selectivity of signaling pathways recruited by specific growth factor receptors, as well as differentiation factor receptors.

Aberrant expression or mutations in the PTKs have been shown to lead to either uncontrolled cell proliferation (e.g. malignant tumor growth) or to defects in key developmental processes. Consequently, the biomedical community has expended significant resources to discover the specific biological role of members of the PTK family, their function in differentiation processes, their involvement in tumorigenesis and in other diseases, the biochemical mechanisms underlying their signal transduction pathways activated upon ligand stimulation and the development of novel drugs.

Tyrosine kinases can be of the receptor-type (having extracellular, transmembrane and intracellular domains) or the non-receptor type (being wholly intracellular).

The RTKs comprise a large family of transmembrane receptors with diverse biological activities. The intrinsic function of RTKs is activated upon ligand binding, which results in phosphorylation of the receptor and multiple cellular substrates, and subsequently in a variety of cellular responses.

At present, at least nineteen (19) distinct RTK subfamilies have been identified. One RTK subfamily, designated the HER subfamily, is believed to be comprised of EGFR, HER2, HER3 and HER4. Ligands to the Her subfamily of receptors include epithelial growth factor (EGF), TGF-α, amphiregulin, HB-EGF, betacellulin and heregulin.

A second family of RTKs, designated the insulin subfamily, is comprised of the INS-R, the IGF-1R and the IR-R. A third family, the "PDGF" subfamily includes the PDGF α and β receptors, CSFIR, c-kit and FLK-II. Another subfamily of RTKs, identified as the FLK family, is believed to be comprised of the Kinase insert Domain-Receptor fetal liver kinase-1 (KDR/FLK-1), the fetal liver kinase 4 (FLK-4) and the fms-like tyrosine kinase 1 (flt-1). Each of these receptors was initially believed to be receptors for hematopoietic growth factors. Two other subfamilies of RTKs have been designated as the FGF receptor family (FGFR1, FGFR2, FGFR3 and FGFR4) and the Met subfamily (c-met and Ron).

Because of the similarities between the PDGF and FLK subfamilies, the two subfamilies are often considered together. The known RTK subfamilies are identified in Plowman et al, 1994, DN&P 7(6): 334-339, which is incorporated herein by reference.

The non-receptor tyrosine kinases represent a collection of cellular enzymes which lack extracellular and transmembrane sequences. At present, over twenty-four individual non-receptor tyrosine kinases, comprising eleven (11) subfamilies (Src, Frk, Btk, Csk, Abl, Zap70, Fes/Fps, Fak, Jak, Ack and LIMK) have been identified. At present, the Src subfamily of non-receptor tyrosine kinases is comprised of the largest number of PTKs and include Src, Yes, Fyn, Lyn, Lck, Blk, Hck, Fgr and Yrk. The Src subfamily of enzymes has been linked to oncogenesis. A more detailed discussion of non-receptor tyrosine kinases is provided in Bolen, 1993, Oncogen 8: 2025-2031, which is incorporated herein by reference.

Many of the tyrosine kinases, whether an RTK or non-receptor tyrosine kinase, have been found to be involved in cellular signaling pathways leading to cellular signal cascades leading to pathogenic conditions, including cancer, psoriasis and hyper immune response.

In view of the surmised importance of PTKs to the control, regulation and modulation of cell proliferation the diseases and disorders associated with abnormal cell proliferation, many attempts have been made to identify receptor and non-receptor tyrosine kinase "inhibitors" using a variety of approaches, including the use of mutant ligands (U.S. Pat. No. 4,966,849), soluble receptors and antibodies (PCT Application No. WO 94/10202; Kendall & Thomas, 1994, Proc. Nat'l Acad. Sci. 90: 10705-09; Kim, et al, 1993, Nature 362: 841-844), RNA ligands (Jellinek, et al, Biochemistry 33: 10450-56); Takano, et al, 1993, Mol. Bio. Cell 4:358A; Kinsella, et al, 1992, Exp. Cell Res. 199: 56-62; Wright, et al, 1992, J. Cellular Phys. 152: 448-57) and tyrosine kinase inhibitors (PCT Application Nos. WO 94/03427; WO 92/21660; WO 91/15495; WO 94/14808; U.S. Pat. No. 5,330, 992; Mariani, et al, 1994, Proc. Am. Assoc. Cancer Res. 35: 2268).

More recently, attempts have been made to identify small molecules which act as tyrosine kinase inhibitors. For example, bis monocyclic, bicyclic or heterocyclic aryl compounds (PCT Application No. WO 92/20642), vinylene-azaindole derivatives (PCT Application No. WO 94/14808) and 1-cyclopropyl-4-pyridyl-quinolones (U.S. Pat. No. 5,330,992) have been described generally as tyrosine kinase inhibitors. Styryl compounds (U.S. Pat. No. 5,217,999), styryl-substituted pyridyl compounds (U.S. Pat. No. 5,302, 606), certain quinazoline derivatives (EP Application No. 0 566 266 A1), seleoindoles and selenides (PCT Application No. WO 94/03427), tricyclic polyhydroxylic compounds (PCT Application No. WO 92/21660) and benzylphosphonic acid compounds (PCT Application No. WO 91/15495) have been described as compounds for use as tyrosine kinase inhibitors for use in the treatment of cancer.

The identification of effective small compounds which specifically inhibit signal transduction by modulating the activity of receptor and non-receptor tyrosine kinases to regulate and modulate abnormal or inappropriate cell proliferation is therefore desirable and one object of this invention.

Certain small compounds are disclosed in U.S. Pat. Nos. 5,792,783; 5,834,504; 5,883,113; 5,883,116 and 5,886,020 as useful for the treatment of diseases related to unregulated TKS transduction. These patents are hereby incorporated by reference in their entirety for the purpose of disclosing starting materials and methods for the preparation thereof, screens and assays to determine a claimed compound's ability to modulate, regulate and/or inhibit cell proliferation, indications which are treatable with said compounds, formulations and routes of administration, effective dosages, etc.

The following patents disclose and claim similar tyrosine kinase inhibitors: U.S. Pat. No. 6,541,504; U.S. Pat. No. 6,559,173; U.S. Pat. No. 7,005,444; U.S. Pat. No. 6,765,012; U.S. Pat. No. 6,699,863; and U.S. Pat. No. 7,015,220.

These patents are hereby incorporated by reference in their entirety.

BRIEF SUMMARY OF THE INVENTION

The present invention relates to organic molecules capable of modulating, regulating and/or inhibiting tyrosine kinase signal transduction. Such compounds are useful for the treatment of diseases related to unregulated TKS transduction, including cell proliferative diseases such as cancer, atherosclerosis, restenosis, metabolic diseases such as diabetes, inflammatory diseases such as psoriasis and chronic obstructive pulmonary disease, vascular proliferative disorders such as diabetic retinopathy, age-related macular degeneration and retinopathy of prematurity, autoimmune diseases and transplant rejection.

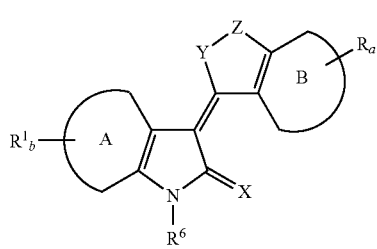

I

Wherein

X is O or S;

Y is O, S or NR$^3$;

Z is [C(R$^2$)$_2$]$_c$;

the ring system indicated by FIG. II represents a 5 or 6 membered aryl group

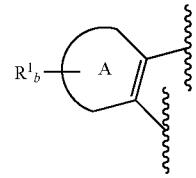

II and is preferably selected from the group consisting of

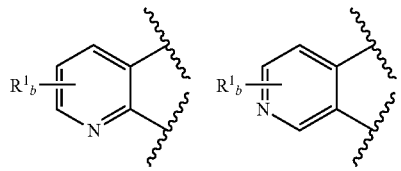

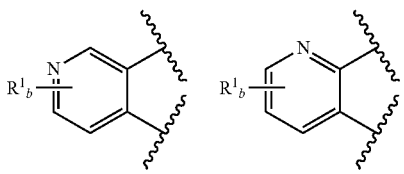

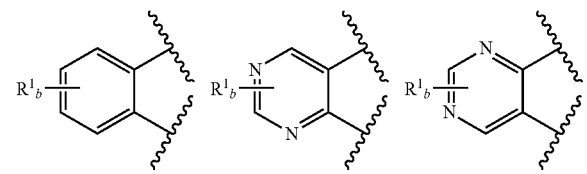

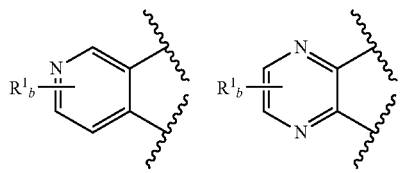

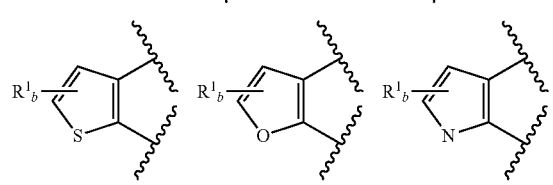

-continued
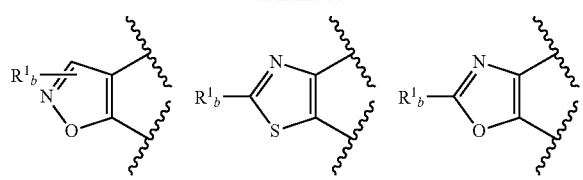
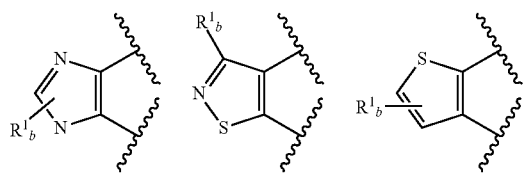
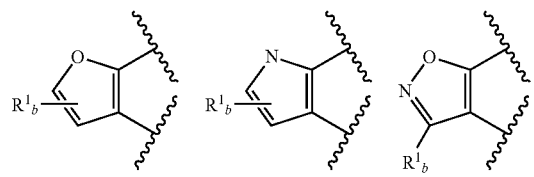
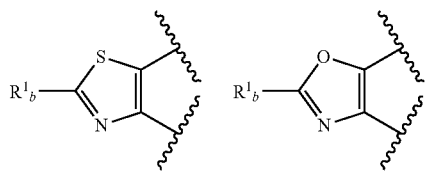
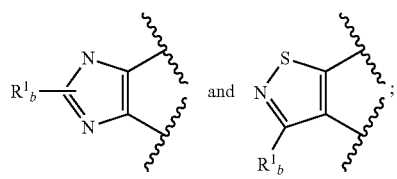
the ring system indicated by FIG. III represents a 5 or 6 membered aryl group
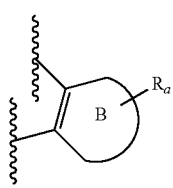
III
and is preferably selected from the group consisting of
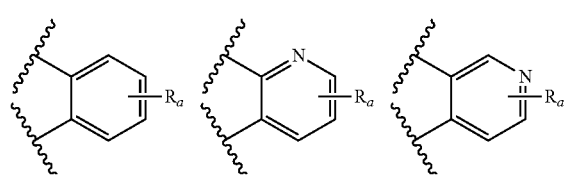
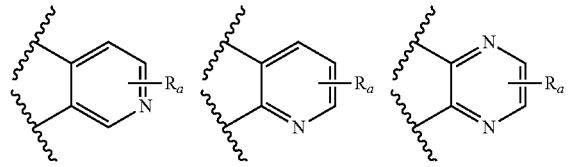
-continued
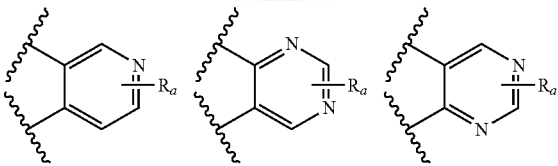
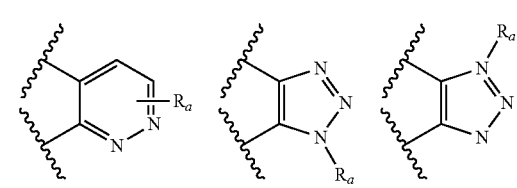
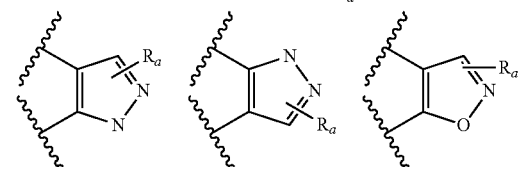
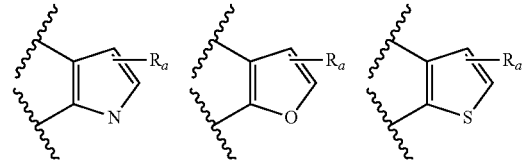
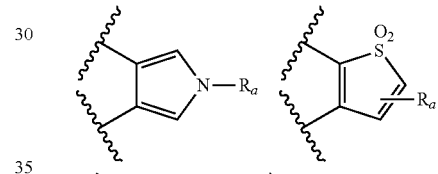
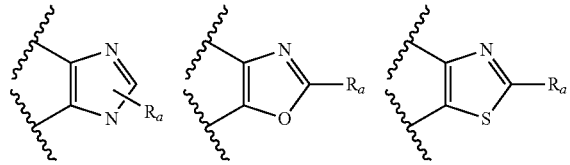
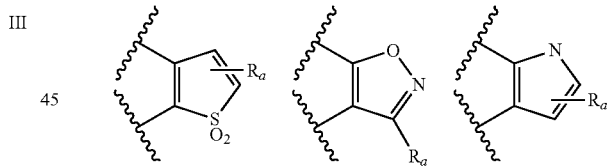
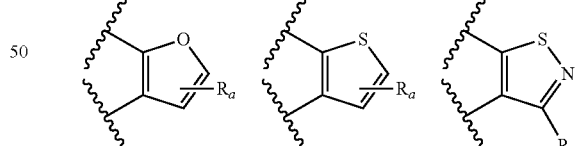
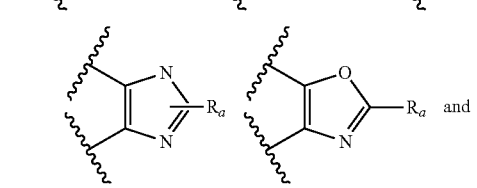
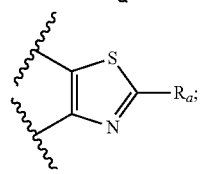

$R^1$ is selected from the group consisting of halogen, aryl, $C_1$ to $C_8$ alkyl, $CF_3$, $OCF_3$, $OCF_2H$, $S(O)_fR^2$, $(CR^3R^4)_dC(O)OR^2$, $O(CR^3R^4)_eC(O)OR^2$, $NR^2(CR^3R^4)_dC(O)R^2$, $NR^2(CR^3R^4)_dC(O)OR^2$, $OC(O)OR^2$, $OCH_2O$, $NR^2(CH_2)_eN(R^2)_2$, $O(CH_2)_eN(R^2)_2$, $(CR^3R^4)_dCN$, $O(CR^3R^4)_eCN$, $(CR^3R^4)_dAr$, $NR^2(CR^3R^4)_dAr$, $O(CR^3R^4)_dAr$, $S(O)_f(CR^3R^4)_dAr$, $(CR^3R^4)_dSO_2R^2$, $(CR^3R^4)_dC(O)N(R^2)_2$, $NR^2(CR^3R^4)_dC(O)N(R^2)_2$, $O(CR^3R^4)_dC(O)N(R^2)_2$, $S(O)_f(CR^3R^4)_eC(O)N(R^2)_2$, $(CR^3R^4)_dOR^2$, $NR^2(CR^3, R^4)_eOR^2$, $O(CR^3, R^4)_eOR^2$, $S(O)_f(CR^3, R^4)_eOR^2$, $C(O)(CR^3R^4)_dR^3$, $NR^2C(O)(CR^3R^4)_dR^3$, $OC(O)(CR^3R^4)_dN(R^2)_2$, $C(O)(CR^3R^4)_dN(R^2)_2$, $NR^2C(O)(CR^3R^4)_dN(R^2)_2$, $OC(O)(CR^3R^4)_dN(R^2)_2$, $(CR^3R^4)_dR^3$, $NR^2(CR^3R^4)_dR^3$, $O(CR^3R^4)_d R^3$, $S(O)_f(CR^3R^4)_dR^3$, $(CR^3R^4)_dN(R^2)_2$, $NR^2(CR^3R^4)_eN(R^2)_2$, $O(CR^3R^4)_eN(R^2)_2$, $S(O)_f(CR^3R^4)_dN(R^2)_2$, $N(R^5)_2$, $OR^5$, $C(O)R^5$, $S(O)_fR^5$, $C(O)ArNR^2C(O)Ar$, $NR^2ArNR^2C(O)Ar$, $OArNR^2C(O)Ar$, $SArNR^2C(O)Ar$, $C(O)ArC(O)(NR^2)_2$, $OArC(O)(NR^2)_2$, $NR^2ArC(O)(NR^2)_2$, $SArC(O)(NR^2)_2C(O)ArC(O)NR^2Ar$, $OArC(O)NR^2Ar$, $NR^2ArC(O)NR^2Ar$ and $SArC(O)NR^2Ar$;

$R^2$ is selected from the group consisting of hydrogen, $C_1$ to $C_8$ alkyl, $C_1$ to $C_8$ alkenyl, $C_1$ to $C_8$ alkynyl, $C_1$ to $C_4$ alkylol, lower alkylphenyl, phenyl, $(CR^3R^4)_dAr$, $OC(O)R^7$, $(CR^3R^4)_dC(O)OR^7$, $(CR^3R^4)_dSO_2R^7$, $(CR^3R^4)_dSO_2N(R^7)_2$, $(CR^3, R^4)_dOR^7$, $(CR^3R^4)_dOSO_2R^7$, $(CR^3R^4)_dP(O)(OR^7)_2$, $(CR^3R^4)_dR^7$, $(CR^3R^4)_eN(R^7)_2$ and $(CR^3R^4)_eNR^7C(O)N(R^7)_2$, wherein $N(R^2)_2$ and $N(R^7)_2$ may form a 3-7 membered heterocyclic ring and $[C(R^2)_2]_c$ may form a 3-7 membered carbocyclic or heterocyclic ring, for example pyrrolidine, 3-fluoropyrrolidine, piperidine, 4-fluoropiperidine, N-methylpiperazine, morpholine, 2,6-dimethylmorpholine, thiomorpholine, etc. and said heterocyclic ring may be substituted with one or more of $R^3$;

R is selected from the group consisting of halogen, $C_1$ to $C_8$ alkyl, $CF_3$, $OCF_3$, $OCF_2H$, $(CR^3R^4)_dCN$, $NR^2(CR^3R^4)_eCN$, $O(CR^3R^4)_eCN$, $S(O)_fR^2$, $(CR^3R^4)_dC(O)OR^2$, $(CR^3R^4)_dC(O)R^2$, $(CR^3R^4)_dC(OR^2)_2$, $NR^2(CR^3R^4)_dC(O)OR^2$, $O(CR^3R^4)_dC(O)OR^2$, $S(O)_f(CR^3R^4)_dC(O)OR^2$, $(CR^3R^4)_dAr$, $NR^2(CR^3R^4)_dAr$, $O(CR^3R^4)_dAr$, $S(O)_f(CR^3R^4)_dAr$, $(CR^3R^4)_dSO_2R^2$, $NR^2(CR^3R^4)_dS(O)_fR^2$, $O(CR^3R^4)_d S(O)_fR^2$, $S(O)_f(CR^3R^4)_eS(O)_fR^2$, $(CR^3R^4)_dC(O)N(R^2)_2$, $NR^2(CR^3R^4)_dC(O)N(R^2)_2$, $O(CR^3R^4)_dC(O)N(R^2)_2$, $S(O)_f(CR^3R^4)_eC(O)N(R^2)_2$, $(CR^3, R^4)_dOR^2$, $NR^2(CR^3, R^4)_eOR^2$, $O(CR^3, R^4)_eOR^2$, $S(O)_f(CR^3, R^4)_eOSO_2R^2$, $NR^2(CR^3, R^4)_eOSO_2R^2$, $O(CR^3, R^4)_eOSO_2R^2$, $S(O)_f(CR^3, R^4)_eOSO_2R^2$, $(CR^3, R^4)_dP(O)(OR^2)_2$, $NR^2(CR^3, R^4)_dP(O)(OR^2)_2$, $O(CR^3R^4)_dP(O)(OR^2)_2$, $S(O)_f(CR^3, R^4)_eP(O)(OR^2)_2$, $C(O)(CR^3R^4)_dR^3$, $NR^2C(O)(CR^3R^4)_dR^3$, $OC(O)(CR^3R^4)_dN(R^2)_2$, $C(O)(CR^3R^4)_dN(R^2)_2$, $C(O)NR^2(CR^3R^4)_eN(R^2)_2$, $NR^2C(O)(CR^3R^4)_dN(R^2)_2$, $OC(O)(CR^3R^4)_dN(R^2)_2$, $(CR^3R^4)_dR^3$, $NR^2(CR^3R^4)_dR^3$, $O(CR^3R^4)_dR^3$, $S(O)_f(CR^3, R^4)_dR^3$, $HNC(O)R^2$, $HN-C(O)OR^2$, $(CR^3R^4)_dN(R^2)_2$, $NR^2(CR^3R^4)_eN(R^2)_2$, $O(CR^3R^4)_eN(R^2)_2$, $S(O)_f(CR^3R^4)_dN(R^2)_2$, $OP(O)(OR^2)_2$, $OC(O)OR^2$, $OCH_2O$, $HN-CH=CH$, $-N(COR^2)CH_2CH_2$, $HC=N-NH$, $N=CH-S$, $(CR^3R^4)_dC=C(CR^3R^4)_dR^2$, $(CR^3R^4)_dC=C(CR^3R^4)_dOR^2$, $(CR^3R^4)_dC=C(CR^3R^4)_dN(R^2)_2$, $(CR^3R^4)_dCC(CR^3R^4)_dR^2$, $(CR^3R^4)_dCC(CR^3R^4)_eOR^2$, $(CR^3R^4)_dCC(CR^3R^4)_eN(R^2)_2$, $(CR^3R^4)_dC(O)(CR^3R^4)_eR^2$, $(CR^3R^4)_dC(O)(CR^3R^4)_dOR^2$ and $(CR^3R^4)_dC(O)(CR^3R^4)_dN(R^2)_2$ and $(CR^3R^4)_dR^5$;

$R^3$ and $R^4$ may be selected from the group consisting of H, F, hydroxy, $C_1$-$C_4$ alkyl, $(CR^8R^9)_dOR^8$, $(CR^8R^9)_dO(CR^8R^9)_eOR^8$, $(CR^8R^9)_dCOOR^8$ and $(CR^8R^9)_dN(R^8)_2$ or $CR^3R^4$ may represent a carbocyclic or heterocyclic ring of from 3 to 6 carbons or, alternatively, $(CR^3R^4)_d$ and $(CR^3R^4)_e$ may form a 3-7 membered carbocyclic or heterocyclic ring;

$R^5$ is an aryl group or a substituted oxindole;

$R^6$ is selected from the group consisting of hydrogen, $C_1$-$C_8$ alkyl, hydroxymethyl and phenyl;

$R^7$ is selected from the group consisting of hydrogen, hydroxyl, F, $C_1$ to $C_8$ alkyl, $C_1$ to $C_8$ alkenyl, $C_1$ to $C_8$ alkynyl, $C_1$ to $C_4$ alkylol, lower alkylphenyl, phenyl, $R^8$ and $R^9$ are selected from the group consisting of hydrogen, hydroxyl, F, $C_2$ to $C_8$ alkyl, $C_2$ to $C_8$ alkenyl, $C_1$ to $C_8$ alkynyl, $C_1$ to $C_4$ alkylol, lower alkylphenyl and phenyl;

a is 0 or an integer of from 1 to 3;
b is 0 or an integer of from 1 to 2;
c is an integer of from 1 to 2;
d is 0 or an integer of from 1 to 5;
e is an integer of from 1 to 4; and
f is 0 or an integer of from 1 to 2, and further provided any of said alkyl or aryl radicals may be substituted with one or two halo, hydroxy, lower alkyloxy or lower alkyl amino radicals, including cycloalkylamino radicals and wherein the alkyl, or the cycloalkyl amino ring, may include an enchained oxygen, sulfur or additional nitrogen atom and may be substituted with one or two halo or lower alkyl radicals;

and pharmaceutically acceptable salts thereof.

DETAILED DESCRIPTION OF THE INVENTION

Illustrative routes to compounds of the present invention are illustrated in Schemes 1-13 set forth below and are not intended to limit the scope of the invention.

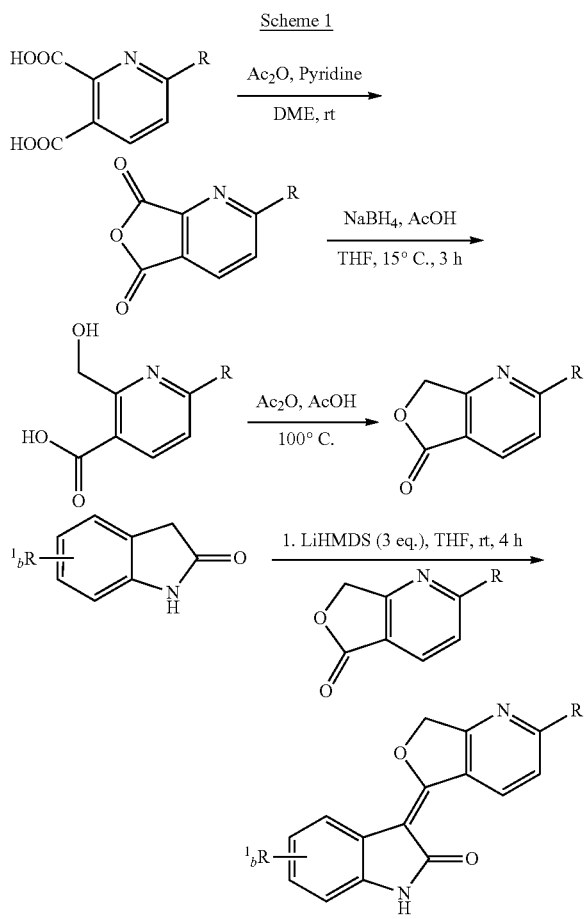

Scheme 1

Scheme 2
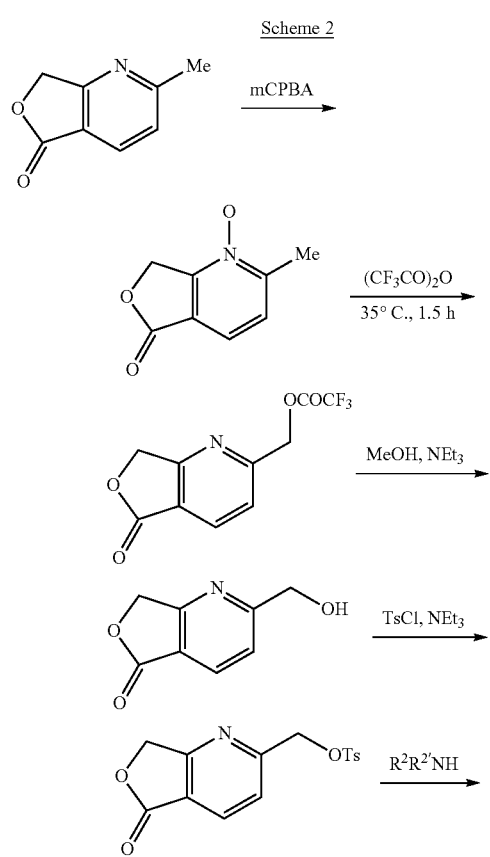
Scheme 3
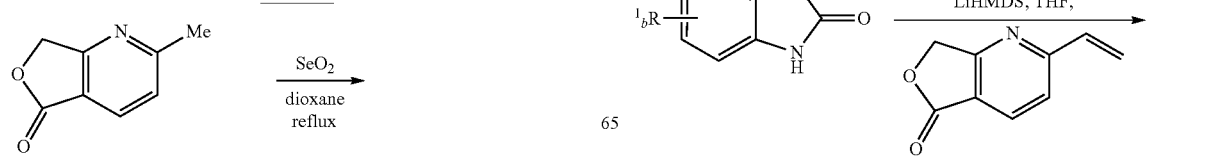
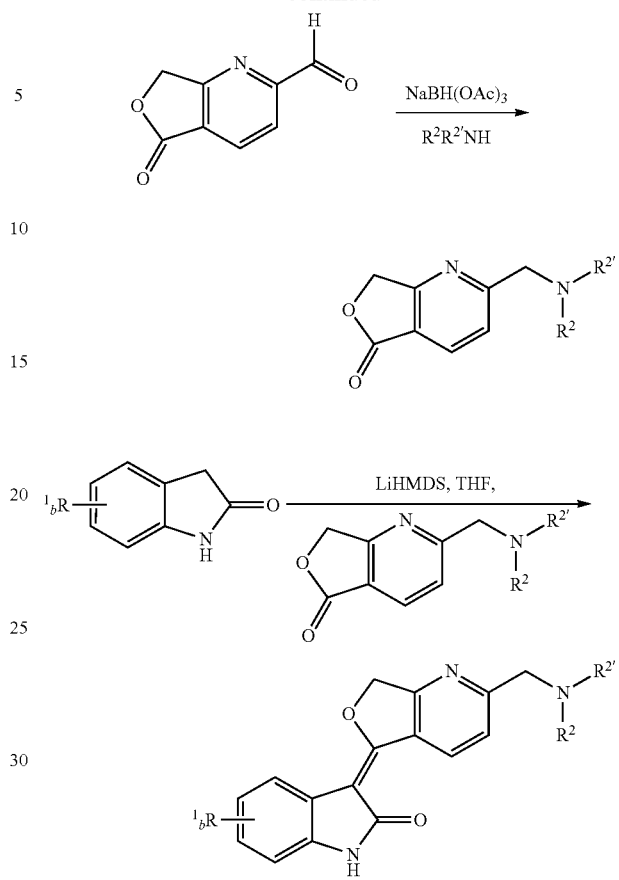
Scheme 4
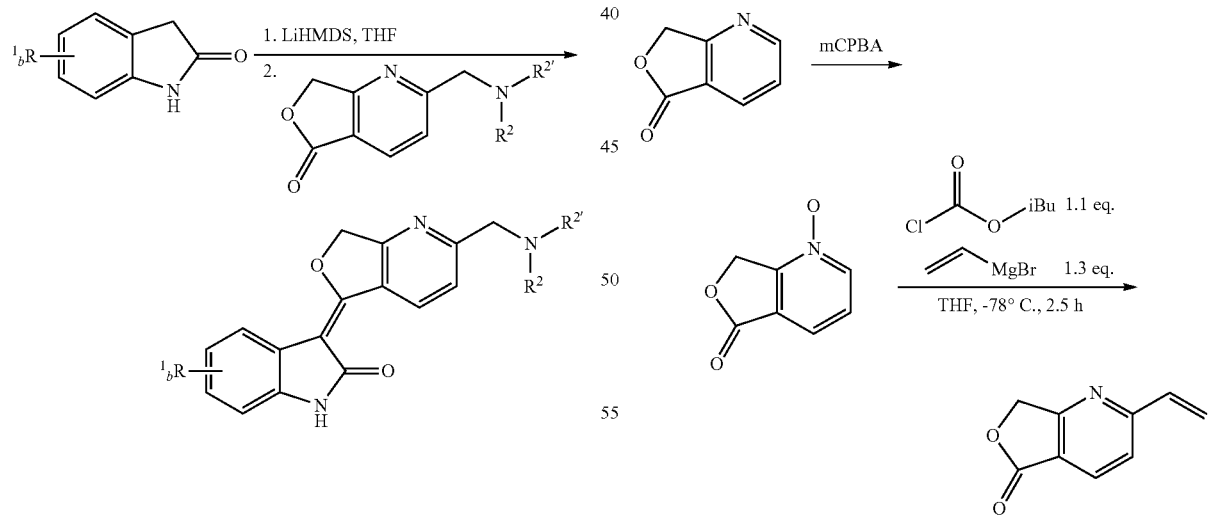

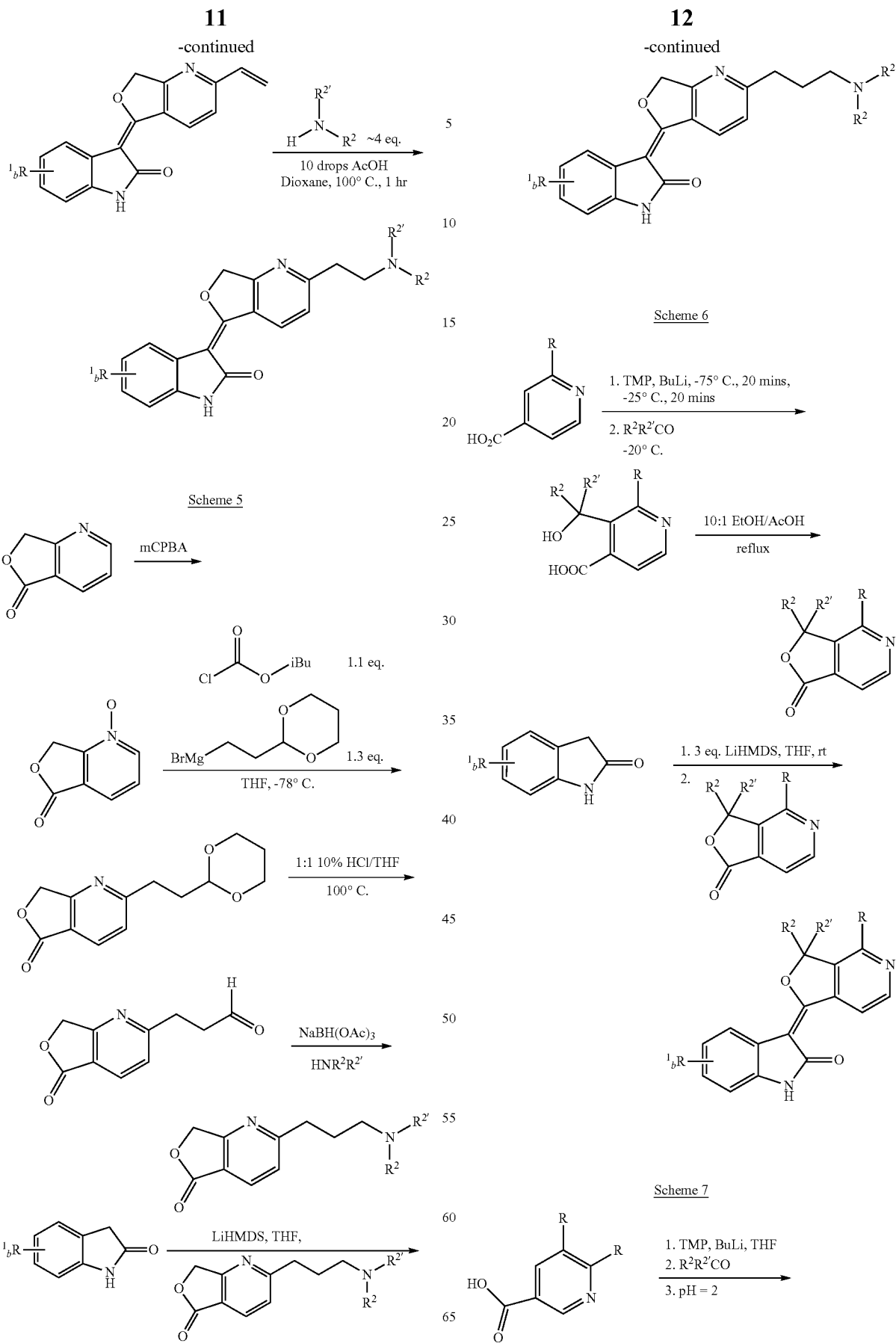

-continued
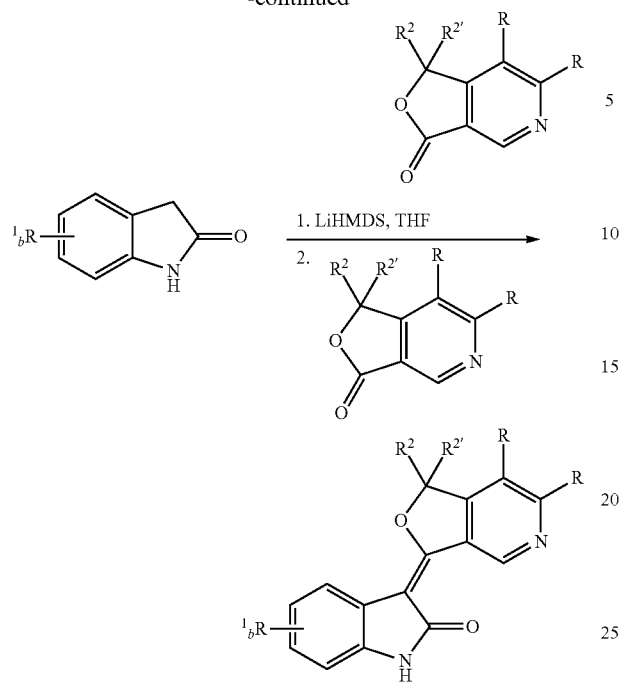
Scheme 8
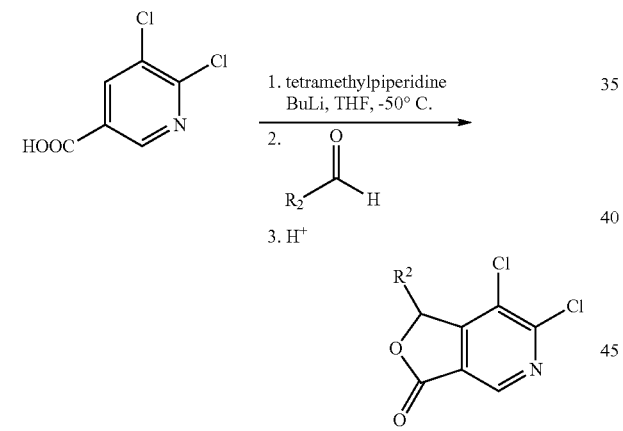
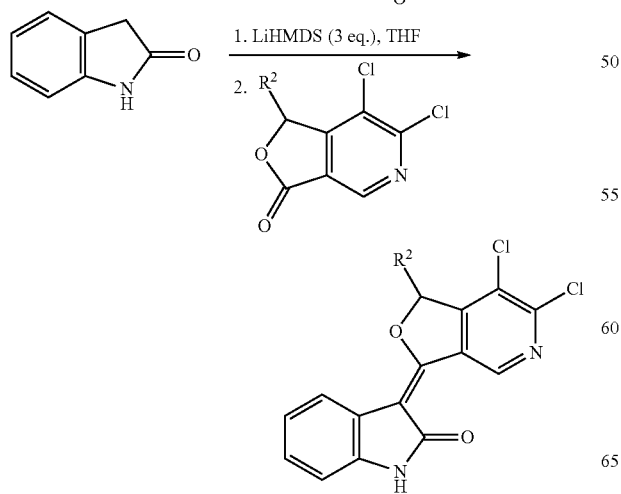
-continued
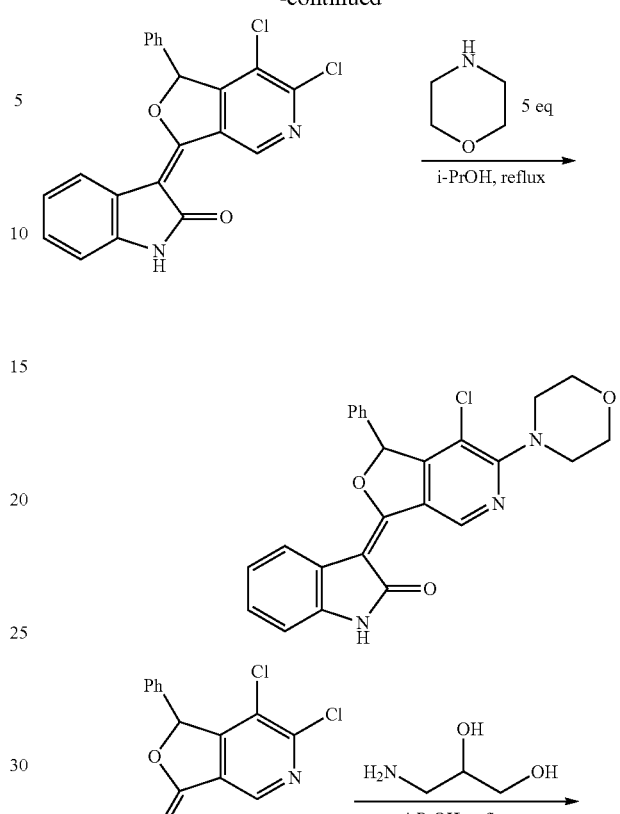
Scheme 9
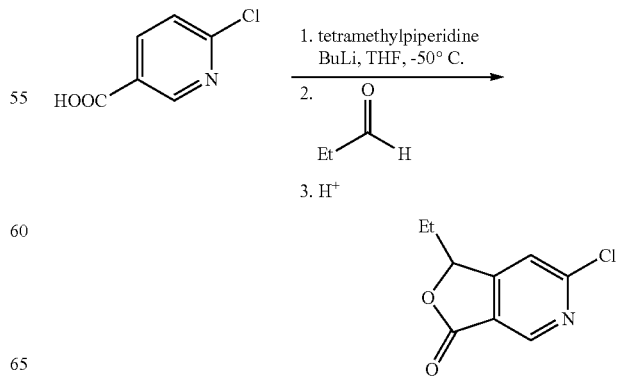

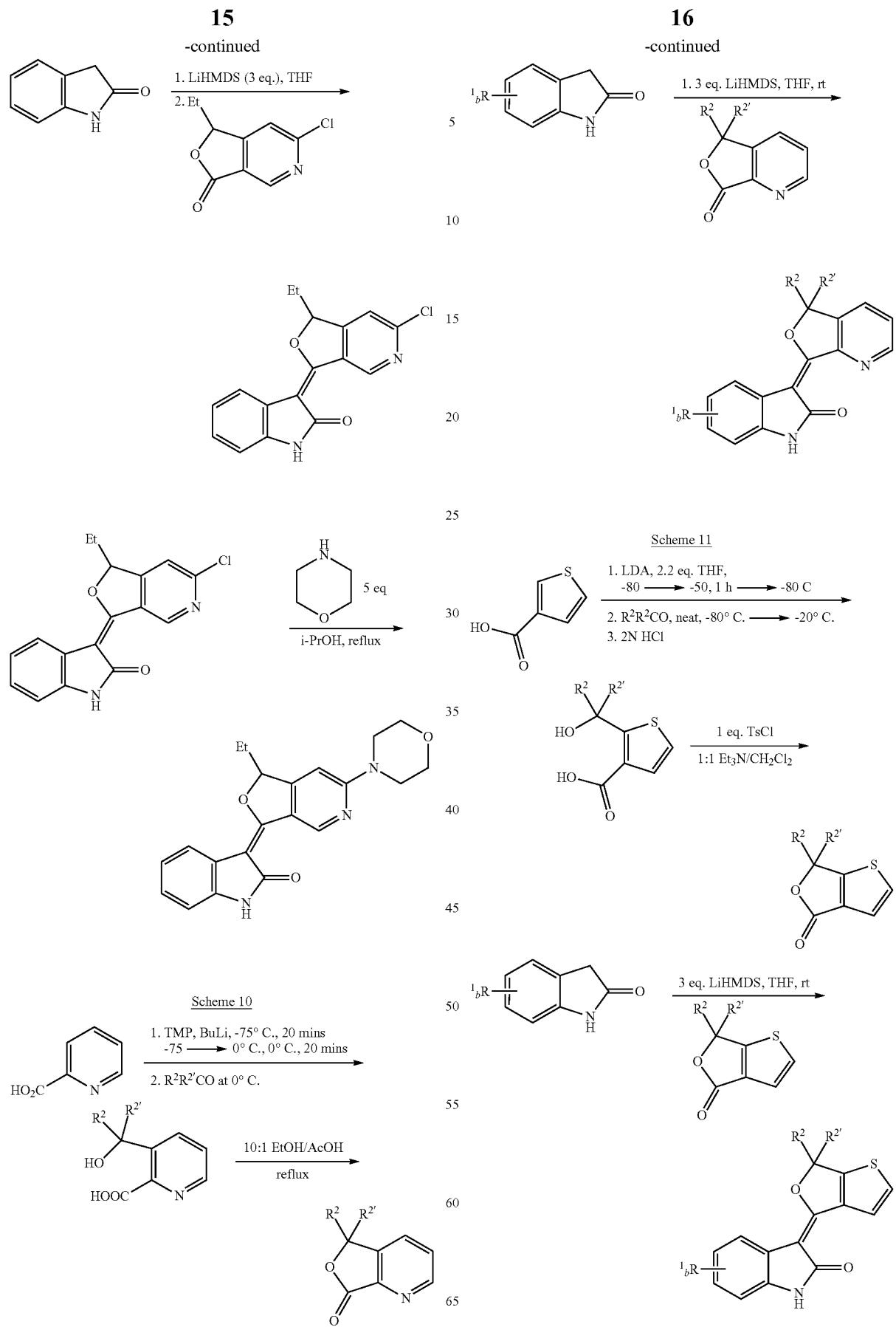

Scheme 12

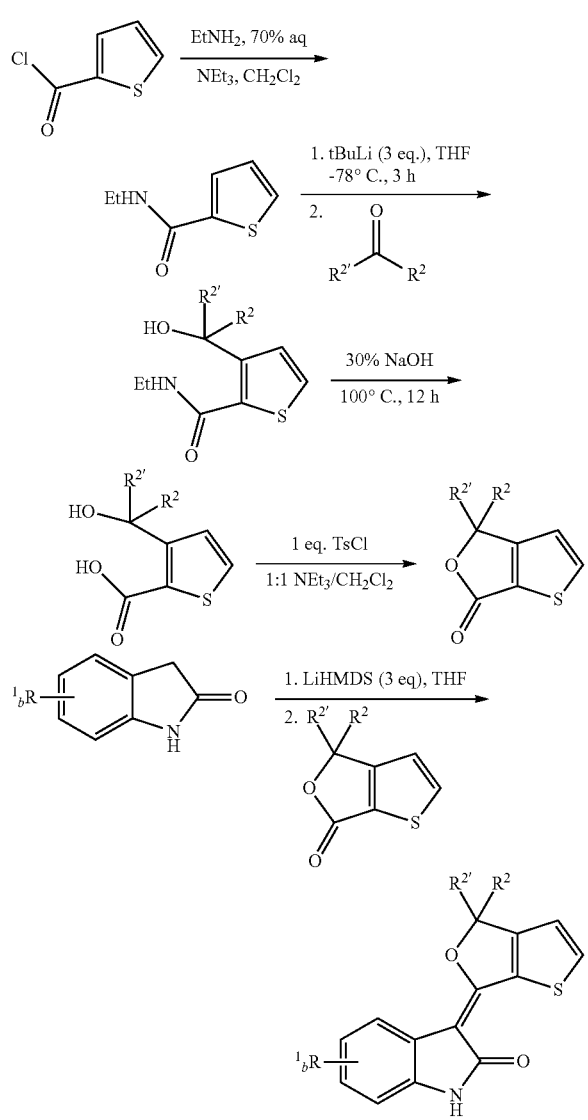

Scheme 13

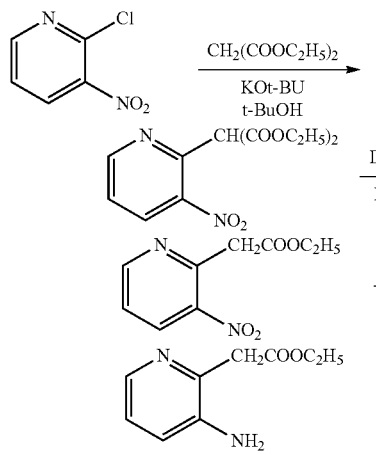

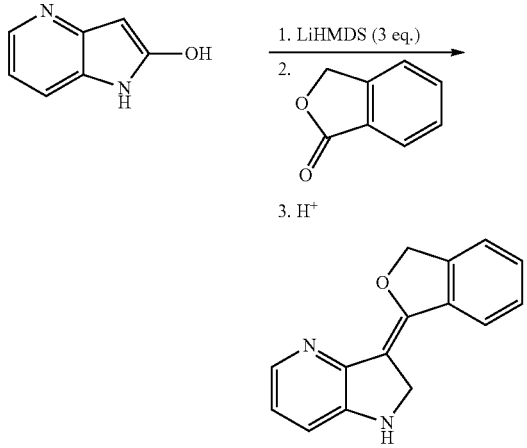

In particular, the compounds of the present invention are selected from the compounds of Table 1, below wherein said compounds are represented by formula IV:

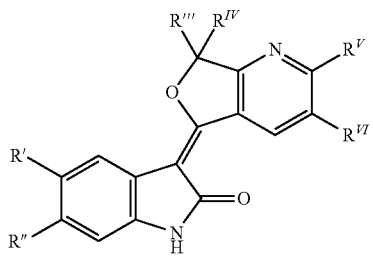

wherein X is O, Y is O, Z is $[C(R^2)_2]$, R' and R" are $R^1$, R''' and $R^{IV}$ are $R^2$ and $R^V$ and $R^{VI}$ are R.

TABLE 1

| Example Number | R' | R" | R''' | $R^{IV}$ | $R^V$ | $R^{VI}$ |
|---|---|---|---|---|---|---|
| 1 | F | H | H | H | H | H |
| 2 | F | H | H | H | CH$_3$ | H |
| 3 | H | H | H | H | CH$_3$ | H |
| 4 | F | H | H | H | ⸺CH$_2$⸺N(morpholine) | H |
| 5 | F | H | H | H | COOH | H |
| 6 | F | H | H | H | ⸺CH$_2$⸺N(CH$_2$CH$_3$)$_2$ | H |
| 7 | F | H | H | H | ⸺CH$_2$CH$_2$N(CH$_3$)CH$_2$CH$_2$N(CH$_2$CH$_3$)$_2$ | H |

TABLE 1-continued
| Example Number | R' | R" | R''' | R$^{IV}$ | R$^V$ | R$^{VI}$ |
|---|---|---|---|---|---|---|
| 8 | F | H | H | H | 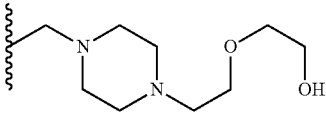 [SMILES: *CN1CCN(CCOCCO)CC1] | H |
| 9 | F | H | H | H | 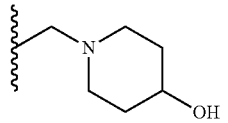 [SMILES: *CN1CCC(O)CC1] | H |
| 10 | F | H | H | H | 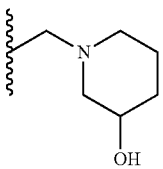 [SMILES: *CN1CCCC(O)C1] | H |
| 11 | F | H | H | H | 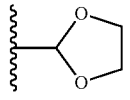 | H |
| 12 | F | H | H | H | 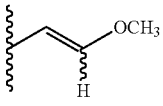 | H |
| 13 | F | H | H | H | 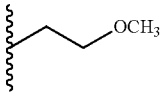 | H |
| 14 | F | H | H | H | 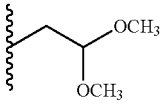 | H |
| 15 | F | H | H | H | 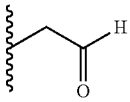 [SMILES: *CC=O] | H |
| 16 | F | H | H | H |  | H |
| 17 | F | H | H | H | 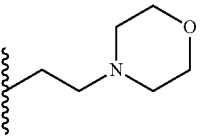 [SMILES: *CCN1CCOCC1] | H |
| 18 | F | H | H | H | 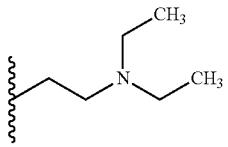 [SMILES: *CCN(CC)CC] | H |
| 19 | F | H | H | H | 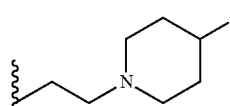 | H |
| 20 | F | H | H | H | 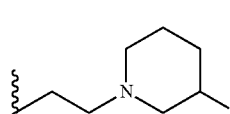 | H |
| 21 | F | H | H | H | 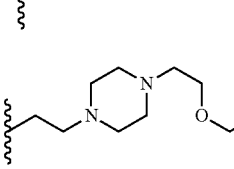 | H |
| 22 | F | H | H | H | 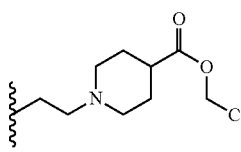 | H |
| 23 | F | H | H | H | 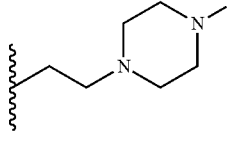 | H |
| 24 | F | H | H | H | 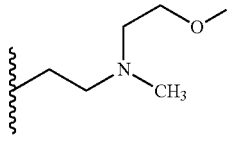 | H |
| 25 | F | H | H | H | 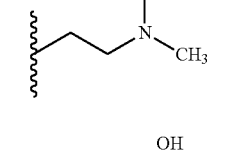 | H |
| 26 | F | H | H | H | 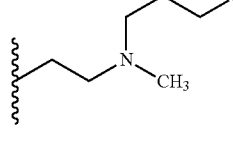 | H |
| 27 | F | H | H | H | 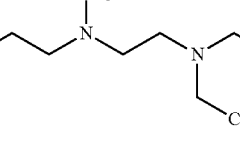 | H |

TABLE 1-continued

| Example Number | R' | R" | R"' | R$^{IV}$ | R$^V$ | R$^{VI}$ |
|---|---|---|---|---|---|---|
| 28 | F | H | H | H | 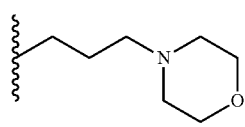 [SMILES: *CCCN1CCOCC1] | H |
| 29 | F | H | H | H | 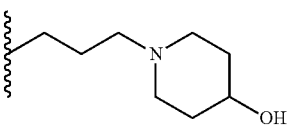 [SMILES: *CCCN1CCC(O)CC1] | H |
| 30 | F | H | H | H | 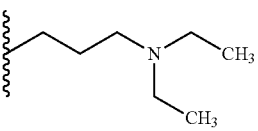 | H |
| 31 | F | H | H | H | 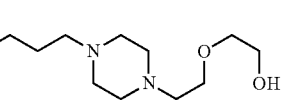 | H |
| 32 | F | H | H | H | 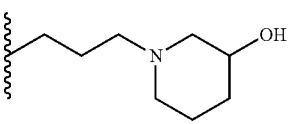 [SMILES: *CCCN1CCCC(O)C1] | H |
| 33 | F | H | H | H | 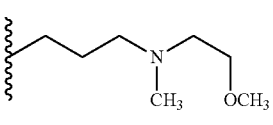 [SMILES: *CCCN(C)CCOC] | H |
| 34 | F | H | H | H | 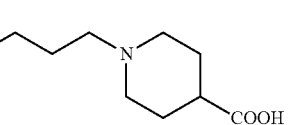 | H |
| 35 | F | H | H | H | 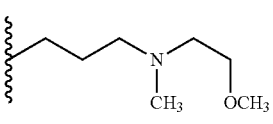 | H |
| 36 | F | H | H | H | 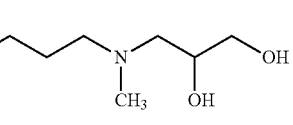 | H |
| 37 | F | H | H | H | 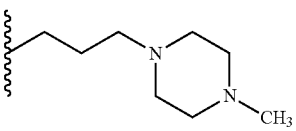 [SMILES: *CCCN1CCN(C)CC1] | H |
| 38 | F | H | H | H | | H |

TABLE 1-continued

| Example Number | R' | R" | R"' | R$^{IV}$ | R$^V$ | R$^{VI}$ |
|---|---|---|---|---|---|---|
| 39 | F | H | H | H |  | H |
| 40 | F | H | H | H | 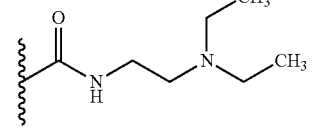 | H |

TABLE 2

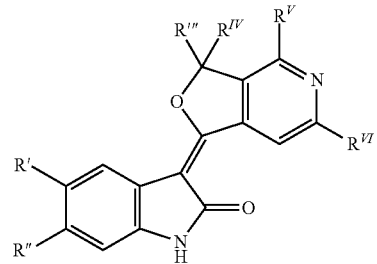

| Example Number | R' | R" | R"' | R$^{IV}$ | R$^V$ | R$^{VI}$ |
|---|---|---|---|---|---|---|
| 41 | F | H | H | CH$_2$CH$_3$ | H | H |
| 42 | F | H | H | H | Cl | H |
| 43 | F | H | H | H | H | H |

TABLE 3

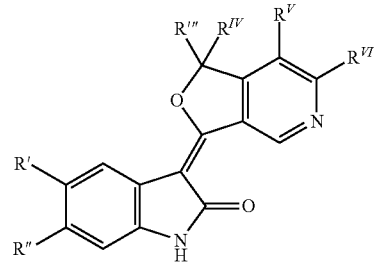

| Example Number | R' | R" | R"' | R$^{IV}$ | R$^V$ | R$^{VI}$ |
|---|---|---|---|---|---|---|
| 44 | H | H | H | CH$_2$CH$_3$ | H | Cl |
| 45 | H | H | H | Ph | Br | H |
| 46 | H | H | H | Ph | Cl | Cl |
| 47 | H | H | H | CH$_2$CH$_3$ | Cl | Cl |
| 48 | H | H | H | Ph | Cl | 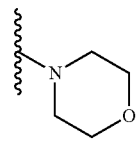 [SMILES: *N1CCOCC1] |

TABLE 3-continued
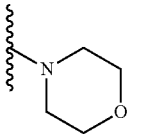 [SMILES: *N1CCOCC1]
| Example Number | R' | R" | R'" | $R^{IV}$ | $R^V$ | $R^{VI}$ |
|---|---|---|---|---|---|---|
| 49 | H | H | H | $CH_2CH_3$ | H | 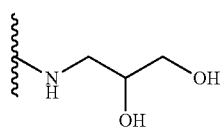 |
| 50 | H | H | H | Ph | Cl | 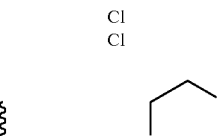 |
| 51 | F | H | H | $CH_2CH_3$ | Cl | Cl |
| 52 | F | H | H | H | Cl | Cl |
| 53 | F | H | H | $CH_2CH_3$ | Cl | 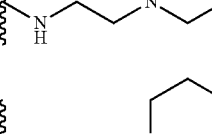 |
| 54 | F | H | H | $CH_2CH_2CH_3$ | Cl | 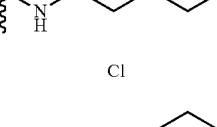 |
| 55 | F | H | H | $CH_2CH_2CH_3$ | Cl | Cl |
| 56 | H | H | H | $CH_2CH_3$ | H | 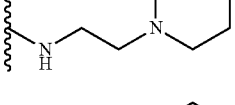 |
| 57 | F | H | H | $CH_2CH_3$ | H | 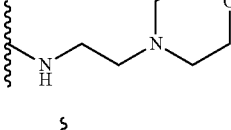 |
| 58 | F | H | H | H | Cl | 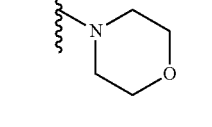 |
| 59 | F | H | H | H | Cl | 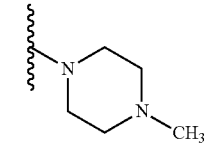 [SMILES: *N1CCN(C)CC1] |
| 60 | F | H | H | $CH_2CH_3$ | Cl | H |
| 61 | F | H | H | H | Cl |  |
| 62 | F | H | H | H | Cl |  |
| 63 | F | H | H | H | Cl | 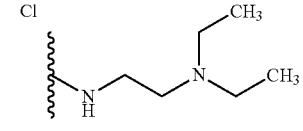 |
| 64 | F | H | H | H | Cl | 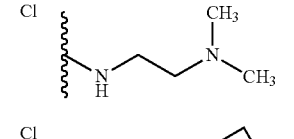 |
| 65 | F | H | H | $CH_2CH_3$ | H | $CF_3$ |
| 66 | F | H | H | $CH_2CH_3$ | H | H |
TABLE 4
| Example Number | Structure |
|---|---|
| 67 | 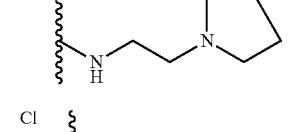 |
| 68 | 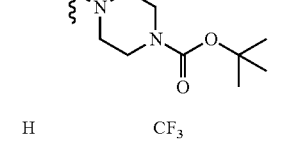 |

TABLE 4-continued

| Example Number | Structure |
|---|---|
| 69 | (structure) |
| 70 | (structure) |
| 71 | (structure) |
| 73 | (structure) |
| 74 | (structure) |

The present invention is further directed to pharmaceutical compositions comprising a pharmaceutically effective amount of the above-described compounds and a pharmaceutically acceptable carrier or excipient. Such a composition is believed to modulate signal transduction by a tyrosine kinase, either by inhibition of catalytic activity, affinity to ATP or ability to interact with a substrate.

More particularly, the compositions of the present invention may be included in methods for treating diseases comprising proliferation, fibrotic or metabolic disorders, for example cancer, fibrosis, psoriasis, atherosclerosis, arthritis, and other disorders related to abnormal vasculogenesis and/or angiogenesis, such as diabetic retinopathy.

The following defined terms are used throughout this specification:

"Ac" refers to acetyl.
"Ar" refers to aryl.
"THF" refers to tetrahydrofurane.
"Bu" refers to butyl
"DMSO" refers to dimethylsulfoxide
"Me" refers to methyl.
"Et" refers to ethyl.
"tBu" refers to t-butyl.
"iPr" refers to iso-propyl.
"Pr" refers to propyl
"Ph" refers to phenyl.

"Pharmaceutically acceptable salt" refers to those salts which retain the biological effectiveness and properties of the free bases and which are obtained by reaction with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like. Certain "pharmaceutically acceptable salts" are the salts of free acid, e.g. the sodium salt of a carboxylic acid.

"Alkyl" refers to a straight-chain, branched or cyclic saturated aliphatic hydrocarbon. Preferably, the alkyl group has 1 to 12 carbons. More preferably, it is a lower alkyl of from 1 to 8 carbons, most preferably 1 to 4 carbons. Typical alkyl groups include methyl, ethyl, propyl, isopropyl, butyl, isobutyl, tertiary butyl, pentyl, hexyl and the like. The alkyl group may be optionally substituted with one or more substituents are selected from the group consisting of hydroxyl, cyano, alkoxy, =O, =S, $NO_2$, halogen, dimethyl amino, and SH.

"Alkenyl" refers to a straight-chain, branched or cyclic unsaturated hydrocarbon group containing at least one carbon-carbon double bond. Preferably, the alkenyl group has 1 to 12 carbons. More preferably it is a lower alkenyl of from 1 to 8 carbons, most preferably 1 to 4 carbons. The alkenyl group may be optionally substituted with one or more substituents selected from the group consisting of hydroxyl, cyano, alkoxy, =O, =S, $NO_2$, halogen, dimethyl amino, and SH.

"Alkynyl" refers to a straight-chain, branched or cyclic unsaturated hydrocarbon containing at least one carbon-carbon triple bond. Preferably, the alkynyl group has 1 to 12 carbons. More preferably it is a lower alkynyl of from 1 to 8 carbons, most preferably 1 to 4 carbons. The alkynyl group may be optionally substituted with one or more substituents selected from the group consisting of hydroxyl, cyano, alkoxy, =O, =S, $NO_2$, halogen, dimethyl amino, and SH.

"Alkoxyl" refers to an "O-alkyl" group.

"Aryl" refers to an aromatic group which has at least one ring having a conjugated pi electron system and includes carbocyclic aryl, heterocyclic aryl and biaryl groups. The aryl group may be optionally substituted with one or more substituents selected from the group consisting of halogen, trihalomethyl, hydroxyl, SH, OH, $NO_2$, amine, thioether, cyano, alkoxy, alkyl, and amino.

"Alkaryl" refers to an alkyl that is covalently joined to an aryl group. Preferably, the alkyl is a lower alkyl.

"Carbocyclic aryl" refers to an aryl group wherein the ring atoms are carbon.

"Heterocyclic aryl" refers to an aryl group having from 1 to 4 heteroatoms as ring atoms, the remainder of the ring atoms being carbon. Heteroatoms include oxygen, sulfur, and nitrogen. Thus, heterocyclic aryl groups include furanyl, thienyl, pyridyl, pyrrolyl, N-lower alkyl pyrrolo, pyrimidyl, pyrazinyl, imidazolyl, tetrazoyl and the like.

"Hydrocarbyl" refers to a hydrocarbon radical having only carbon and hydrogen atoms. Preferably, the hydrocarbyl radical has from 1 to 20 carbon atoms, more preferably from 1 to 12 carbon atoms and most preferably from 1 to 8 carbon atoms.

"Substituted hydrocarbyl" refers to a hydrocarbyl radical wherein one or more, but not all, of the hydrogen and/or the carbon atoms are replaced by a halogen, nitrogen, oxygen, sulfur or phosphorus atom or a radical including a halogen, nitrogen, oxygen, sulfur or phosphorus atom, e.g. fluoro, chloro, cyano, nitro, hydroxyl, phosphate, thiol, etc.

"Amide" refers to —C(O)—NH—R' or —NH—C(O)R', wherein R' is alkyl, aryl, alkylaryl or hydrogen.

"Thioamide" refers to —C(S)—NH—R' or —NH—C(S)R', wherein R' is alkyl, aryl, alkylaryl or hydrogen.

"Amine" refers to a —N(R")R'" group, wherein R" and R'" are independently selected from the group consisting of alkyl, aryl, and alkylaryl.

"Thioether" refers to —S—R", wherein R" is alkyl, aryl, or alkylaryl.

"Sulfonyl" refers to —S(O)$_2$—R"", where R"" is aryl, C(CN)=C-aryl, CH$_2$CN, alkyaryl, sulfonamide, NH-alkyl, NH-alkylaryl, or NH-aryl.

"LiHMDS" refers to lithium hexamethyldisilizane.

"MTBE" refers to methyl tertiary butyl ether.

The present invention relates to compounds capable of regulating and/or modulating tyrosine kinase signal transduction and more particularly receptor and non-receptor tyrosine kinase signal transduction.

Receptor tyrosine kinase mediated signal transduction is initiated by extracellular interaction with a specific growth factor (ligand), followed by receptor dimerization, transient stimulation of the intrinsic protein tyrosine kinase activity and phosphorylation. Binding sites are thereby created for intracellular signal transduction molecules and lead to the formation of complexes with a spectrum of cytoplasmic signaling molecules that facilitate the appropriate cellular response (e.g., cell division, metabolic effects and responses to the extracellular microenvironment).

It has been shown that tyrosine phosphorylation sites in growth factor receptors function as high-affinity binding sites for SH2 (src homology) domains of signaling molecules. Several intracellular substrate proteins that associate with receptor tyrosine kinases have been identified. They may be divided into two principal groups: (1) substrates which have a catalytic domain; and (2) substrates which lack such domain but serve as adapters and associate with catalytically active molecules. The specificity of the interactions between receptors and SH2 domains of their substrates is determined by the amino acid residues immediately surrounding the phosphorylated tyrosine residue. Differences in the binding affinities between SH2 domains and the amino acid sequences surrounding the phosphotyrosine residues on particular receptors are consistent with the observed differences in their substrate phosphorylation profiles. These observations suggest that the function of each receptor tyrosine kinase is determined not only by its pattern of expression and ligand availability but also by the array of downstream signal transduction pathways that are activated by a particular receptor. Thus, phosphorylation provides an important regulatory step which determines the selectivity of signaling pathways recruited by specific growth factor receptors, as well as differentiation factor receptors.

Tyrosine kinase signal transduction results in, among other responses, cell proliferation, differentiation and metabolism. Abnormal cell proliferation may result in a wide array of disorders and diseases, including the development of neoplasia such as carcinoma, sarcoma, leukemia, glioblastoma, hemangioma, psoriasis, arteriosclerosis, arthritis and diabetic retinopathy (or other disorders related to uncontrolled angiogenesis and/or vasculogenesis, e.g. macular degeneration).

This invention is therefore directed to compounds which regulate, modulate and/or inhibit tyrosine kinase signal transduction by affecting the enzymatic activity of the RTKs and/or the non-receptor tyrosine kinases and interfering with the signal transduced by such proteins. More particularly, the present invention is directed to compounds which regulate, modulate and/or inhibit the RTK and/or non-receptor tyrosine kinase mediated signal transduction pathways as a therapeutic approach to cure many kinds of solid tumors, including but not limited to carcinoma, sarcoma, leukemia, erythroblastoma, glioblastoma, meningioma, astrocytoma, melanoma and myoblastoma. Indications may include, but are not limited to brain cancers, bladder cancers, ovarian cancers, gastric cancers, pancreas cancers, colon cancers, blood cancers, lung cancers and bone cancers.

The invention is further illustrated by the following examples which are illustrative of a specific mode of practicing the invention and are not intended as limiting the scope of the claims.

Preparation 1

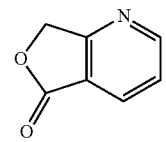

7H-Furo[3,4-b]pyridin-5-one

A solution of furo[3,4-b]pyridine-5,7-dione (3.0 g, 20 mmol) in THF (20 mL) is treated with sodium borohydride (0.75 g, 20 mmol). The reaction mixture is placed under an argon atmosphere and the temperature is maintained at 15° C. with a water bath. Acetic acid (2.4 g, 39 mmol) is added dropwise at 15° C. The reaction mixture is stirred for 4 h and is then concentrated on a rotary evaporator. The crude residue is then treated with acetic acid (8 mL) and acetic anhydride (8.0 mL) and heated at 100° C. overnight. The reaction mixture is cooled and concentrated. The residue is purified by chromatography (silica gel, gradient elution 30% EtOAc/hexane to 50% EtOAc/hexane). The product containing fractions are concentrated to give the title compound as a white solid (360 mg, 27%).

Example 1

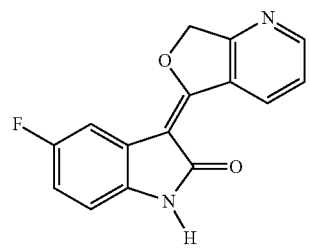 [SMILES: O=C1Nc2ccc(F)cc2/C1=C1\OCc2ncccc21]

5-Fluoro-3-(7H-furo[3,4-b]pyridin-5-ylidene)-1,3-dihydro-indol-2-one

A solution of 5-fluoro-1,3-dihydro-indol-2-one (453 mg, 3.0 mmol.) in THF (3 mL) is placed under an Argon atmosphere and cooled in an ice bath. A solution of lithium bis(trimethylsilyl)amide (6.0 mL of a 1M in THF, 6.0 mmol, 3 eq.) is added slowly at 0° C. and the resulting solution is stirred for 10 min. The ice-bath is removed and a solution of 7H-furo[3,4-b]pyridin-5-one (270 mg, 2.0 mmol) in THF (6 mL) is added dropwise to the reaction mixture. The resulting solution is stirred at room temperature for 4 h and poured into a 10% aqueous HCl solution (50 mL). After 10 min at room temperature, the reaction is heated to ~90° C. for 45 min. and then let stir at room temperature for 36 h. The solid which forms is collected by filtration and washed sequentially with MeOH, EtOAc, Et$_2$O (3×5 mL) and dried under vacuum to give the title compound (200 mg, 37%).

Preparation 2

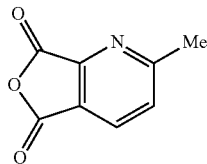 [SMILES: Cc1ccc2c(n1)C(=O)OC2=O]

2-Methyl-furo[3,4-b]pyridine-5,7-dione

A solution of 6-methyl-1,2-pyridine dicarboxylic acid (25 g, 138 mmol) and acetic acid (42 mL, 733 mmol) in DME (150 mL) is treated with pyridine (22 mL, 272 mmol) and stirred at room temperature for 2 h. The pale yellow solution is diluted with ether (250 mL) and then hexane (1250 mL) is added slowly. A white precipitate is formed. The solution is cooled to 0° C. for 30 min and the white solid is collected by filtration. The solid is washed with hexane and dried to give the title compound as a white solid (16.7 g, 74%).

Preparation 3

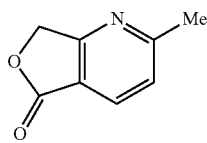 [SMILES: Cc1ccc2c(n1)COC2=O]

2-Methyl-7H-furo[3,4-b]pyridin-5-one

A suspension of 2-methyl-furo[3,4-b]pyridine-5,7-dione (15 g, 92 mmol) in THF (100 mL) is treated with sodium borohydride (3.75 g, 99 mmol) at 15° C. under an argon atmosphere. The reaction mixture is then treated dropwise with acetic acid (12 g, 200 mmol) at 15° C. During this addition gas evolution is observed. The reaction mixture is stirred at 15° C. for 4 h and is then concentrated. The residue is treated with acetic acid (40 mL) and acetic anhydride (40 mL). The resulting solution is stirred at 100° C. for 3 h. The brown solution is cooled to room temperature and concentrated. The residue is treated with a 20% aqueous NaCl solution and extracted with chloroform. The organic extract is washed with saturated aqueous NaCl solution, dried over Na$_2$SO$_4$ and concentrated. The residue is purified by chromatography (silica gel, gradient elution, 5:1 hexane/ethyl acetate to 2:1 hexane/ethyl acetate). The product containing fractions are concentrated to give the title compound as a white solid (9.03 g, 44%)

Example 2

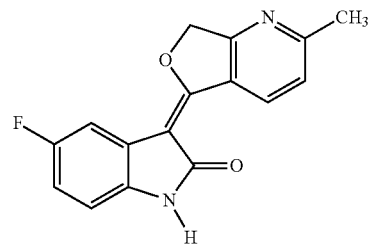 [SMILES: Cc1ccc2c(n1)CO/C2=C1/C(=O)Nc2ccc(F)cc21]

5-Fluoro-3-(2-methyl-7H-furo[3,4-b]pyridin-5-ylidene)-1,3-dihydro-indol-2-one

A solution of 5-fluoro-1,3-dihydro-indol-2-one (752 mg, 4.98 mmol.) in THF (5 mL) is placed under an argon atmosphere and cooled in an ice bath. A solution of Li bis(trimethylsilyl)amide (13.2 mL of a 1M in THF, 13.2 mmol) is added slowly at 0° C. and the resulting solution is stirred at 0° C. for 10 min. The ice-bath is removed and a solution of 2-methyl-7H-furo[3,4-b]pyridin-5-one (495 mg, 3.32 mmol) in THF (6 mL) is added dropwise to the reaction mixture. The resulting solution is stirred for 4.5 h and then poured into 50 mL of aqueous 10% HCl solution. After 10 min at room temperature, the reaction is heated to ~90° C. for 45 min and is then stirred at room temperature for 36 h. The solid which precipitated from solution is collected by filtration and washed sequentially with small volumes of MeOH (3×5 mL), EtOAc (3×5 mL) and Et$_2$O (3×5 mL) followed by drying to give the title compound as a yellow solid (450 mg, 48%).

Example 3

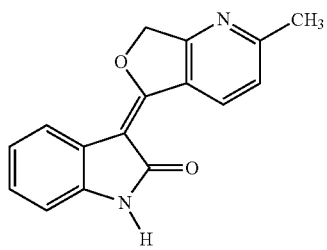 [SMILES: Cc1ccc2c(n1)CO/C2=C1/C(=O)Nc2ccccc21]

3-(2-Methyl-7H-furo[3,4-b]pyridin-5-ylidene)-1,3-dihydro-indol-2-one

A solution of 1,3-dihydro-indol-2-one (200 mg, 1.5 mmol.) in THF (2 mL) is placed under an argon atmosphere and cooled in an ice bath. A solution of Li bis(trimethylsilyl) amide (4.0 mL of a 1M solution in THF, 4.0 mmol) is added slowly at 0° C. and the resulting solution is stirred for 10 min. The ice-bath is then removed and a solution of 2-methyl-7H-furo[3,4-b]pyridin-5-one (150 mg, 1.00 mmol) in THF (6 mL) is added dropwise to the reaction mixture. The resulting solution is stirred for 4 h and then poured into 10% aqueous HCl solution (50 mL). After 10 min at room temperature, the reaction is heated to ~90° C. for 45 min followed by stirring at room temperature for 36 h. The solid which precipitated from solution is collected by filtration and washed sequentially with small volumes of MeOH, EtOAc, Et₂O and dried under vacuum to give the title compound as a yellow solid (78 mg, 30%).

Preparation 4

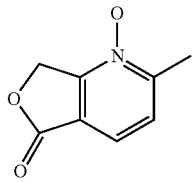

2-Methyl-7H-furo[3,4-b]pyridin-5-one N-oxide

A solution of 2-methyl-7H-furo[3,4-b]pyridin-5-one (150 mg, 1.0 mmol) in chloroform (5 mL) and dichloromethane (1 mL) is treated with m-chloroperoxybenzoic acid (258 mg, 1.5 mmol). The reaction mixture is stirred at room temperature overnight. The reaction mixture is concentrated and the residue is purified by chromatography (silica gel). The product containing fractions are concentrated to give the title compound as a solid (122 mg, 73%).

Preparation 5

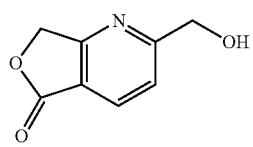 [SMILES: O=C1OCc2nc(CO)ccc21]

2-Hydroxymethyl-7H-furo[3,4-b]pyridin-5-one

A solution of 2-methyl-7H-furo[3,4-b]pyridin-5-one N-oxide (122 mg, 0.74 mmol) in dichloromethane (2 mL) is heated at reflux. Trifluoroacetic anhydride (1.5 mL, 10 mmol) is added dropwise and heating is continued for approximately 30 min. The reaction mixture is cooled and concentrated. The residue is treated with methanol (3 mL) and triethylamine (2 mL) and stirred until no starting material remained. The reaction mixture is concentrated and the residue is purified by chromatography (silica gel). The product containing fractions are concentrated to give the title compound (70 mg, 42%).

Example 4

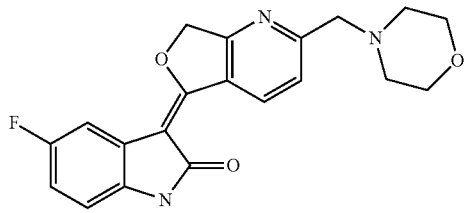 [SMILES: O=C1Nc2ccc(F)cc2/C1=C1\OCc2nc(CN3CCOCC3)ccc21]

5-Fluoro-3-(2-morpholin-4-ylmethyl-7H-furo[3,4-b] pyridin-5-ylidene)-1,3-dihydro-indol-2-one A solution of 5-fluoro-1,3-dihydro-indol-2-one (113 mg, 0.75 mmol.) in THF (1 mL) is placed under an argon atmosphere cooled in an ice bath. A solution of lithium bis(trimethylsilyl)amide (2 mL of a 1M solution in THF, 2 mmol) is added slowly at 0° C. and the resulting solution is stirred for 10 min. The ice-bath is removed and a solution of 2-morpholin-4-ylmethyl-7H-furo[3,4-b]pyridin-5-one (120 mg, 0.5 mmol) in THF (2 mL) is added dropwise to the reaction mixture. The resulting solution is stirred for 4 h and then poured into a 10% aqueous HCl solution. The resulting solution is stirred for 48 h at room temperature. The solid which precipitated from solution is collected by filtration and washed sequentially with small volumes of MeOH, EtOAc, Et₂O (3×5 mL). The residual solid is purified by chromatography (silica gel, 5% MeOH in EtOAc). The product containing fractions are concentrated to give the title compound as a yellow solid (65 mg, 35%).

Preparation 6 and Preparation 7

5-Oxo-5,7-dihydro-furo[3,4-b]pyridine-2-carboxaldehyde

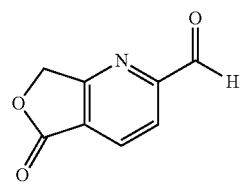 [SMILES: O=Cc1ccc2c(n1)COC2=O]

and
5-Oxo-5,7-dihydro-furo[3,4-b]pyridine-2-carboxylic acid and

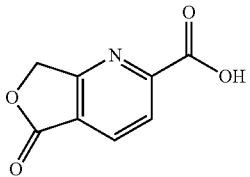 [SMILES: O=C(O)c1ccc2c(n1)COC2=O]

A solution of 2-methyl-7H-furo[3,4-b]pyridin-5-one (1.41 g, 9.46 mmol) in dioxane (50 mL) is treated with selenium dioxide (1.2 g, 10.8 mmol) and the reaction mixture is heated at 100° C. for 3 h. Additional selenium dioxide (1.2 g, 10.8 mmol) is added at 3 and 6 hours and the reaction mixture is heated at 100° C. The reaction is heated at 100° C. for an additional 42 h. The reaction mixture is filtered through celite and washed with dioxane. The filtrate is concentrated under reduced pressure and subject to chromatography (silica gel, EtOAc/hexane). The high $R_f$ product containing fractions are concentrated to give 5-Oxo-5,7-dihydro-furo[3,4-b]pyridine-2-carbaldehyde (1.23 g, 80%). The low Rf containing fractions are concentrated to give 5-oxo-5,7-dihydro-furo[3,4-b]pyridine-2-carboxylic acid (159 mg, 9%).

Example 5

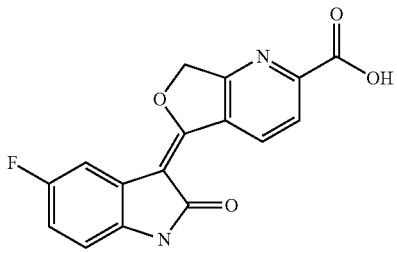 [SMILES: O=C1Nc2ccc(F)cc2/C1=C1\OCc2nc(C(=O)O)ccc21]

5-(5-Fluoro-2-oxo-1,2-dihydro-indol-3-ylidene)-5,7-dihydro-furo[3,4-b]pyridine-2-carboxylic acid A solution of 5-fluoro-1,3-dihydro-indol-2-one (177 mg, 1.17 mmol) in THF (2 mL) is treated with a solution of lithium bis(trimethylsilyl)amide (2.9 mL of a 1M solution in THF, 2.3 mmol) dropwise. The resulting solution is stirred at room temperature for 15 min. A solution 5-oxo-5,7-dihydro-furo[3,4-b]pyridine-2-carboxylic acid (105 mg, 0.59 mmol) in dimethylformamide (2 mL) is added dropwise to the reaction mixture. The resulting solution is stirred for 3 h and is then poured into a cold 10% aqueous HCl solution (30 mL). The reaction mixture is stirred at room temperature for 65 h. The solid which precipitated from solution is collected by filtration, washed with water and purified by chromatography (silica gel, MeOH/EtOAc). The product containing fractions are concentrated to give the title compound as a reddish solid (54 mg, 29%).

Preparation 8

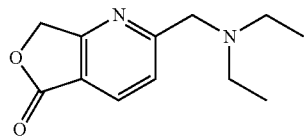 [SMILES: CCN(CC)Cc1ccc2c(n1)COC2=O]

2-Diethylaminomethyl-7H-furo[3,4-b]pyridin-5-one

A solution of 5-oxo-5,7-dihydro-furo[3,4-b]pyridine-2-carbaldehyde (110 mg, 0.68 mmol) in dichloroethane (4 mL) is treated with diethylamine (75 µL, 0.68 mmol) followed by the addition of sodium triacetoxyborohydride (200 mg, 0.94 mmol). The reaction mixture is stirred at room temperature for 1.5 h. and then treated with saturated aqueous NaHCO$_3$ solution. The aqueous layer is extracted twice with EtOAc (2×). The combined organic extracts are dried, and concentrated. The residue is chromatographed (silica gel, EtOAc/hexane). The product containing fractions are concentrated to give the title compound as white solid (90 mg, 61%).

Example 6

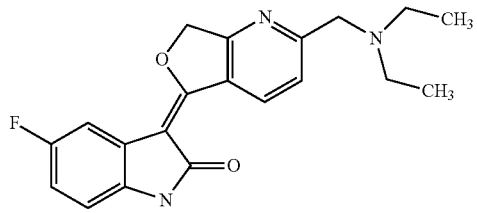 [SMILES: CCN(CC)Cc1ccc2c(n1)CO/C2=C1/C(=O)Nc2ccc(F)cc21]

3-(2-Diethylaminomethyl-7H-furo[3,4-b]pyridin-5-ylidene)-5-fluoro-1,3-dihydro-indol-2-one A solution of 5-fluoro-1,3-dihydro-indol-2-one (88 mg, 0.58 mmol.) in THF (4 mL) is placed under an argon atmosphere cooled in an ice bath. A solution of lithium bis(trimethylsilyl)amide (1.55 mL of a 1M solution in THF, 1.55 mmol) is added slowly at 0° C. and the resulting solution is stirred for 20 min. The ice-bath is then removed and a solution of 2-diethylaminomethyl-7H-furo[3,4-b]pyridin-5-one (85 mg, 0.39 mmol) in THF (1 mL) is added dropwise to the reaction mixture. The resulting solution is stirred for 3 h and then poured into 10% aqueous HCl solution (20 mL) and stirred for 48 h at room temperature. The solid which precipitated from solution is collected by filtration. The solid is purified by chromatography (silica gel, gradient elution, 100:1 Chloroform/MeOH to 10:1 Chloroform/MeOH). The product containing fractions are concentrated to give the title compound (54 mg, 39%).

Preparation 9

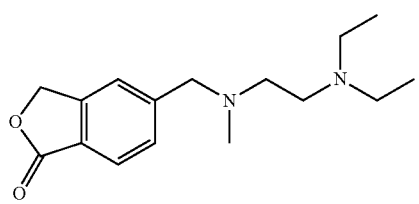 [SMILES: CCN(CC)CCN(C)Cc1ccc2c(c1)COC2=O]

2-{[(2-Diethylamino-ethyl)-methyl-amino]-methyl}-7H-furo[3,4-b]pyridin-5-one

In a process similar to that described in Preparation 8,5-oxo-5,7-dihydro-furo[3,4-b]pyridine-2-carbaldehyde (110 mg, 0.68 mmol) and N,N-diethyl-N'-methylethylenediamine (109 μL, 0.68 mmol) are reacted to provide the title compound as white solid (120 mg, 64%).

Example 7

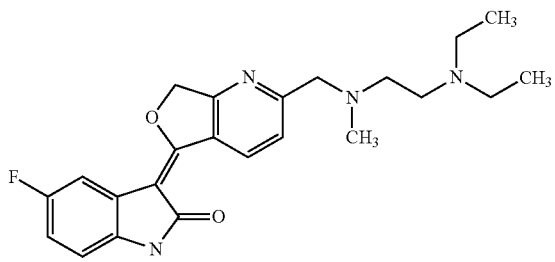 [SMILES: CCN(CC)CCN(C)Cc1ccc2c(n1)CO/C2=C1/C(=O)Nc2ccc(F)cc21]

3-(2-{[(2-Diethylamino-ethyl)-methyl-amino]-methyl}-7H-furo[3,4-b]pyridin-5-ylidene)-5-fluoro-1,3-dihydro-indol-2-one A solution of 5-fluoro-1,3-dihydro-indol-2-one (125 mg, 0.83 mmol.) in THF (4 mL) is treated with a solution of lithium bis(trimethylsilyl)amide (1.66 mL of a 1M solution in THF, 1.66 mmol) dropwise. The resulting solution is stirred for 20 min at room temperature. A solution of 2-{[(2-diethylamino-ethyl)-methyl-amino]-methyl}-7H-furo[3,4-b]pyridin-5-one (115 mg, 0.41 mmol) in THF (1.5 mL) is added dropwise to the reaction mixture. The resulting solution is stirred at room temperature for 4 h and then poured into 10% aqueous HCl solution (30 mL) previously cooled to 0° C. The ice bath is removed and the solution is stirred at room temperature for 16 h. The yellow solution is then cooled and solid NaHCO$_3$ is carefully added to adjust the solution to pH=8. The aqueous layer is extracted with EtOAc. The combined organic extracts are dried with anhydrous Na$_2$SO$_4$ and concentrated. The solid residue is broken up in isopropyl alcohol to give a yellow solid. The yellow solid is collected by filtration to give the title compound (102 mg, 61%).

Preparation 10

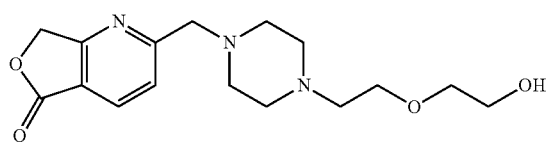 [SMILES: O=C1OCc2nc(CN3CCN(CCOCCO)CC3)ccc21]

2-{4-[2-(2-Hydroxy-ethoxy)-ethyl]-piperazin-1-ylmethyl}-7H-furo[3,4-b]pyridin-5-one In a process similar to that described in Preparation 8, 5-oxo-5,7-dihydro-furo[3,4-b]pyridine-2-carbaldehyde (150 mg, 0.92 mmol) and 1-[2-(2-hydroxyethoxy)ethyl]-piperazine (181 μL, 1.01 mmol) are reacted to provide the title compound as yellow oil (80 mg, 27%).

Example 8

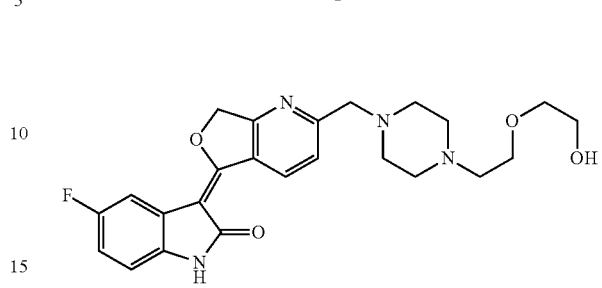

5-Fluoro-3-(2-{4-[2-(2-hydroxy-ethoxy)-ethyl]-piperazin-1-ylmethyl}-7H-furo[3,4-b]pyridin-5-ylidene)-1,3-dihydro-indol-2-one A solution of 5-fluoro-1,3-dihydro-indol-2-one (72 mg, 0.47 mmol) in THF (2 mL) is treated with a solution of lithium bis(trimethylsilyl)amide (1.2 mL of a 1M solution in THF, 1.2 mmol) dropwise. The resulting solution is stirred for 10 min at room temperature. A solution 2-{4-[2-(2-hydroxy-ethoxy)-ethyl]-piperazin-1-ylmethyl}-7H-furo[3,4-b]pyridin-5-one (77 mg, 0.24 mmol) in THF (1.5 mL) and added dropwise to the reaction mixture. The resulting solution is stirred for 4 h and is then treated with HCl (4M in dioxane, 5 mL) at 0° C. The reaction mixture is stirred at room temperature for 48 h. The reaction mixture is concentrated and the residue is treated with saturated aqueous NaHCO$_3$. The aqueous solution is extracted with EtOAc (2×). The combined organic extracts are dried (MgSO$_4$) and concentrated. The residue is purified by chromatography (silica gel, gradient elution 20:1 chloroform:MeOH to 10:1 chloroform:MeOH). The product containing fractions are concentrated and the residue is triturated from EtOAc-hexane and collected by filtration to give the title compound as a yellow solid (22 mg, 20%).

Preparation 11

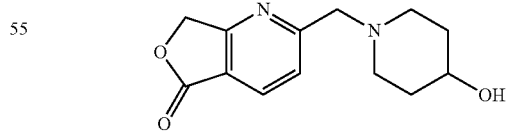

2-(5-Hydroxy-piperidin-2-ylmethyl)-7H-furo[3,4-b]pyridin-5-one

In a process similar to that described in Preparation 8, 5-oxo-5,7-dihydro-furo[3,4-b]pyridine-2-carbaldehyde (85 mg, 0.52 mmol) and 4-hydroxypiperidine (54 mg, 0.52 mmol) are reacted to provide the title compound as yellow oil (80 mg, 27%).

Example 9

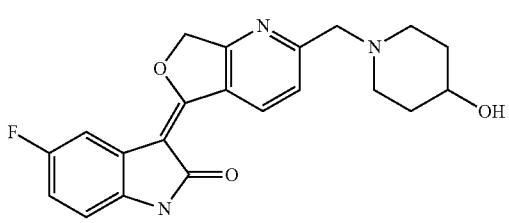 [SMILES: O=C1Nc2ccc(F)cc2/C1=C1\OCc2nc(CN3CCC(O)CC3)ccc21]

5-Fluoro-3-[2-(4-hydroxy-piperidin-1-ylmethyl)-7H-furo[3,4-b]pyridin-5-ylidene]-1,3-dihydro-indol-2-one A solution of 5-fluoro-1,3-dihydro-indol-2-one (110 mg, 0.72 mmol) in THF (5 mL) is treated with a solution of lithium bis(trimethylsilyl)amide (1.8 mL of a 1M solution in THF, 1.8 mmol) dropwise. The resulting solution is stirred at room temperature for 10 min. A solution of 2-(5-Hydroxy-piperidin-2-ylmethyl)-7H-furo[3,4-b]pyridin-5-one (90 mg, 0.36 mmol) in THF (2.5 mL) is added dropwise to the reaction mixture. The resulting solution is stirred for 4 h and is poured into a cold 4 M HCl solution in dioxane (4.5 mL) at 0° C. The resulting mixture is stirred at room temperature overnight. The reaction mixture is concentrated to partially remove the dioxane and is then partitioned between EtOAc and saturated aqueous NaHCO₃ solution. The organic phase is collected and the aqueous phase is extracted with additional EtOAc. The combined organic extracts are dried (Na₂SO₄), filtered and concentrated. The residue is purified by chromatography (silica gel) MeOH-Chloroform). The product containing fractions are concentrated to give the title compound as a yellow solid (41 mg, 30%).

Preparation 12

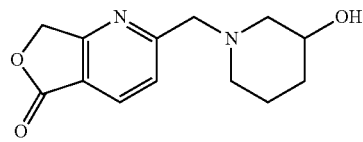 [SMILES: O=C1OCc2nc(CN3CCCC(O)C3)ccc21]

2-(4-Hydroxy-piperidin-2-ylmethyl)-7H-furo[3,4-b]pyridin-5-one

In a process similar to that described in Preparation 8,5-oxo-5,7-dihydro-furo[3,4-b]pyridine-2-carbaldehyde (85 mg, 0.52 mmol) and 3-hydroxypiperidine (54 mg, 0.52 mmol) are reacted to provide the title compound as yellow oil (100 mg, 77%).

Example 10

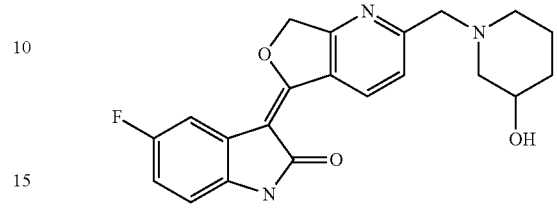

5-Fluoro-3-[2-(3-hydroxy-piperidin-1-ylmethyl)-7H-furo[3,4-b]pyridin-5-ylidene]-1,3-dihydro-indol-2-one A solution of 5-fluoro-1,3-dihydro-indol-2-one (75 mg, 0.49 mmol) in THF (4 mL) is treated with a solution of lithium bis(trimethylsilyl)amide (0.8 mL of a 1M solution in THF, 0.8 mmol) dropwise. The resulting solution is stirred at room temperature for 10 min. A solution of 2-(4-hydroxy-piperidin-2-ylmethyl)-7H-furo[3,4-b]pyridin-5-one (70 mg, 0.28 mmol) in THF (2 mL) is added dropwise to the reaction mixture. The resulting solution is stirred for 6 h. The reaction mixture is treated with additional lithium bis(trimethylsilyl)amide (0.3 mL of a 1M solution in THF, 0.3 mmol) dropwise and the reaction mixture is stirred at room temperature overnight. The reaction mixture is poured into a cold aqueous 10% HCl solution (7 mL). The resulting mixture is heated to 50° C. for 1 h and then poured into 100 mL ice water. Solid NaHCO₃ is carefully added to adjust the pH to 8. The aqueous layer is extracted with EtOAc (2×). The combined organic extracts are dried with Na₂SO₄, filtered and concentrated. The residue is purified by chromatography (silica gel, MeOH-Chloroform). The product containing fractions are concentrated to give the title compound as a yellow solid (11 mg, 10%).

Preparation 13

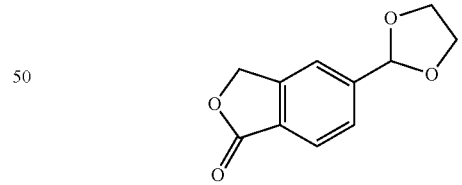

2-[1,3]Dioxolan-2-yl-7H-furo[3,4-b]pyridin-5-one

To a solution of 5-oxo-5,7-dihydro-furo[3,4-b]pyridine-2-carbaldehyde (100 mg, 0.61 mmol) in anhydrous benzene (5 mL) is added ethylene glycol (0.1 mL, 1.77 mmol), a catalytic amount p-toluenesulfonic acid monohydrate and 4 Å mole sieves. The reaction mixture is heated at a reflux temperature for 20 h. The reaction mixture is allowed to cool to room temperature and saturated. aqueous NaHCO₃ solution is added. The resulting mixture is filtered through celite, washed with saturated aqueous NaHCO₃ and EtOAc. The isolated organic layer is washed with brine (1×), dried with anhydrous Na$_2$SO$_4$, and concentrated. The residue is treated with EtOAc-Hexane (1:4) and the light brown solid which forms is collected by filtration and dried to give the title compound (42 mg, 33%).

Example 11

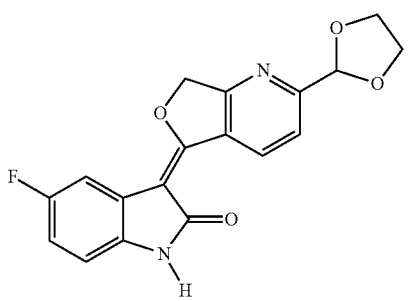 [SMILES: O=C1Nc2ccc(F)cc2/C1=C1\OCc2nc(C3OCCO3)ccc21]

(2-[1,3]Dioxolan-2-yl-7H-furo[3,4-b]pyridin-5-ylidene)-5-fluoro-1,3-dihydro-indol-2-one A solution of 1,3-dihydro-indol-2-one (45 mg, 0.30 mmol) in THF (0.5 mL) is placed under an Argon atmosphere and cooled in an ice bath. A solution of lithium bis(trimethylsilyl) amide (0.8 mL of a 1.0 M solution in THF, 0.8 mmol) is added slowly at 0° C. and the resulting solution is stirred for 10 min. The ice-bath is then removed and a solution of 2-[1,3]dioxolan-2-yl-7H-furo[3,4-b]pyridin-5-one (40 mg, 0.19 mmol) in THF (1.5 mL) is added dropwise to the reaction mixture. The resulting solution is stirred for 4 h and is then poured into a 10% aqueous HCl solution (40 mL). The resulting suspension is stirred at room temperature for 48 h. The solid which precipitated from solution is collected by filtration and purified by chromatography (silica gel). The product containing fractions are concentrated to give the title compound (10 mg, 15%).

Preparation 14

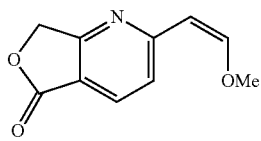 [SMILES: CO/C=C\c1ccc2c(n1)COC2=O]

E-2-(2-Methoxy-vinyl)-7H-furo[3,4-b]pyridin-5-one and Preparation 15

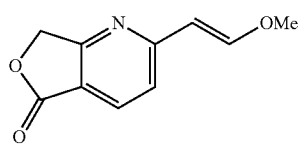 [SMILES: CO/C=C/c1ccc2c(n1)COC2=O]

Z-2-(2-Methoxy-vinyl)-7H-furo[3,4-b]pyridin-5-one

To a suspension of (methoxymethyl)triphenylphosphorium chloride (889 mg, 2.6 mmol) in anhydrous THF (10 mL) is added slowly to a solution of potassium tert butoxide in tBuOH (2.4 mL of a 1.0 M solution in tBuOH, 2.4 mmol) under an argon atmosphere. The brown reaction mixture is stirred at room temperature for 30 min, cooled to 0° C. and treated with 5-oxo-5,7-dihydro-furo[3,4-b]pyridine-2-carbaldehyde (326 mg, 2.0 mmol) in one portion. The dark brown reaction mixture is stirred at room temperature for 3 h and then poured into saturated aqueous NH$_4$Cl solution (30 mL). The reaction mixture is extracted with EtOAc (2×). The combined organic extracts are dried Na$_2$SO$_4$, filtered and concentrated. The residue is purified by chromatography (silica gel, EtOAc/hexane) to give the higher Rf E-isomer, E-2-(2-Methoxy-vinyl)-7H-furo[3,4-b]pyridin-5-one (111 mg, 0.58 mmol) and lower Rf Z-isomer, Z-2-(2-Methoxy-vinyl)-7H-furo[3,4-b]pyridin-5-one (61 mg, 0.32 mmol). Total yield is 45%.

Preparation 16

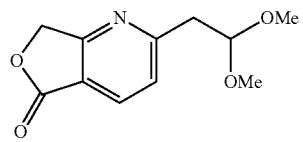 [SMILES: COC(Cc1ccc2c(n1)COC2=O)OC]

2-(2,2-Dimethoxy-ethyl)-7H-furo[3,4-b]pyridin-5-one

To a solution of 2-(2-methoxy-vinyl)-7H-furo[3,4-b]pyridin-5-one (108 mg, 0.57 mmol) in anhydrous MeOH (10 mL) is added three drops of concentrated sulfuric acid. The reaction solution is stirred and heated at 70° C. for 18 h at which time the starting material is consumed. The reaction mixture is then diluted with EtOAc (100 mL), and then washed with saturated aqueous NaHCO$_3$ (2×75 mL). The organic solution is dried (Na$_2$SO$_4$) and concentrated to give the title compound as a brown oil (104 mg, 83%).

Example 12

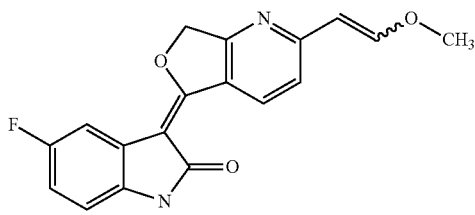

5-Fluoro-3-[2-(2-methoxy-vinyl)-7H-furo[3,4-b]pyridin-5-ylidene]-1,3-dihydro-indol-2-one A solution of 5-fluoro-1,3-dihydro-indol-2-one (176 mg, 1.16 mmol) in THF (5 mL) is treated with a solution of lithium bis(trimethylsilyl)amide (2.3 mL of a 1M solution in THF, 2.3 mmol) dropwise. The resulting solution is stirred at room temperature for 10 min. A solution of 2-(2-methoxy-vinyl)-7H-furo[3,4-b]pyridin-5-one (111 mg, 0.58 mmol) in THF (2 mL) is added dropwise to the reaction mixture. The resulting solution is stirred for 3 h and is poured into cold 10% aqueous HCl solution (30 mL) at 0° C. The resulting mixture is stirred at 50° C. for 1 h and room temperature overnight. The solid which formed is collected by filtration and dried to give the title compound as a light brown solid (65 mg, 35%).

Example 13

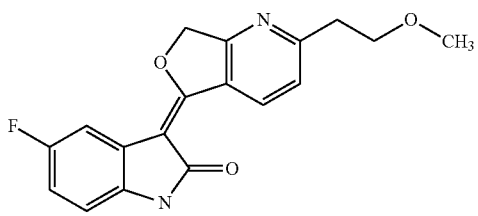 [SMILES: COCCc1ccc2c(n1)CO/C2=C1/C(=O)Nc2ccc(F)cc21]

5-Fluoro-3-[2-(2-methoxy-ethyl)-7H-furo[3,4-b]pyridin-5-ylidene]-1,3-dihydro-indol-2-one A solution of 5-fluoro-3-[2-(2-methoxy-vinyl)-7H-furo[3,4-b]pyridin-5-ylidene]-1,3-dihydro-indol-2-one (27 mg, 0.08 mmol) in 10 mL MeOH is treated with palladium (10% on activated carbon, 27 mg) under an argon atmosphere. The resulting mixture is subject to hydrogenation at a pressure of 35 psi for 12 h. The reaction mixture is filtered, concentrated, and the residue is chromatographed (silica gel, MeOH-Chloroform). The product containing fractions are concentrated to give the title compound as yellow solid (5 mg, 18%).

Example 14

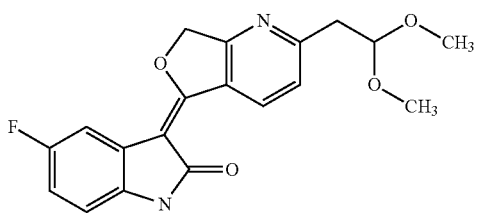 [SMILES: COC(Cc1ccc2c(n1)CO/C2=C1/C(=O)Nc2ccc(F)cc21)OC]

3-[2-(2,2-Dimethoxy-ethyl)-7H-furo[3,4-b]pyridin-5-ylidene]-5-fluoro-1,3-dihydro-indol-2-one A solution of 5-fluoro-1,3-dihydro-indol-2-one (141 mg, 0.93 mmol.) in THF (4 mL) is treated with a solution of lithium bis(trimethylsilyl)amide (1.9 mL of a 1 M solution in THF, 1.9 mmol) dropwise. The resulting solution is stirred at room temperature for 10 min. A solution of 2-(2,2-dimethoxy-ethyl)-7H-furo[3,4-b]pyridin-5-one (104 mg, 0.47 mmol in THF (1 mL) is added dropwise to the reaction mixture. The resulting solution is stirred for 1.5 h and is then poured into cold aqueous 2N $H_2SO_4$ solution (10 mL) at 0° C. The resulting mixture is heated at 45° C. for 30 min and then cooled to room temperature and stirred overnight. The reaction mixture is poured into ice water (150 mL) and stirred for 2 h. The solid which formed is collected to give the title compound as a brown solid (76 mg, 46%).

Example 15

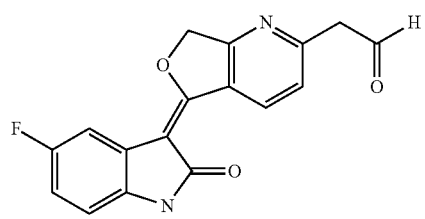 [SMILES: O=CCc1ccc2c(n1)CO/C2=C1/C(=O)Nc2ccc(F)cc21]

[5-(5-Fluoro-2-oxo-1,2-dihydro-indol-3-ylidene)-5,7-dihydro-furo[3,4-b]pyridin-2-yl]-acetaldehyde A solution of 3-[2-(2,2-dimethoxy-ethyl)-7H-furo[3,4-b]pyridin-5-ylidene]-5-fluoro-1,3-dihydro-indol-2-one (52 mg, 0.16 mmol) in THF (5 mL) is treated with 0.63 mL of an aqueous 2.5 M sulfuric acid solution (0.63 mL). The reaction mixture is heated to 60° C. for 1 h, cooled to room temperature and poured into 100 mL ice water with stirring. The brown solid which precipitated is collected by filtration, washed with water, and dried under vacuum to give the title compound as brown solid (27 mg, 54%).

Example 16

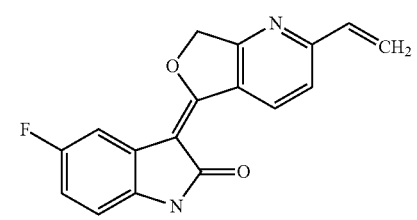 [SMILES: C=Cc1ccc2c(n1)CO/C2=C1/C(=O)Nc2ccc(F)cc21]

5-Fluoro-3-(2-vinyl-7H-furo[3,4-b]pyridin-5-ylidene)-1,3-dihydro-indol-2-one and Example 28

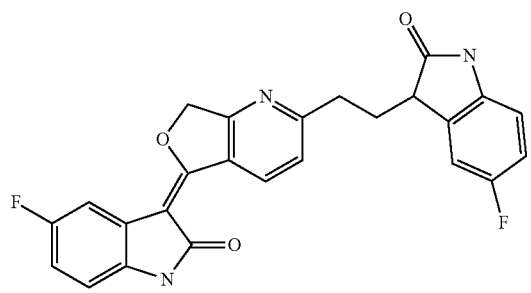 [SMILES: O=C1Nc2ccc(F)cc2/C1=C1\OCc2nc(CCC3C(=O)Nc4ccc(F)cc43)ccc21]

5-Fluoro-3-[5-fluoro-2(2-oxo-2,3-dihydro-1H-indol-3-yl)ethyl]-1,3-dihydroindol-2-one A solution of 5-fluoro-1,3-dihydro-indol-2-one (3.38 g, 22.4 mmol.) in THF (100 mL) is treated with a solution of lithium bis(trimethylsilyl)amide (45 mL of a 1 M solution in THF, 45 mmol) dropwise. The resulting solution is stirred at room temperature for 15 min and then treated with 2-vinyl-7H-furo[3,4-b]pyridin-5-one (1.2 g, 7.45 mmol) in one portion. The reaction mixture is stirred at room temperature for 2 h. The reaction mixture is poured into a cold aqueous 2 N HCl solution (200 mL). The ice bath is removed and the reaction mixture is heated at 50° C. for 2 h and then stirred at room temperature overnight. The reaction mixture is treated with 100 mL ice water and stirred for 30 min. The yellow solid is collected by filtration and dried. The solid is purified by chromatography (silica gel, MeOH-Chloroform) and the product containing fractions concentrated. The residue is triturated with MeOH and the solid is collected by filtration and dried to give 5-Fluoro-3-(2-vinyl-7H-furo[3,4-b]pyridin-5-ylidene)-1,3-dihydro-indol-2-one (Example 6) as an orange solid (0.82 g, 37%). The filtrate is absorbed to silica gel and subjected to chromatography (silica gel, EtOAc-hexane) to afford (Example 28) as a yellow solid (50 mg, 1.5%).

Example 16

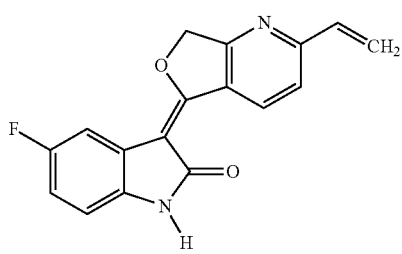 [SMILES: C=Cc1ccc2c(n1)CO/C2=C1/C(=O)Nc2ccc(F)cc21]

5-Fluoro-3-(2-vinyl-7H-furo[3,4-b]pyridin-5-ylidene)-1,3-dihydro-indol-2-one

A solution of 5-fluoro-1,3-dihydro-indol-2-one (1.13 g, 7.44 mmol) in THF (70 mL) is placed under an Argon atmosphere and cooled in an ice bath. A solution of lithium bis(trimethylsilyl)amide (14.9 mL of a 1.0 M solution in THF, 14.9 mmol) is added slowly at 0° C. and the resulting solution is stirred for 10 min. Solid 2-vinyl-7H-furo[3,4-b]pyridin-5-one (600 mg, 3.72 mmol) is added in one portion. The reaction mixture is stirred for 4.5 h and then poured into an aqueous 1N HCl solution (150 mL). The resulting mixture is stirred at room temperature for 70 h during which time a yellow solid precipitated from solution. The solid is collected by filtration and washed with aqueous 10% HCl solution, MeOH (3×5 mL) and Et₂O (3×5 mL). The solid is dried under vacuum overnight to give the title compound (260 mg, 24%).

Example 17

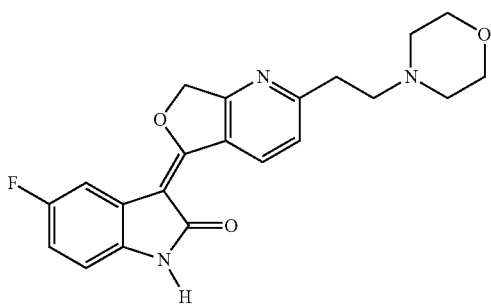 [SMILES: O=C1Nc2ccc(F)cc2/C1=C1\OCc2nc(CCN3CCOCC3)ccc21]

5-Fluoro-3-[2-(2-morpholin-4-yl-ethyl)-7H-furo[3,4-b]pyridin-5-ylidene]-1,3-dihydro-indol-2-one A solution of 5-fluoro-1,3-dihydro-indol-2-one (70 mg, 0.46 mmol) in THF (0.6 mL) is placed under an Argon atmosphere and cooled in an ice bath. A solution of lithium bis(trimethylsilyl)amide (1.2 mL of a 1.0 M solution in THF, 1.2 mmol) is added slowly at 0° C. and the resulting solution is stirred for 10 min. The ice-bath is then removed and a solution of 2-(2-morpholin-4-yl-ethyl)-7H-furo[3,4-b]pyridin-5-one (80 mg, 0.32 mmol) in THF (2 mL) and added dropwise to the reaction mixture. The resulting solution is stirred for 4 h and then poured into an aqueous 10% HCl solution (40 mL). The resulting suspension is stirred at room temperature for 48 h. The yellow solid which precipitated from solution is collected by filtration and washed with 10% HCl, MeOH (3×5 mL) and Et₂O (3×5 mL), and dried under vacuum overnight to give the title compound (33 mg, 27%).

Example 18

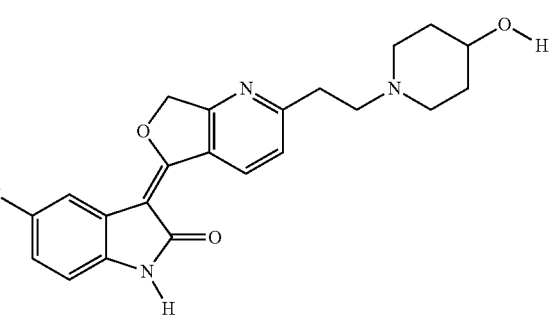

3-[2-(2-Diethylamino-ethyl)-7H-furo[3,4-b]pyridin-5-ylidene]-5-fluoro-1,3-dihydro-indol-2-one A solution of 5-fluoro-3-(2-vinyl-7H-furo[3,4-b]pyridin-5-ylidene)-1,3-dihydro-indol-2-one (60 mg, 0.20 mmol) and diethylamine (250 mg, 3.42 mmol) are reacted in a sealed tube at 100° C. for 2 h. The reaction vessel is cooled and additional diethylamine (250 mg, 3.42 mmol) in dioxane (10 mL) is added. The reaction vessel is sealed and heated at 100° C. overnight. The reaction mixture is cooled and treated with triethylamine (15 drops). The reaction mixture is loaded onto silica gel and purified by chromatography (silica gel, MeOH-Chloroform). The product containing fractions are concentrated to provide the title compound (13 mg, 18%) as a yellow solid.

Example 19

5-Fluoro-3-{2-[2-(4-hydroxy-piperidin-1-yl)-ethyl]-7H-furo[3,4-b]pyridin-5-ylidene}-1,3-dihydro-indol-2-one A solution of 5-fluoro-3-(2-vinyl-7H-furo[3, 4-1)]pyridin-5-ylidene)-1,3-dihydro-indol-2-one (50 mg, 0.17 mmol) in dioxane (10 mL) is treated with 4-hydroxypiperidine (260 mg, 2.57 mmol) and 10 drops of glacial AcOH. The reaction is stirred at 100° C. for 1 h and then cooled to room temperature. The reaction mixture is treated with triethylamine (2 mL) and is loaded onto silica gel. Purification by chromatography (silica gel) gave the title compound (57 mg, 85%).

Example 20

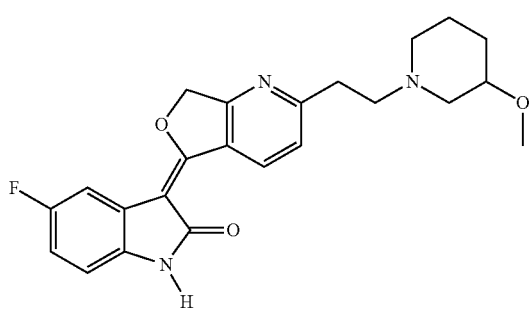 [SMILES: COC1CCCN(CCc2ccc3c(n2)CO/C3=C2/C(=O)Nc3ccc(F)cc32)C1]

5-Fluoro-3-{2-[2-(3-hydroxy-piperidin-1-yl)-ethyl]-7H-furo[3,4-b]pyridin-5-ylidene}-1,3-dihydro-indol-2-one Following the method described in Example 19, 5-fluoro-3-(2-vinyl-7H-furo[3,4-b]pyridin-5-ylidene)-1,3-dihydro-indol-2-one (50 mg, 0.17 mmol) and 3-hydroxypiperidine (300 mg, 2.67 mmol) are reacted to provide the title compound (45 mg, 67%).

Example 21

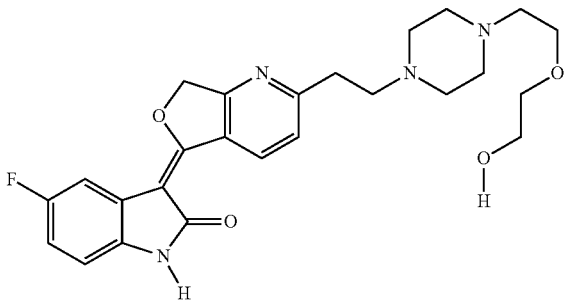 [SMILES: O=C1Nc2ccc(F)cc2/C1=C1\OCc2nc(CCN3CCN(CCOCCO)CC3)ccc21]

5-Fluoro-3-[2-(2-{4-[2-(2-hydroxy-ethoxy)-ethyl]-piperazin-1-yl}-ethyl)-7H-furo[3,4-b]pyridin-5-ylidene]-1,3-dihydro-indol-2-one Following the method described in Example 19, 5-fluoro-3-(2-vinyl-7H-furo[3,4-b]pyridin-5-ylidene)-1,3-dihydro-indol-2-one (45 mg, 0.153 mmol) and 1-hydroxyethoxypiperazine (300 mg, 1.72 mmol) are reacted to provide the title compound (18 mg, 25%).

Example 22

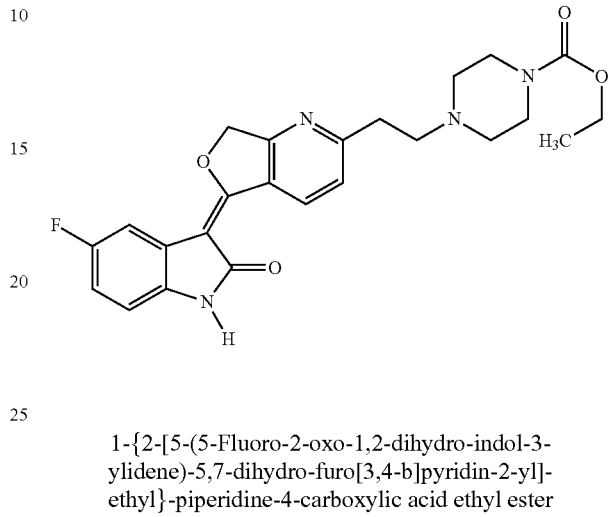

1-{2-[5-(5-Fluoro-2-oxo-1,2-dihydro-indol-3-ylidene)-5,7-dihydro-furo[3,4-b]pyridin-2-yl]-ethyl}-piperidine-4-carboxylic acid ethyl ester Following the method described in Example 19, 5-fluoro-3-(2-vinyl-7H-furo[3,4-b]pyridin-5-ylidene)-1,3-dihydro-indol-2-one (50 mg, 0.17 mmol) and ethyl isonipecotate (300 mg, 1.96 mmol) are reacted to provide the title compound (20 mg, 26%).

Example 23

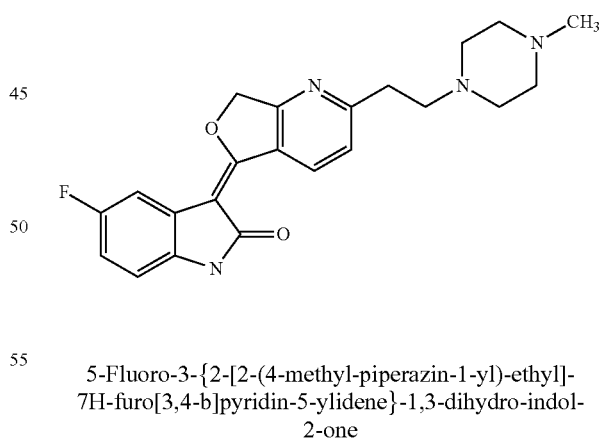

5-Fluoro-3-{2-[2-(4-methyl-piperazin-1-yl)-ethyl]-7H-furo[3,4-b]pyridin-5-ylidene}-1,3-dihydro-indol-2-one Following the method described in Example 19, 5-fluoro-3-(2-vinyl-7H-furo[3,4-b]pyridin-5-ylidene)-1,3-dihydro-indol-2-one (60 mg, 0.20 mmol) and N-methylpiperazine (300 mg, 3.00 mmol) are heated 100° C. for 2 h. The reaction mixture is cooled and treated with triethylamine (10 drops). The reaction mixture is loaded onto silica gel and purified by chromatography (silica gel, gradient elution, 2% MeOH/

Chloroform to 20% MeOH/chloroform) to provide the title compound (80 mg, 100%) as a yellow solid.

Example 24

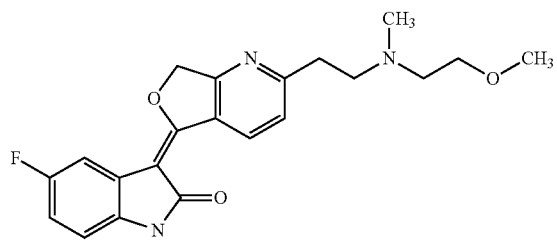 [SMILES: COCCN(C)CCc1ccc2c(n1)CO/C2=C1/C(=O)Nc2ccc(F)cc21]

5-Fluoro-3-(2-{2-[(2-methoxy-ethyl)-methyl-amino]-ethyl}-7H-furo[3,4-b]pyridin-5-ylidene)-1,3-dihydro-indol-2-one Following the method described in Example 19, 5-fluoro-3-(2-vinyl-7H-furo[3,4-b]pyridin-5-ylidene)-1,3-dihydro-indol-2-one (80 mg, 0.27 mmol) and (2-methoxyethyl)methylamine (450 mg, 5.04 mmol) are heated 100° C. for 2 h. Additional (2-methoxyethyl)methylamine is added and heating is continued for 1 hr. The reaction mixture is cooled and treated with triethylamine (10 drops). The reaction mixture is loaded onto silica gel and purified by chromatography (silica gel, MeOH-Chloroform). The product containing fractions are concentrated and triturated with EtOAc-hexane. The solid obtained is collected by filtration and dried to provide the title compound (55 mg, 53%) as a yellow solid.

Example 25

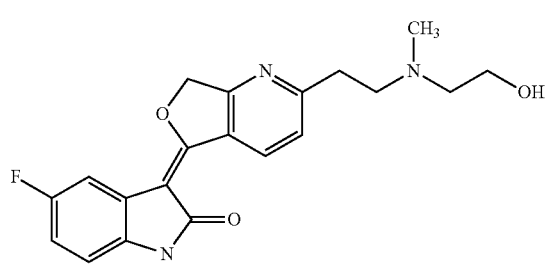 [SMILES: CN(CCO)CCc1ccc2c(n1)CO/C2=C1/C(=O)Nc2ccc(F)cc21]

5-Fluoro-3-(2-{2-[(2-hydroxy-ethyl)-methyl-amino]-ethyl}-7H-furo[3,4-b]pyridin-5-ylidene)-1,3-dihydro-indol-2-one Following the method described in Example 19, 5-fluoro-3-(2-vinyl-7H-furo[3,4-b]pyridin-5-ylidene)-1,3-dihydro-indol-2-one (65 mg, 0.22 mmol) and (2-methoxyethyl)methylamine (300 mg, 3.99 mmol) and AcOH (12 drops) are heated 100° C. for 2 h. Additional (2-methoxyethyl)methylamine is added and heating is continued for 1 hr. The reaction mixture is cooled and treated with triethylamine (10 drops). The reaction mixture is loaded onto silica gel and purified by chromatography (silica gel, MeOH-Chloroform). The product containing fractions are concentrated and the residue is triturated with EtOAc-hexane. The solid which formed is collected by filtration and dried under vacuum to provide the title compound (53 mg, 65%) as a yellow solid.

Example 26

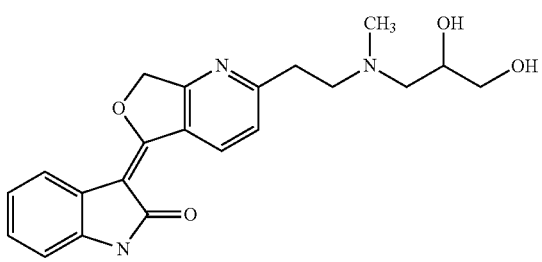 [SMILES: CN(CCc1ccc2c(n1)CO/C2=C1/C(=O)Nc2ccccc21)CC(O)CO]

3-(2-{2-[(2,3-Dihydroxy-propyl)-methyl-amino]-ethyl}-7H-furo[3,4-b]pyridin-5-ylidene)-5-fluoro-1,3-dihydro-indol-2-one Following the method described in Example 19, 5-fluoro-3-(2-vinyl-7H-furo[3,4-b]pyridin-5-ylidene)-1,3-dihydro-indol-2-one (65 mg, 0.22 mmol) and are converted to the title compound.

Example 27

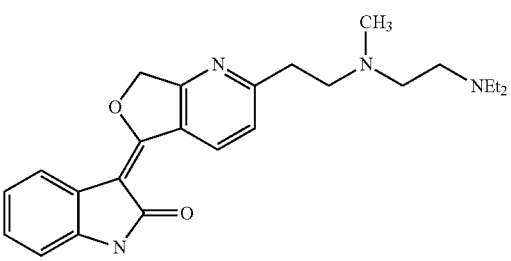

3-(2-{2-[(2-Diethylamino-ethyl)-methyl-amino]-ethyl}-7H-furo[3,4-b]pyridin-5-ylidene)-5-fluoro-1,3-dihydro-indol-2-one Following the method described in Example 19, 5-fluoro-3-(2-vinyl-7H-furo[3,4-b]pyridin-5-ylidene)-1,3-dihydro-indol-2-one and are converted to the title compound Preparation 17

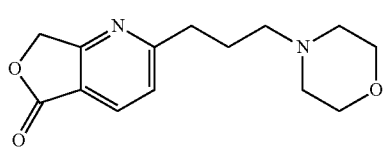 [SMILES: O=C1OCc2nc(CCCN3CCOCC3)ccc21]

2-(3-Morpholin-4-yl-propyl)-7H-furo[3,4-b]pyridin-5-one

In a process similar to that described in Preparation 8, 3-(5-oxo-5,7-dihydro-furo[3,4-b]pyridin-2-yl)-propionaldehyde and morpholine are reacted to provide the title compound.

Example 29

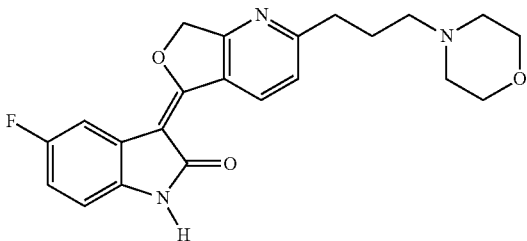 [SMILES: O=C1Nc2ccc(F)cc2/C1=C1\OCc2nc(CCCN3CCOCC3)ccc21]

5-Fluoro-3-[2-(3-morpholin-4-yl-propyl)-7H-furo[3,4-b]pyridin-5-ylidene]-1,3-dihydro-indol-2-one A solution of 5-fluoro-1,3-dihydro-indol-2-one (190 mg, 1.26 mmol.) in THF (1 mL) is placed under an argon atmosphere cooled in an ice bath. A solution of lithium bis(trimethylsilyl)amide (4 mL of a 1M in THF, 4 mmol) is added slowly at 0° C. and the resulting solution is stirred for 10 min. The ice-bath is then removed and a solution of 2-(3-Morpholin-4-yl-propyl)-7H-furo[3,4-b]pyridin-5-one (220 mg, 0.84 mmol) in THF (15 mL) is added dropwise to the reaction mixture. The resulting solution is stirred for 4.5 h and then poured into an aqueous 10% HCl solution (50 mL). The resulting solution is stirred for 70 h at room temperature. The solid which precipitated from solution is collected by filtration and washed sequentially with small volumes of MeOH, EtOAc, and Et$_2$O and dried under vacuum give the title compound (110 mg, 33%).

Preparation 18

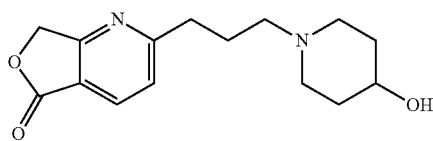 [SMILES: O=C1OCc2nc(CCCN3CCC(O)CC3)ccc21]

2-[3-(4-Hydroxy-piperidin-1-yl)-propyl]-7H-furo[3,4-b]pyridin-5-one

In a process similar to that described in Preparation 8,3-(5-Oxo-5,7-dihydro-furo[3,4-b]pyridin-2-yl)-propionaldehyde and 4-hydroxypiperidine are reacted to provide the title compound.

Example 30

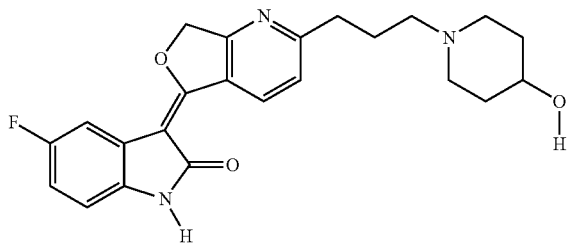 [SMILES: O=C1Nc2ccc(F)cc2/C1=C1\OCc2nc(CCCN3CCC(O)CC3)ccc21]

5-Fluoro-3-{2-[3-(4-hydroxy-piperidin-1-yl)-propyl]-7H-furo[3,4-b]pyridin-5-ylidene}-1,3-dihydro-indol-2-one A solution of 5-fluoro-1,3-dihydro-indol-2-one (163 mg, 1.09 mmol.) in THF (2 mL) is placed under an argon atmosphere cooled in an ice bath. A solution of lithium bis(trimethylsilyl)amide (3.6 mL of a 1M in THF, 3.6 mmol, 5 eq.) is added slowly at 0° C. and the resulting solution is stirred for 20 min. The ice-bath is then removed and a solution of 2-[3-(4-Hydroxy-piperidin-1-yl)-propyl]-7H-furo[3,4-b]pyridin-5-one (200 mg, 0.72 mmol) in THF (1 mL) is added dropwise to the reaction mixture. The lactone does not dissolve well, so rest of the lactone is added as a solid. The resulting solution is stirred for 3 h and then poured into 10% aqueous HCl solution (50 mL) and stirred for 48 h at room temperature. Extraction with EtOAc followed by chromatography (silica gel, MeOH/Chloroform) provides the title compound (10 mg) as a solid.

Preparation 19

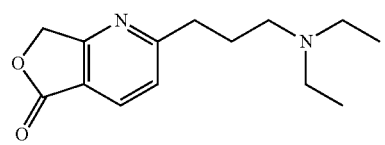 [SMILES: CCN(CC)CCCc1ccc2c(n1)COC2=O]

2-(3-Diethylamino-propyl)-7H-furo[3,4-b]pyridin-5-one

In a process similar to that described in Preparation 8,3-(5-Oxo-5,7-dihydro-furo[3,4-b]pyridin-2-yl)-propionaldehyde (61 mg, 0.32 mmol) and N,N-diethyl-N'-methylethylenediamine (33 μL, 0.32 mmol) are reacted to provide the title compound as white solid (60 mg, 76%).

Example 31

3-[2-(3-Diethylamino-propyl)-7H-furo[3,4-b]pyridin-5-ylidene]-5-fluoro-1,3-dihydro-indol-2-one

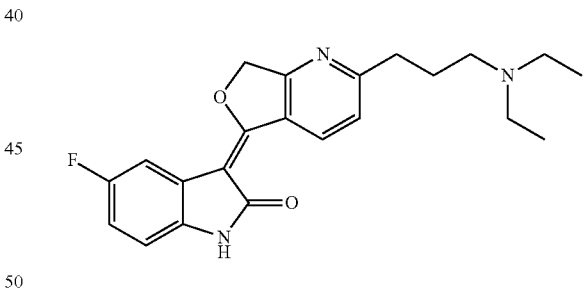

A solution of 5-Fluoro-1,3-dihydro-indol-2-one (100 mg) in anhydrous. THF (5 mL) at room temperature is treated with lithium bis(trimethylsilyl)amide (1.0 M solution in tetrahydrofuran, 1.33 mL, 6 equiv). The resulting mixture is stirred at room temperature for 10 min, then is added 2-(3-diethylamino-propyl)-7H-furo[3,4-b]pyridin-5-one (55 mg, 1 equiv) in one portion. The reaction mixture is stirred at room temperature until both TLC and HPLC indicated the disappearance of the phthalide. The reaction mixture is poured into 10% aqueous HCl solution (10 mL) with stirring. Then it is heated at 50° C. for 2 h and further stirred at room temperature for an overnight. The mixture is poured into 100 mL ice water, to which solid NaHCO$_3$ is carefully added to adjust pH to 8. The aqueous layer is extracted with EtOAc (2×). Organic layer is combined, dried with anhydrous Na$_2$SO$_4$, filtered and concentrated. The residue obtained purified by chromatography (silica gel, MeOH-chloroform) to give the title compound as a yellow solid (31 mg, 37%).

Preparation 20

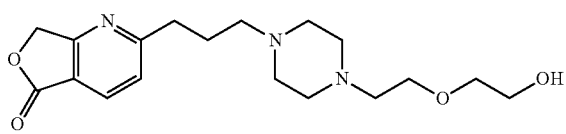 [SMILES: O=C1OCc2nc(CCCN3CCN(CCOCCO)CC3)ccc21]

2-(3-{4-[2-(2-Hydroxy-ethoxy)-ethyl]-piperazin-1-yl}-propyl)-7H-furo[3,4-b]pyridin-5-one In a process similar to that described in Preparation 8, 3-(5-Oxo-5,7-dihydro-furo[3,4-b]pyridin-2-yl)-propionaldehyde (76 mg, 0.4 mmol) and 1-[2-(2-hydroxyethoxy)ethyl]-piperazine (66 µL, 0.4 mmol) are reacted to provide the title compound as an oil (110 mg, 79%).

Example 32

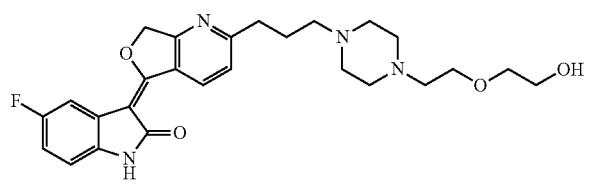 [SMILES: O=C1Nc2ccc(F)cc2/C1=C1\OCc2nc(CCCN3CCN(CCOCCO)CC3)ccc21]

5-Fluoro-3-[2-(3-{4-[2-(2-hydroxy-ethoxy)-ethyl]-piperazin-1-yl}-propyl)-7H-furo[3,4-b]pyridin-5-ylidene]-1,3-dihydro-indol-2-one A solution of 5-fluoro-1,3-dihydro-indol-2-one (143 mg, 0.95 mmol) in THF (4 mL) at room temperature is treated with lithium bis(trimethylsilyl)amide (1.0 M solution in tetrahydrofuran, 2.2 mL, 2.2 mmol) and stirred for 10 min. A solution of 2-(3-{4-[2-(2-Hydroxy-ethoxy)-ethyl]-piperazin-1-yl}-propyl)-7H-furo[3,4-b]pyridin-5-one (110 mg, 0.31 mmol) in anhydrous THF (2 mL) is added. The reaction mixture is stirred at room temperature for 2 h. The reaction mixture is poured into aqueous 2N HCl (10 mL) with stirring and is heated at 60° C. for 2.5 h. The mixture is then poured into 100 mL ice water, to which solid NaHCO₃ is carefully added to adjust pH to 8. The aqueous layer is extracted with chloroform (3×). The combined organic layers are dried with anhydrous Na₂SO₄, and concentrated. The residue purified by column chromatography (MeOH-chloroform) to give the title compound as a yellow solid (51 mg, 34%).

Preparation 21

2-[3-(3-Hydroxy-piperidin-1-yl)-propyl]-7H-furo[3,4-b]pyridin-5-one

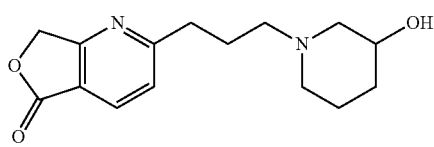 [SMILES: O=C1OCc2nc(CCCN3CCCC(O)C3)ccc21]

In a process similar to that described in Preparation 8, 3-(5-Oxo-5,7-dihydro-furo[3,4-b]pyridin-2-yl)-propionaldehyde (76 mg, 0.4 mmol) and 3-hydroxypiperidine (41 mg, 0.4 mmol) are reacted to provide the title compound as a white solid (82 mg, 74%).

Preparation 22

2-{3-[(2-Methoxy-ethyl)-methyl-amino]-propyl}-7H-furo[3,4-b]pyridin-5-one

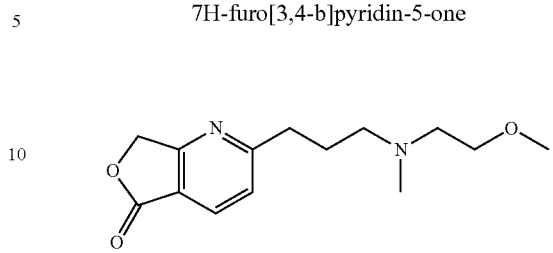

A similar procedure is applied to (0.4 mmol, 1 equiv) and N-(2-methoxyethyl)methylamine (43.1 µL, 1 equiv) to yield the above compound as a light yellow oil (90 mg, 85.2%).

Example 33

5-Fluoro-3-{2-[3-(3-hydroxy-piperidin-1-yl)-propyl]-7H-furo[3,4-b]pyridin-5-ylidene}-1,3-dihydro-indol-2-one

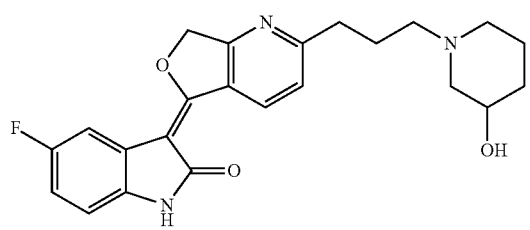 [SMILES: O=C1Nc2ccc(F)cc2/C1=C1\OCc2nc(CCCN3CCCC(O)C3)ccc21]

In a manner similar to that described in Example 29, 2-[3-(3-Hydroxy-piperidin-1-yl)-propyl]-7H-furo[3,4-b]pyridin-5-one (80 mg, 1 equiv) is converted to the title compound as a yellow solid (28 mg, 24%).

Preparation 22

2-{3-[(2-Methoxy-ethyl)-methyl-amino]-propyl}-7H-furo[3,4-b]pyridin-5-one

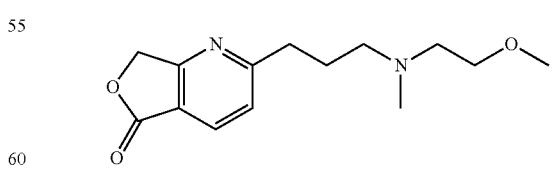

In a process similar to that described in Preparation 8, 3-(5-Oxo-5,7-dihydro-furo[3,4-b]pyridin-2-yl)-propionaldehyde (76 mg, 0.4 mmol) and N-(2-methoxyethyl)methylamine (43 µL, 0.4 mmol) are reacted to provide the title compound as pale yellow oil (90 mg, 85%).

Example 34

5-Fluoro-3-(2-{3-[(2-methoxy-ethyl)-methyl-amino]-propyl}-7H-furo[3,4-b]pyridin-5-ylidene)-1,3-dihydro-indol-2-one

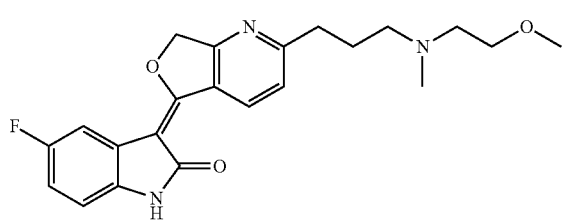 [SMILES: COCCN(C)CCCc1ccc2c(n1)CO/C2=C1/C(=O)Nc2ccc(F)cc21]

In a manner similar to that described in Example 29, 2-{3-[(2-Methoxy-ethyl)-methyl-amino]-propyl}-7H-furo[3,4-b]pyridin-5-one (85 mg, 1 equiv) is converted to the title compound as a yellow solid (50.8 mg, 40%).

Preparation 23

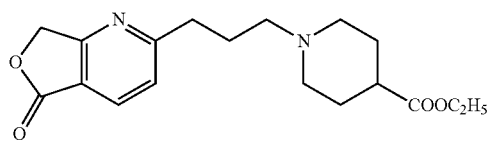

1-[3-(5-Oxo-5,7-dihydro-furo[3,4-b]pyridin-2-yl)-propyl]-piperidine-4-carboxylic acid ethyl ester In a process similar to that described in Preparation 8 3-(5-oxo-5,7-dihydro-furo[3,4-b]pyridin-2-yl)-propionaldehyde (76 mg, 0.4 mmol) and ethyl isonipecotate (62 µL, 0.4 mmol) are reacted to provide the title compound as white solid (110 mg, 83%).

Example 35

1-{3-[5-(5-Fluoro-2-oxo-1,2-dihydro-indol-3-ylidene)-5,7-dihydro-furo[3,4-b]pyridin-2-yl]-propyl}-piperidine-4-carboxylic acid

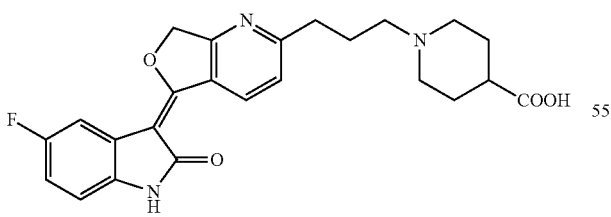

A solution of 5-fluoro-1,3-dihydro-indol-2-one (150 mg, 1.0 mmol) in THF (5 mL) at room temperature is treated with lithium bis(trimethylsilyl)amide (1.0 M solution in tetrahydrofuran, 2.0 mL, 2.0 mmol) and stirred for 10 min. A solution of 1-[3-(5-oxo-5,7-dihydro-furo[3,4-b]pyridin-2-yl)-propyl]-piperidine-4-carboxylic acid ethyl ester (110 mg, 1 equiv) in anhydrous THF (2 mL) is added. The reaction mixture is stirred at room temperature for 3 h. The reaction mixture is poured into aqueous 2N HCl solution (10 mL) with stirring. Then it is heated at 60° C. for 2 h. To the mixture is then added ice water (100 mL) followed by the careful addition of saturated aqueous NaHCO₃ to adjust the pH to 8. The foamy suspension is filtered and a greenish yellow solid is obtained. This material is purified by column chromatography to give the title compound as a yellow solid (48 mg, 33%).

Preparation 24

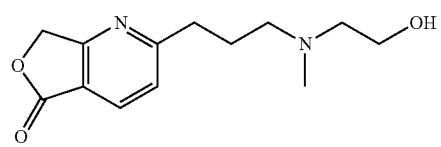 [SMILES: CN(CCO)CCCc1ccc2c(n1)COC2=O]

2-{3-[(2-Hydroxy-ethyl)-methyl-amino]-propyl}-7H-furo[3,4-b]pyridin-5-one In a process similar to that described in Preparation 8,3-(5-Oxo-5,7-dihydro-furo[3,4-b]pyridin-2-yl)-propionaldehyde (76 mg, 0.4 mmol) and 2-(methylamino)ethanol (32 µL, 0.4 mmol) are reacted to provide the title compound as an oil (61 mg, 61%).

Example 36

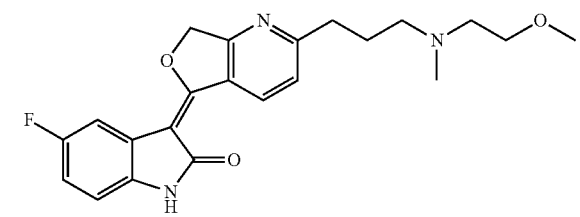 [SMILES: COCCN(C)CCCc1ccc2c(n1)CO/C2=C1/C(=O)Nc2ccc(F)cc21]

5-Fluoro-3-(2-{3-[(2-methoxy-ethyl)-methyl-amino]-propyl}-7H-furo[3,4-b]pyridin-5-ylidene)-1,3-dihydro-indol-2-one In a manner similar to that described in Example 29, 2-{3-[(2-Hydroxy-ethyl)-methyl-amino]-propyl}-7H-furo[3,4-b]pyridin-5-one (85 mg, 1 equiv) is converted to the title compound as a yellow solid (50.8 mg, 40%).

Preparation 25

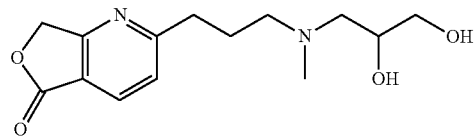 [SMILES: CN(CCCc1ccc2c(n1)COC2=O)CC(O)CO]

2-{3-[(2,3-Dihydroxy-propyl)-methyl-amino]-propyl}-7H-furo[3,4-b]pyridin-5-one

In a process similar to that described in Preparation 8,3-(5-Oxo-5,7-dihydro-furo[3,4-b]pyridin-2-yl)-propionaldehyde (139 mg, 0.73 mmol) and 3-methylamino-1,2-propanediol (77 mg, 0.73 mmol) are reacted to provide the title compound as an oil (108 mg, 52%).

Example 37

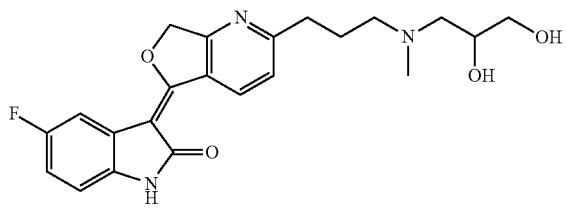 [SMILES: CN(CCCc1ccc2c(n1)CO/C2=C1/C(=O)Nc2ccc(F)cc21)CC(O)CO]

3-(2-{3-[(2,3-Dihydroxy-propyl)-methyl-amino]-propyl}-7H-furo[3,4-b]pyridin-5-ylidene)-5-fluoro-1,3-dihydro-indol-2-one In a manner similar to that described in Example 29, 2-{3-[(2,3-Dihydroxy-propyl)-methyl-amino]-propyl}-7H-furo[3,4-b]pyridin-5-one (107 mg, 1 equiv) is converted to the title compound as a yellow solid (10 mg, 6%).

Preparation 26

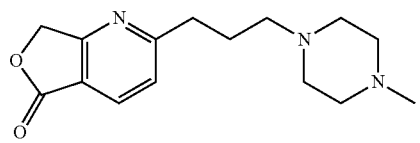 [SMILES: CN1CCN(CCCc2ccc3c(n2)COC3=O)CC1]

2-[3-(4-Methyl-piperazin-1-yl)-propyl]-7H-furo[3,4-b]pyridin-5-one

In a process similar to that described in Preparation 8, 3-(5-Oxo-5,7-dihydro-furo[3,4-b]pyridin-2-yl)-propionaldehyde (63 mg, 0.33 mmol) and 1-methylpiperazine (33 mg, 0.33 mmol) are reacted to provide the title compound as white solid (76 mg, 84%).

Example 38

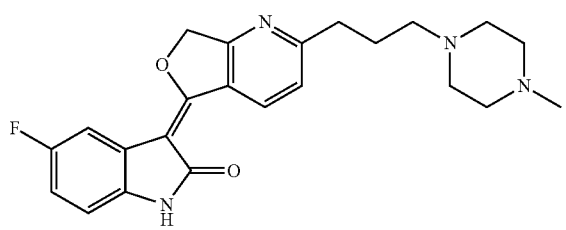 [SMILES: CN1CCN(CCCc2ccc3c(n2)CO/C3=C2/C(=O)Nc3ccc(F)cc32)CC1]

5-Fluoro-3-{2-[3-(4-methyl-piperazin-1-yl)-propyl]-7H-furo[3,4-b]pyridin-5-ylidene}-1,3-dihydro-indol-2-one In a manner similar to that described in Example 29, 2-[3-(4-Methyl-piperazin-1-yl)-propyl]-7H-furo[3,4-b]pyridin-5-one (76 mg, 1 equiv) is converted to the title compound as a yellow solid (37 mg, 33%).

Preparation 27

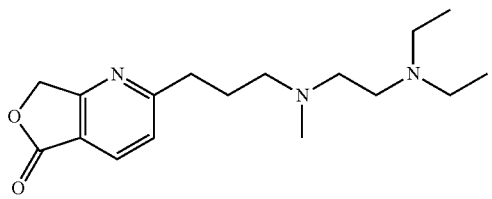 [SMILES: CCN(CC)CCN(C)CCCc1ccc2c(n1)COC2=O]

2-{3-[(2-Diethylamino-ethyl)-methyl-amino]-propyl}-7H-furo[3,4-b]pyridin-5-one

In a process similar to that described in Preparation 8, 3-(5-Oxo-5,7-dihydro-furo[3,4-b]pyridin-2-yl)-propionaldehyde (63 mg, 0.33 mmol) and N,N-diethyl-N'-methylethylenediamine (43 mg, 0.32 mmol) are reacted to provide the title compound as white solid (64 mg, 63%).

Example 39

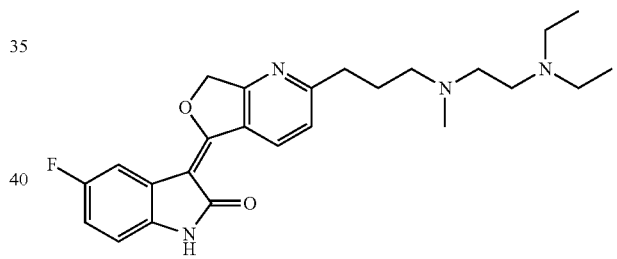

3-(2-{3-[(2-Diethylamino-ethyl)-methyl-amino]-propyl}-7H-furo[3,4-b]pyridin-5-ylidene)-5-fluoro-1,3-dihydro-indol-2-one In a manner similar to that described in Example 29, 2-{3-[(2,3-Dihydroxy-propyl)-methyl-amino]-propyl}-7H-furo[3,4-b]pyridin-5-one (64 mg, 1 equiv) is converted to the title compound as a yellow solid (25 mg, 27%).

Example 40

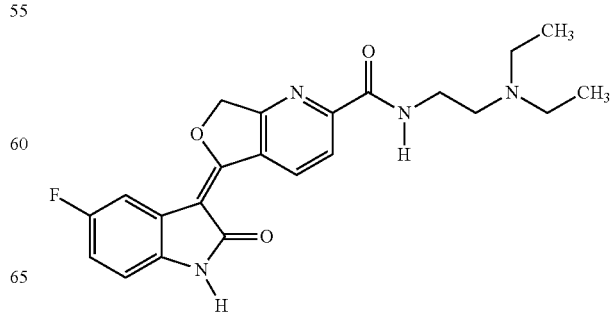

5-(5-Fluoro-2-oxo-1,2-dihydro-indol-3-ylidene)-5,7-dihydro-furo[3,4-b]pyridine-2-carboxylic acid (2-diethylamino-ethyl)-amide A solution of 5-fluoro-1,3-dihydro-indol-2-one (76 mg, 0.46 mmol) in THF (3 mL) is treated with a solution of lithium bis(trimethylsilyl)amide (1.2 mL of a 1M solution in THF, 1.2 mmol) dropwise. The resulting solution is stirred at room temperature for 10 min. A solution of 5-oxo-5,7-dihydro-furo[3,4-b]pyridine-2-carboxylic acid (2-diethylamino-ethyl)-amide (70 mg, 0.25 mmol) in THF (2 mL) is added dropwise to the reaction mixture. The resulting solution is stirred for 4 h and is poured into a cold 4M HCl solution in dioxane (3 mL) at 0° C. The resulting mixture is stirred at room temperature overnight. The reaction mixture is concentrated to partially remove the dioxane and is then partitioned between EtOAc and saturated aqueous NaHCO$_3$ solution. The organic phase is collected and the aqueous phase is extracted with additional EtOAc. The combined organic extracts are dried (Na$_2$SO$_4$), filtered and concentrated. The residue is purified by chromatography (silica gel, MeOH-Chloroform). The product containing fraction are concentrated and the residue is treated with EtOAc-hexane (1:1). The solid is collected by filtration to give the title compound as an orange solid (51 mg, 49%).

Preparation 28

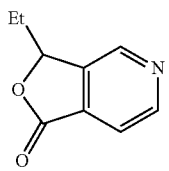 [SMILES: CCC1OC(=O)c2ccncc21]

3-Ethyl-3H-furo[3,4-c]pyridin-1-one

A solution of 2,2,6,6-tetramethyl-piperidine (20.3 ml, 120 mmol) in a 250 ml round bottomed flask equipped with a magnetic stirrer, is put under argon atmosphere and 60 ml of dry THF is added. The reaction mixture is cooled to −78° C. by adding a controlled amount of dry ice to an acetone bath. The cooled reaction mixture is treated dropwise with nBuLi solution (64 mL of a 2.5 M solution in hexanes, 160 mmol) and the reaction is let stir at −78° C. for 0.5 h. A solution of isonicotinic acid (4.92 g, 40 mmol) in THF (60 mL) is added dropwise to the reaction at −78° C. The reaction is stirred at −78° C. for 1 h and is then warmed to −20° C. The reaction mixture is treated with propionaldehyde (7.2 ml, 100 mmol, 2.5 eq) dropwise at −50° C. The reaction is stirred at −20° C. for 2 h and warmed to room temperature overnight. The reaction mixture is concentrated and the residue is dissolved in water and ether. The aqueous layer is collected and extracted with dichloromethane and ether (6×50 ml). The aqueous phase is concentrated and the residue is dissolved in EtOH (30 mL) and acetic acid (2 mL) and heated at reflux overnight under argon. The reaction mixture is cooled to room temperature and concentrated. The residue is purified by chromatography (silica gel, MeOH/chloroform) to give the title compound (0.674 g, 10%) as an oil.

Example 41

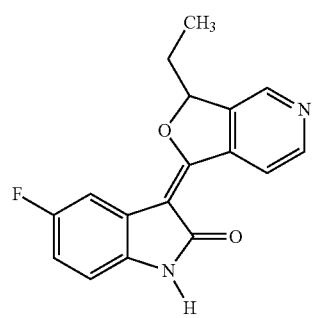 [SMILES: CCC1O/C(=C2/C(=O)Nc3ccc(F)cc32)c2ccncc21]

3-(3-Ethyl-3H-furo[3,4-c]pyridin-1-ylidene)-5-fluoro-1,3-dihydro-indol-2-one

A solution of 5-fluoro-1,3-dihydro-indol-2-one (936 mg, 6.20 mmol.) in THF (6 mL) is cooled to 0° C. under an argon atmosphere and treated with a solution of lithium bis(trimethylsilyl)amide (12.4 mL of a 1 M solution in THF, 12.4 mmol) dropwise. The resulting solution is stirred at room temperature for 10 min. A solution of 3-ethyl-3H-furo[3,4-c]pyridin-1-one (674 mg, 4.13 mmol) in THF (7 mL) is added dropwise to the reaction mixture. The resulting solution is stirred for 4 h. The reaction mixture is poured into aqueous 10% HCl solution (160 mL). The resulting mixture is heated to 90° C. for 2 h and stirred at room temperature for 36 h. The precipitate which formed is collected by filtration, washed with small volumes of ethyl acetate (10×3 mL) and dried under vacuum to give the title compound as a yellow solid (720 mg, 59%).

Preparation 29

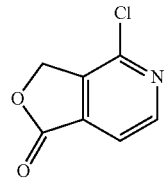 [SMILES: O=C1OCc2c1ccnc2Cl]

4-Chloro-3H-furo[3,4-c]pyridin-1-one

A solution of 2,2,6,6-tetramethyl-piperidine (4.05 ml, 24 mmol) in a 100 ml round bottomed flask equipped with a magnetic stirrer, is put under argon atmosphere and 20 ml of dry THF is added. The reaction mixture is cooled to −50° C. by adding a controlled amount of dry ice to an acetone bath. The cooled reaction mixture is treated dropwise with nBuLi solution (8.8 mL of a 2.5 M solution in hexanes, 22 mmol) and the reaction is let stir at −50° C. for 0.5 h. Solid 2-chloro-isonicotinic acid, (1.58 g, 10 mmol) is added as a solid to the reaction mixture at −50° C. The reaction is stirred at −50° C. for 0.5 h. The reaction mixture is treated with paraformaldehyde (7 equivalents) dropwise at −50° C. The reaction is stirred at −50° C. for 2 h and warmed to room temperature overnight. The reaction mixture is concentrated to remove solvent and water and ether are added. The aqueous layer is extracted with ether (6×50 ml). The aqueous phase is treated with aqueous 1N HCl solution, until the pH of aqueous layer is ~5 and is then extracted with ether (2×40 mL) The aqueous solution is treated with aqueous 1N HCl solution until the pH ~2. An oily residue separated which from solution is collected to give the title compound as a yellow oil (0.62 g, 36%).

Example 42

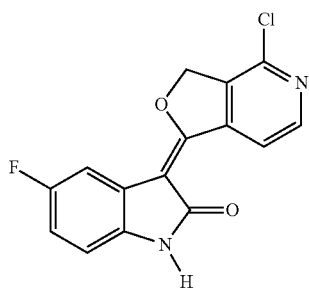 [SMILES: O=C1Nc2ccc(F)cc2/C1=C1\OCc2c1ccnc2Cl]

3-(4-Chloro-3H-furo[3,4-c]pyridin-1-ylidene)-5-fluoro-1,3-dihydro-indol-2-one

A solution of 5-fluoro-1,3-dihydro-indol-2-one (825 mg, 5.46 mmol.) in THF (5 mL) is cooled to 0° C. under an Argon atmosphere and treated with a solution of lithium bis(trimethylsilyl)amide (11 mL of a 1 M solution in THF, 11 mmol) dropwise. The resulting solution is stirred at room temperature for 10 min. A solution of 4-chloro-3H-furo[3,4-c]pyridin-1-one (620 mg, 3.67 mmol) in THF (7 mL) is added dropwise to the reaction mixture. The resulting solution is stirred for 4 h. The reaction mixture is poured into aqueous 10% HCl solution (160 mL). The resulting mixture is heated to 90° C. for 2 h and then stirred at room temperature for 36 h. The precipitate which formed is collected by filtration, washed with small volumes of ethyl acetate (10×3 mL) and dried under vacuum to give the title compound as a yellow solid (810 mg, 73%).

Example 43

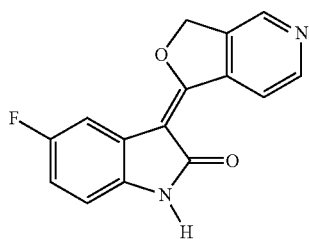 [SMILES: O=C1Nc2ccc(F)cc2/C1=C1\OCc2cnccc21]

3-(3H-Furor[3,4-c]pyridin-1-ylidene)-5-methyl-1,3-dihydro-indol-2-one

A solution of 3-(4-chloro-3H-furo[3,4-c]pyridin-1-ylidene)-5-fluoro-1,3-dihydro-indol-2-one (50 mg, 0.17 mmol) is dissolved in ethanol (10 mL) and treated with 5% Pd/C (50 mg), ammonium formate (500 mg, 7.93 mmol) The reaction mixture is stirred at room temperature for 24 h. The reaction mixture is evaporated and the residue is loaded onto silica gel and purified by chromatography (silica gel). The product containing fractions are concentrated to give the title compound as a yellow solid (20 mg, 45%).

Preparation 30

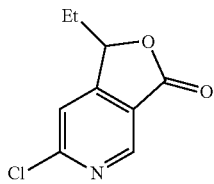 [SMILES: CCC1OC(=O)c2cnc(Cl)cc21]

6-Chloro-1-ethyl-1H-furo[3,4-c]pyridin-3-one

A solution of 2,2,6,6-tetramethyl-piperidine (5 ml, 30 mmol) in a 100 ml round bottomed flask equipped with a magnetic stirrer, is put under argon atmosphere and 20 ml of dry THF is added. The reaction mixture is cooled to −50° C. by adding a controlled amount of dry ice to an acetone bath. The cooled reaction mixture is treated dropwise with nBuLi solution (16 mL of a 2.5 M solution in hexanes, 40 mmol) and the reaction is let stir at that −50 C for 0.5 h. A solution of 6-chloro-nicotinic acid (1.58 g, 10 mmol) in THF (20 mL) is added dropwise to the reaction at −50° C. The reaction is stirred at −50° C. for 1.5 h and then cooled to −78° C. The reaction mixture is treated with propionaldehyde (4.2 ml, 58 mmol) dropwise at −50° C. The reaction is stirred at −78° C. for 2 h and warmed to room temperature overnight. The reaction mixture is concentrated to remove solvent and water and ether are added. The aqueous layer is extracted with ether (6×50 ml). The aqueous phase is treated with aqueous 1N HCl solution, until the pH of aqueous layer is ~6 and is then extracted with ether (3×40 mL) The aqueous solution is treated with aqueous 1N HCl solution until the pH ~2 and solution is heated at 100° C. overnight. An oily residue separates from solution. Dichloromethane is added to the aqueous phase which dissolves the oily residue. Without extracting, the solution is poured into a separatory funnel and the organic phase is collected. The organic phase is washed with saturated aqueous NaHCO$_3$ solution, dried over Na$_2$SO$_4$, filtered and concentrated to give the title compound (1.45 g, 73%) as a yellow oil.

Example 44

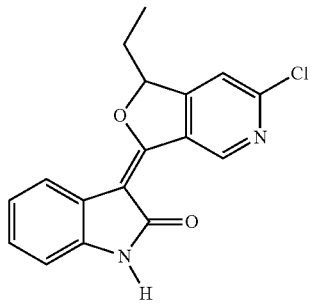 [SMILES: CCC1O/C(=C2/C(=O)Nc3ccccc32)c2cnc(Cl)cc21]

3-(6-Chloro-1-ethyl-1H-furo[3,4-c]pyridin-3-ylidene)-1,3-dihydro-indol-2-one

A solution of 1,3-dihydro-indol-2-one (650 mg, 4.77 mmol.) in THF (10 mL) is cooled to 0° C. under an argon atmosphere and treated with a solution of lithium bis(trimethylsilyl)amide (9.6 mL of a 1 M solution in THF, 9.6 mmol) dropwise. The ice bath is removed and 6-chloro-1-ethyl-1H-furo[3,4-c]pyridin-3-one (630 mg, 3.18 mmol) is added directly as a solid. The resulting solution is stirred for 4.5 h. The reaction mixture is poured into aqueous 10% HCl solution (100 mL) and stirred at room temperature for 10 min and then heated at 90-100° C. for 2 h. The reaction mixture is cooled to room temperature for 36 h during which time a precipitate formed. The precipitate which formed is collected by filtration and dried to give the title compound as an orange solid (670 mg, 67%).

Example 45

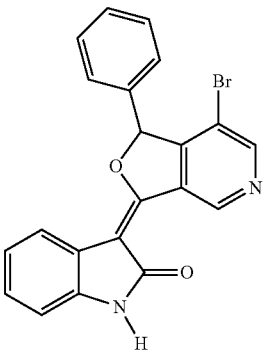 [SMILES: O=C1Nc2ccccc2/C1=C1\OC(c2ccccc2)c2c(Br)cncc21]

3-(7-Bromo-1-phenyl-1-1H-furo[3,4-c]pyridin-3-ylidene)-1,3-dihydro-indol-2-one

A solution of 1,3-dihydro-indol-2-one (225 mg, 1.55 mmol) in THF (6 mL) is cooled to 0° C. under an Argon atmosphere and treated with a solution of lithium bis(trimethylsilyl)amide (3.5 mL of a 1 M solution in THF, 3.5 mmol) dropwise. The resulting solution is stirred at room temperature for 10 min. A solution of 7-bromo-1-phenyl-1H-furo[3,4-c]pyridin-3-one (305 mg, 1.0 mmol, AcOH salt) is added as a solid to the reaction mixture. The resulting solution is stirred for 3.5 h. The reaction mixture is poured into aqueous 10% HCl solution (50 mL) and stirred at room temperature for 48 h. The precipitate which formed is collected by filtration and dried. The solid obtained is purified by chromatography (silica gel, 30% EtOAc/hexane). The product containing fractions are concentrated to give the title compound as a yellow solid (120 mg, 27%).

Preparation 32

6,7-Dichloro-1-phenyl-1-1H-furo[3,4-c]pyridin-3-one

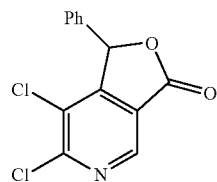 [SMILES: O=C1OC(c2ccccc2)c2c1cnc(Cl)c2Cl]

A solution of 2,2,6,6-tetramethyl-piperidine (7.5 ml, 44 mmol) in a 250 ml round bottomed flask equipped with a magnetic stirrer, is put under argon atmosphere and 30 ml of dry THF is added. The reaction mixture is cooled to −50° C. by adding a controlled amount of dry ice to an acetone bath. The cooled reaction mixture is treated dropwise with nBuLi solution (16.3 mL of a 2.5 M solution in hexanes, 40 mmol) and the reaction is let stir at that −50° C. for 0.5 h. A solution of 5,6-dichloro-nicotinic acid, (3.7 g, 18.5 mmol) in THF (15 mL) is added dropwise to the reaction at −50° C. The reaction is stirred at −50° C. for 0.5 h. The reaction mixture is treated with benzaldehyde (2.5 ml, 24 mmol) dropwise at −50° C. The reaction is stirred at −50° C. for 2 h and warmed to room temperature overnight. The reaction mixture is concentrated to remove solvent and water and ether are added. The aqueous layer is extracted with ether (6×50 ml). The aqueous phase is treated with 1N HCl, until the pH of aqueous layer is ~6 and is then extracted with ether (3×40 mL) The aqueous solution is treated with 1N HCl solution until the pH ~2 and solution is heated at 100° C. overnight. On cooling a white precipitate appeared. The precipitate is filtered off and washed with bicarbonate and air-dried to give the title compound (4.6 g, 89%) as a white solid.

Example 46

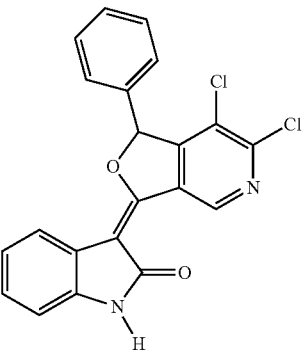 [SMILES: O=C1Nc2ccccc2/C1=C1\OC(c2ccccc2)c2c1cnc(Cl)c2Cl]

3-(6,7-Dichloro-1-phenyl-1-1H-furo[3,4-c]pyridin-3-ylidene)-1,3-dihydro-indol-2-one A solution of 1,3-dihydro-indol-2-one (1.31 g, 9.84 mmol.) in THF (10 mL) is cooled to 0° C. under an Argon atmosphere and treated with a solution of lithium bis(trimethylsilyl)amide (10 mL of a 1 M solution in THF, 10 mmol) dropwise. Additional THF (6 mL) is added followed by lithium bis(trimethylsilyl)amide (9 mL of a 1 M solution in THF, 9.0 mmol) dropwise. The resulting solution is stirred at room temperature for 10 min. A solution of 6,7-dichloro-1-phenyl-1H-furo[3,4-c]pyridin-3-one (1.78 g, 6.36 mmol) in THF (10 mL) is added dropwise to the reaction mixture. The resulting solution is stirred for 4.5 h. The reaction mixture is poured into aqueous 10% HCl solution (125 mL) and stirred at room temperature for 36 h. The precipitate which formed is collected by filtration and dried under vacuum to give the title compound as an orange solid (2.0 g, 80%).

Example 47

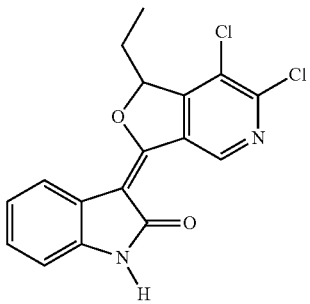 [SMILES: CCC1O/C(=C2/C(=O)Nc3ccccc32)c2cnc(Cl)c(Cl)c21]

3-(6,7-Dichloro-1-ethyl-1H-furo[3,4-c]pyridin-3-ylidene)-1,3-dihydro-indol-2-one In a manner similar to Example 46, 6,7-dichloro-1-ethyl-1H-furo[3,4-c]pyridine-3-one and 1,3-dihydroindol-2-one are converted to the title compound.

Example 48

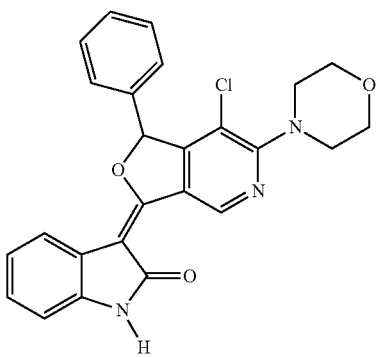 [SMILES: O=C1Nc2ccccc2/C1=C1\OC(c2ccccc2)c2c1cnc(N1CCOCC1)c2Cl]

3-(7-Chloro-6-morpholin-4-yl-1-phenyl-1H-furo[3,4-c]pyridin-3-ylidene)-1,3-dihydro-indol-2-one A solution of morpholine (155 mg, 1.78 mmol) in 4 mL of isopropanol is treated with 3-(6,7-Dichloro-1-phenyl-1H-furo[3,4-c]pyridin-3-ylidene)-1,3-dihydro-indol-2-one (100 mg, 0.25 mmol) in one portion and the reaction mixture is heated to reflux overnight. The reaction mixture is cooled to room temperature, absorbed to silica gel and purified by chromatography (silica gel, MeOH, chloroform). The product containing fractions are concentrated to give the title compound as a yellow solid (50 mg, 45%).

Example 49

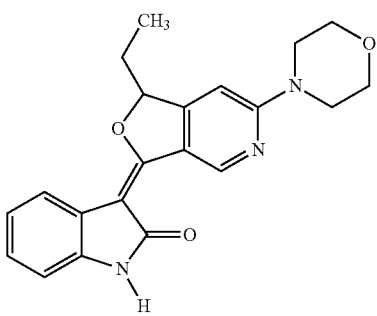 [SMILES: CCC1O/C(=C2/C(=O)Nc3ccccc32)c2cnc(N3CCOCC3)cc21]

3-(1-Ethyl-6-morpholin-4-yl-1H-furo[3,4-c]pyridin-3-ylidene)-1,3-dihydro-indol-2-one A solution of morpholine (200 mg, 2.29 mmol) in 4 mL of isopropanol is treated with 3-(6-Chloro-1-ethyl-1H-furo[3,4-c]pyridin-3-ylidene)-1,3-dihydro-indol-2-one (100 mg, 0.31 mmol) in one portion and the reaction mixture is heated to reflux for 72 h. The reaction mixture is cooled to room temperature and the solid which precipitated from solution is collected by filtration and dried to give the title compound as a yellow solid (61 mg, 54%).

Example 50

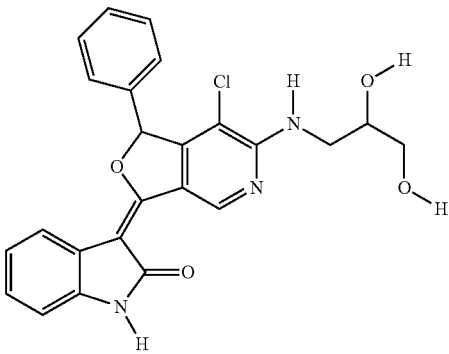 [SMILES: O=C1Nc2ccccc2/C1=C1\OC(c2ccccc2)c2c1cnc(NCC(O)CO)c2Cl]

3-[7-Chloro-6-(2,3-dihydroxy-propylamino)-1-(1-propenyl-buta-1,3-dienyl)-1H-furo[3,4-c]pyridin-3-ylidene]-1,3-dihydro-indol-2-one A solution of 3-amino-propane-1,2-diol (225 mg, 2.47 mmol) in 4 mL of isopropanol is treated with 3-(6,7-Dichloro-1-phenyl-1H-furo[3,4-c]pyridin-3-ylidene)-1,3-dihydro-indol-2-one (100 mg, 0.25 mmol) in one portion. The reaction mixture is heated to reflux overnight, cooled to room temperature and concentrated. The residue is purified by chromatography (silica gel, gradient elution 5% MeOH/Chloroform to 15% MeOH/Chloroform). The product containing fractions are concentrated to give the title compound as a yellow solid (56 mg, 50%).

Example 51

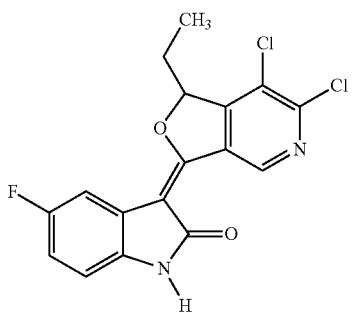 [SMILES: CCC1O/C(=C2/C(=O)Nc3ccc(F)cc32)c2cnc(Cl)c(Cl)c21]

3-(6,7-Dichloro-1-ethyl-1H-furo[3,4-c]pyridin-3-ylidene)-5-fluoro-1,3-dihydro-indol-2-one A solution of 5-fluoro-1,3-dihydro-indol-2-one (1.44 g, 9.52 mmol.) in THF (10 mL) is cooled to 0° C. under an Argon atmosphere and treated with a solution of lithium bis(trimethylsilyl)amide (19 mL of a 1 M solution in THF, 19.0 mmol) dropwise. The resulting solution is stirred at 0° C. for 10 min and then warmed room temperature. A solution of 6,7-dichloro-1-ethyl-1H-furo[3,4-c]pyridin-3-one (1.47 g, 6.33 mmol) in THF (9 mL) is added dropwise to the reaction mixture and the reaction mixture is stirred for 4 h. The reaction mixture is poured into aqueous 10% HCl solution (200 mL). The resulting mixture is heated to 100° C. for 2 h and then stirred at room temperature for 36 h. The precipitate which formed is collected by filtration, washed with small volumes of ethyl acetate (10×3 mL) and dried under vacuum to give the title compound as a yellow solid (810 mg, 35%).

Example 52

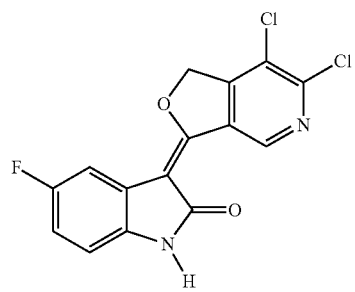 [SMILES: O=C1Nc2ccc(F)cc2/C1=C1\OCc2c1cnc(Cl)c2Cl]

3-(6,7-Dichloro-1H-furo[3,4-c]pyridin-3-ylidene)-5-fluoro-1,3-dihydro-indol-2-one A solution of 5-fluoro-1,3-dihydro-indol-2-one (1.44 g, 9.54 mmol.) in THF (10 mL) is cooled to 0° C. under an argon atmosphere and treated with a solution of lithium bis(trimethylsilyl)amide (19 mL of a 1 M solution in THF, 19.0 mmol) dropwise. The resulting solution is stirred at 0° C. for 10 min and warmed room temperature. A solution of 6,7-dichloro-1H-furo[3,4-c]pyridin-3-one (1.28 g, 6.27 mmol) in THF (9 mL) is added dropwise to the reaction mixture. The resulting solution is stirred at room temperature for 4 h and the reaction mixture is then poured into aqueous 10% HCl solution (200 mL). The resulting mixture is heated to 90° C. for 2 h and stirred at room temperature for 36 h. The precipitate which formed is collected by filtration, washed with small volumes of ethyl acetate (10×3 mL) and dried under vacuum to give the title compound as a yellow solid (1.43 g, 68%).

Example 53

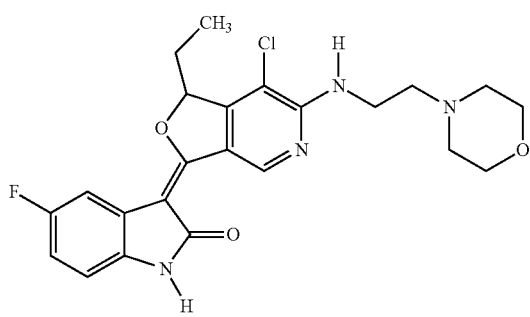 [SMILES: CCC1O/C(=C2/C(=O)Nc3ccc(F)cc32)c2cnc(NCCN3CCOCC3)c(Cl)c21]

3-[7-Chloro-1-ethyl-6-(2-morpholin-4-yl-ethylamino)-1H-furo[3,4-c]pyridin-3-ylidene]-5-fluoro-1,3-dihydro-indol-2-one A solution of 2-morpholin-4-yl-ethylamine (178 mg, 1.37 mmol) in 3 mL of dioxane is treated with 3-(6,7-dichloro-1-ethyl-1H-furo[3,4-c]pyridin-3-ylidene)-5-fluoro-1,3-dihydro-indol-2-one (100 mg, 0.27 mmol) in one portion and the reaction mixture is heated to 100° C. for 12 hr. The reaction mixture is treated with 12 mL of water and then heated at reflux for 1 hr. The reaction mixture is cooled to room temperature and the precipitate which formed is collected by filtration and dried under vacuum to give the title compound as a yellow solid (22 mg, 18%).

Example 54

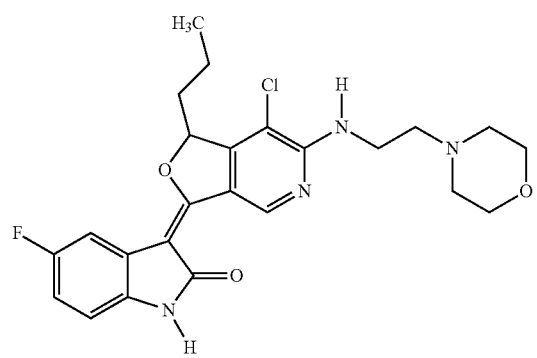 [SMILES: CCCC1O/C(=C2/C(=O)Nc3ccc(F)cc32)c2cnc(NCCN3CCOCC3)c(Cl)c21]

3-[7-Chloro-6-(2-morpholin-4-yl-ethylamino)-1-propyl-1H-furo[3,4-c]pyridin-3-ylidene]-5-fluoro-1,3-dihydro-indol-2-one A solution of 2-morpholin-4-yl-ethylamine (320 mg, 2.45 mmol) in 3 mL of dioxane is treated with 3-(6,7-dichloro-1-ethyl-1H-furo[3,4-c]pyridin-3-ylidene)-5-fluoro-1,3-dihydro-indol-2-one (100 mg, 0.26 mmol) in one portion and the reaction mixture is heated to 100° C. overnight. The reaction mixture is concentrated and the residue is purified by chromatography (silica gel, 5% MeOH/EtOAc). The product containing fractions are concentrated to give the title compound as a yellow solid (29 mg, 24%).

Example 55

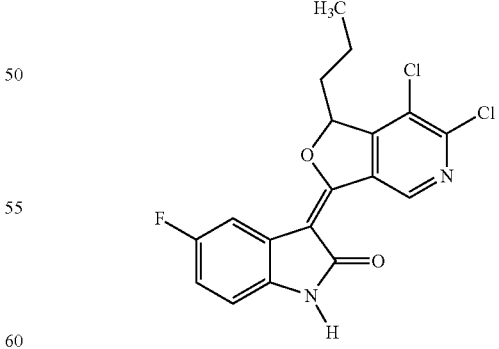

3-(6,7-Dichloro-1-propyl-1H-furo[3,4-c]pyridin-3-ylidene)-5-fluoro-1,3-dihydro-indol-2-one A solution of 5-fluoro-1,3-dihydro-indol-2-one (2.88 g, 19.1 mmol.) in THF (20 mL) is cooled to 0° C. under an argon atmosphere and treated with a solution of lithium bis(trimethylsilyl)amide (38 mL of a 1 M solution in THF, 38.0 mmol) dropwise. The resulting solution is stirred at 0° C. for 10 min and warmed room temperature. A solution of 6,7-dichloro-1-propyl-1H-furo[3,4-c]pyridin-3-one, (3.13 g, 12.72 mmol) in THF (20 mL) is added dropwise to the reaction mixture. The resulting solution is stirred for 4 h. The reaction mixture is poured into aqueous 10% HCl solution (350 mL). The resulting mixture is heated to 90° C. for 2 h and then stirred at room temperature for 36 h. The precipitate which formed is collected by filtration and washed with small volumes of ethyl acetate (10×3 mL) to give the title compound as a yellow solid (1.75 g, 36%).

Example 56

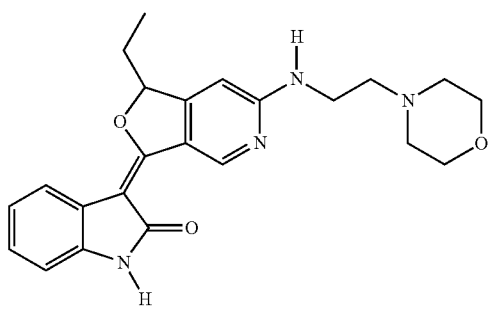 [SMILES: CCC1O/C(=C2/C(=O)Nc3ccccc32)c2cnc(NCCN3CCOCC3)cc21]

3-[1-Ethyl-6-(2-morpholin-4-yl-ethylamino)-1H-furo[3,4-c]pyridin-3-ylidene]-1,3-dihydro-indol-2-one A solution of 2-morpholin-4-yl-ethylamine (320 mg, 2.46 mmol) in 3 mL of dioxane is treated with 3-(6,7-Dichloro-1-ethyl-1H-furo[3,4-c]pyridin-3-ylidene)-1,3-dihydro-indol-2-one (100 mg, 0.32 mmol) in one portion and the reaction mixture is heated at 100° C. until no starting material remains. The reaction mixture is cooled to room temperature and concentrated. The residue is purified by chromatography (silica gel, 5% MeOH-EtOAc) to give the title compound as a solid (36 mg, 28%).

Example 57

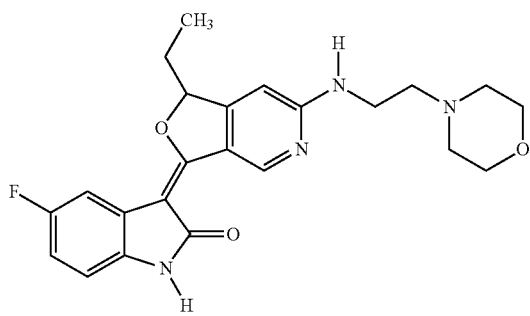 [SMILES: CCC1O/C(=C2/C(=O)Nc3ccc(F)cc32)c2cnc(NCCN3CCOCC3)cc21]

3-[1-Ethyl-6-(2-morpholin-4-yl-ethylamino)-1H-furo[3,4-c]pyridin-3-ylidene]-5-fluoro-1,3-dihydro-indol-2-one A solution of 2-morpholin-4-yl-ethylamine (177 mg, 1.51 mmol) in 3 mL of dioxane is treated with 3-(6-Chloro-1-ethyl-1H-furo[3,4-c]pyridin-3-ylidene)-5-fluoro-1,3-dihydro-indol-2-one (100 mg, 0.30 mmol) in one portion. The reaction mixture is heated at 100° C. until no starting material remained. The reaction mixture is treated with water (10 mL) and heating is continued for 1 hr. The precipitate which formed is collected by filtration and washed with small amounts of water, EtOAc and ether. The solid obtained is dried under vacuum to give the title compound as a yellow solid (18 mg, 14%).

Example 58

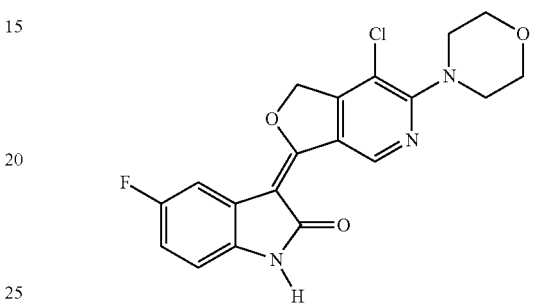

3-(7-Chloro-6-morpholin-4-yl-1H-furo[3,4-c]pyridin-3-ylidene)-5-fluoro-1,3-dihydro-indol-2-one A solution of morpholine (137 mg, 2.0 mmol) in 2 mL of dioxane is treated with 3-(6,7-dichloro-1H-furo[3,4-c]pyridin-3-ylidene)-1,3-dihydro-indol-2-one (100 mg, 0.27 mmol) in one portion and the reaction mixture is heated at 100° C. until no starting material remained. The reaction mixture is cooled to room temperature and concentrated. The residue is purified by chromatography (silica gel, 5% MeOH-EtOAc). The product containing fractions are concentrated to give the title compound as a solid (16 mg, 15%).

Example 59

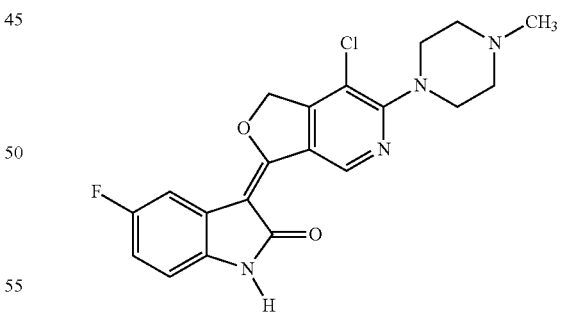

3-[7-Chloro-6-(4-methyl-piperazin-1-yl)-1H-furo[3,4-c]pyridin-3-ylidene]-5-fluoro-1,3-dihydro-indol-2-one A solution of N-methylpiperazine (137 mg, 1.37 mmol) in 3 mL of dioxane is treated with 3-(6,7-dichloro-1-ethyl-1H-furo[3,4-c]pyridin-3-ylidene)-1,3-dihydro-indol-2-one (100 mg, 0.27 mmol) in one portion and the reaction mixture is heated at 100° C. until no starting material remained. The

Example 60

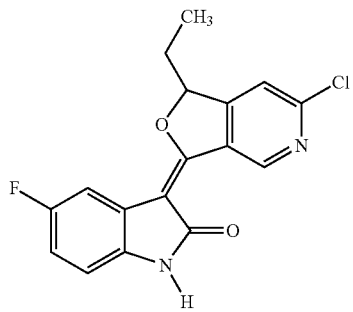 [SMILES: CCC1O/C(=C2/C(=O)Nc3ccc(F)cc32)c2cnc(Cl)cc21]

3-(6-Chloro-1-ethyl-1H-furo[3,4-c]pyridin-3-ylidene)-5-fluoro-1,3-dihydro-indol-2-one A solution of 5-fluoro-1,3-dihydro-indol-2-one (4.71 g, 31.2 mmol.) in THF (30 mL) is cooled to 0° C. under an argon atmosphere and treated with a solution of lithium bis(trimethylsilyl)amide (60 mL of a 1 M solution in THF, 60.0 mmol) dropwise. The resulting solution is stirred at 0° C. for 10 min and warmed room temperature. A solution of 6-chloro-1-ethyl-1H-furo[3,4-c]pyridin-3-one, (4.11 g, 20.8 mmol) in THF (30 mL) is added dropwise to the reaction mixture. The resulting solution is stirred for 4 h. The reaction mixture is poured into aqueous 10% HCl solution (350 mL). The resulting mixture is heated to 90° C. for 2 h and then stirred at room temperature for 36 h. The precipitate which forms is collected by filtration and washed with small volumes of ethyl acetate (10×3 mL) and dried to give the title compound as a yellow solid (2.37 g, 34%).

Example 61

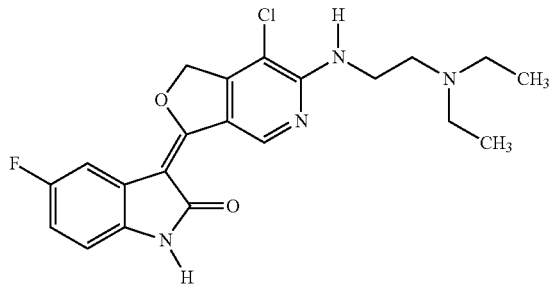 [SMILES: CCN(CC)CCNc1ncc2c(c1Cl)CO/C2=C1/C(=O)Nc2ccc(F)cc21]

3-[7-Chloro-6-(2-diethylamino-ethylamino)-1H-furo[3,4-c]pyridin-3-ylidene]-5-fluoro-1,3-dihydro-indol-2-one A solution of amine (320 mg, 3.40 mmol) in 3 mL of dioxane is treated with 3-(6,7-dichloro-1-ethyl-1H-furo[3,4-c]pyridin-3-ylidene)-1,3-dihydro-indol-2-one (100 mg, 0.27 mmol) in one portion and the reaction mixture is heated at 100° C. until no starting material remained. Water (10-12 mL) is added and the resulting solution is heated at 100° C. for 1 h during which time a precipitate is formed. The reaction mixture is cooled to room temperature and the solid which precipitated from solution is collected by filtration, washed and dried under vacuum to give the title compound as a solid (41 mg, 70%).

Example 62

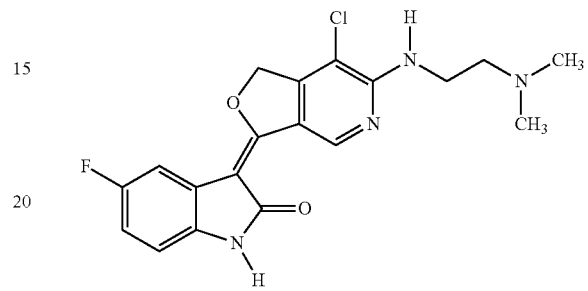

3-[7-Chloro-6-(2-dimethylamino-ethylamino)-1H-furo[3,4-c]pyridin-3-ylidene]-5-fluoro-1,3-dihydro-indol-2-one A solution of 2-dimethylamino-ethylamine (300 mg, 2.80 mmol) in 3 mL of dioxane is treated with 3-(6,7-dichloro-1H-furo[3,4-c]pyridin-3-ylidene)-1,3-dihydro-indol-2-one (100 mg, 0.27 mmol) in one portion and the reaction mixture is heated at 100° C. until no starting material remained. The reaction mixture is treated with water (10-12 mL) and heated at reflux for 1 h. The precipitate which formed is collected by filtration and washed sequentially with water, ethyl acetate and ether. The solid obtained is dried under vacuum to give the title compound as a solid (73 mg, 70%).

Example 63

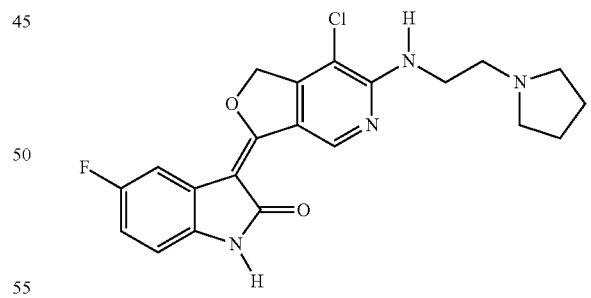

3-[7-Chloro-6-(2-pyrrolidin-1-yl-ethylamino)-1H-furo[3,4-c]pyridin-3-ylidene]-5-fluoro-1,3-dihydro-indol-2-one A solution of 2-pyrrolidin-1-yl-ethylamine (320 mg, 2.8 mmol) in 3 mL of dioxane is treated with 3-(6,7-dichloro-1H-furo[3,4-c]pyridin-3-ylidene)-1,3-dihydro-indol-2-one (100 mg, 0.27 mmol) in one portion and the reaction mixture is heated at 100° C. until no starting material remains. The reaction mixture is treated with water (10-12 mL) and heated at reflux for 1 h. The precipitate which forms is collected by filtration and washed sequentially with water ethyl acetate and ether. The solid obtained is dried to give the title compound as a solid (30 mg, 27%).

Example 64

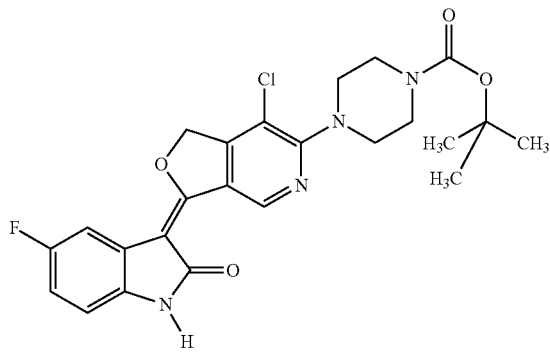 [SMILES: CC(C)(C)OC(=O)N1CCN(c2ncc3c(c2Cl)CO/C3=C2/C(=O)Nc3ccc(F)cc32)CC1]

4-[7-Chloro-3-(5-fluoro-2-oxo-1,2-dihydro-indol-3-ylidene)-1,3-dihydro-furo[3,4-c]pyridin-6-yl]-piperazine-1-carboxylic acid tert-butyl ester A solution of piperazine-1-carboxylic acid tert-butyl ester (450 mg, 2.42 mmol) in 3 mL of dioxane is treated with 3-(6,7-dichloro-1H-furo[3,4-c]pyridin-3-ylidene)-1,3-dihydro-indol-2-one (100 mg, 0.27 mmol) in one portion and the reaction mixture is heated at 100° C. until no starting material remains. The reaction mixture is treated with water (10-12 mL) and heated at reflux for 1 h. The precipitate which formed is collected by filtration and washed sequentially with water ethyl acetate and ether. The solid obtained is dried to give the title compound as a solid (82 mg, 62%).

Example 65

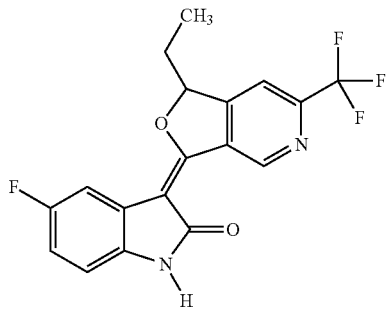 [SMILES: CCC1O/C(=C2/C(=O)Nc3ccc(F)cc32)c2cnc(C(F)(F)F)cc21]

3-(1-Ethyl-6-trifluoromethyl-1H-furo[3,4-c]pyridin-3-ylidene)-5-fluoro-1,3-dihydro-indol-2-one A solution of 5-fluoro-1,3-dihydro-indol-2-one (99 mg, 0.66 mmol.) in THF (2 mL) is cooled to 0° C. under an Argon atmosphere and treated with a solution of lithium bis(trimethylsilyl)amide (1.3 mL of a 1 M solution in THF, 1.3 mmol) dropwise. The resulting solution is stirred at 0° C. for 10 min and warmed to room temperature. A solution of 1-ethyl-6-trifluoromethyl-1H-furo[3,4-c]pyridin-3-one, (100 mg, 0.44 mmol) in THF (2 mL) is added dropwise to the reaction mixture. The resulting solution is stirred for 4 h. The reaction mixture is poured into aqueous 10% HCl solution (50 mL). The resulting mixture is heated to 90° C. for 45 min and then stirred at room temperature for 36 h. The precipitate which formed is collected by filtration and dried. The solid obtained is purified by chromatography (silica gel, 40% EtOAc/hexane). The product containing fractions are concentrated to give the title compound as a yellow solid (30 mg, 19%).

Example 66

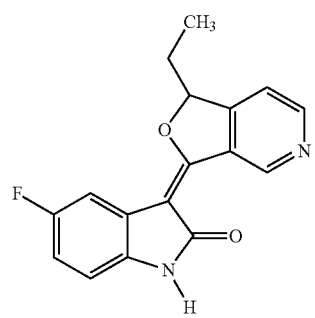 [SMILES: CCC1O/C(=C2/C(=O)Nc3ccc(F)cc32)c2cnccc21]

3-(1-Ethyl-1H-furo[3,4-c]pyridin-3-ylidene)-5-fluoro-1,3-dihydro-indol-2-one

A solution of 3-(6-Chloro-1-ethyl-1H-furo[3,4-c]pyridin-3-ylidene)-5-fluoro-1,3-dihydro-indol-2-one (50 mg, 0.15 mmol) in 8 ml ethanol is treated with 50 mg of 5% Pd/C and ammonium formate (500 mg). The reaction mixture is stirred for 24 h at room temperature. The reaction mixture is concentrated and is then loaded onto silica gel and purified using 5% MeOH-EtOAc. The product containing fractions are concentrated to give the title compound (18 mg, 40%).

Preparation 34

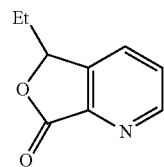 [SMILES: CCC1OC(=O)c2ncccc21]

5-Ethyl-5H-furo[3,4-b]pyridin-7-one

A solution of 2,2,6,6-tetramethyl-piperidine (20.3 ml, 120 mmol) in a 250 ml round bottomed flask equipped with a magnetic stirrer, is put under argon atmosphere and 60 ml of dry THF is added. The reaction mixture is cooled to −78° C. The cooled reaction mixture is treated dropwise with nBuLi solution (64 mL of a 2.5 M solution in hexanes, 160 mmol) and the reaction is let stir at −78° C. for 5 min. A solution of picolinic acid (4.92 g, 40 mmol) in THF (60 mL) is added dropwise to the reaction at −78° C. The reaction is stirred at −78° C. for 1 h and is then warmed to −20° C. for 30 min. The reaction mixture is treated with propionaldehyde (7.2 ml, 100 mmol, 2.5 eq) dropwise at −50° C. The reaction is stirred at −20° C. for 2 h and warmed to room temperature overnight.

The reaction mixture is concentrated and the residue is dissolved in water and ether. The aqueous layer is collected and extracted with dichloromethane and ether (6×50 ml). The aqueous phase is concentrated and the residue is dissolved in EtOH (30 mL) and acetic acid (2 mL) and heated at reflux overnight under argon. The reaction mixture is cooled to room temperature and concentrated. The residue is purified by chromatography (silica gel) to give the title compound (0.70 g, 11%).

Example 67

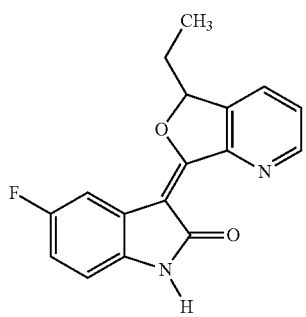 [SMILES: CCC1O/C(=C2/C(=O)Nc3ccc(F)cc32)c2ncccc21]

3-(5-Ethyl-5H-furo[3,4-b]pyridin-7-ylidene)-5-fluoro-1,3-dihydro-indol-2-one

A solution of 5-fluoro-1,3-dihydro-indol-2-one (966 mg, 6.4 mmol.) in THF (6 mL) is cooled to 0° C. under an Argon atmosphere and treated with a solution of lithium bis(trimethylsilyl)amide (12.8 mL of a 1 M solution in THF, 12.8 mmol) dropwise. The resulting solution is stirred at 0° C. for 10 min and warmed to room temperature. A solution of 5-ethyl-5H-furo[3,4-b]pyridin-7-one, (697 mg, 4.27 mmol) in THF (7 mL) is added dropwise to the reaction mixture. The resulting solution is stirred for 4 h. The reaction mixture is poured into aqueous 10% HCl solution (160 mL). The resulting mixture is heated to 90° C. for 45 min and stirred at room temperature for 36 h. The precipitate which formed is collected by filtration washed with small volumes of ethyl acetate (10×3 mL) and dried to give the title compound as a yellow solid (205 mg, 16%).

Preparation 35

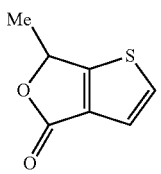

6-Methyl-6H-thieno[2,3-c]furan-4-one

A solution of thiophene-3-carboxylic acid (1.00 g, 7.8 mmol) in THF (10 mL) is added dropwise to a cold (−80° C.) solution of lithium bistrimethylsilylamide (8.6 mL of a 2M solution) in THF (15 mL). The resulting pale yellow solution is warmed to −50° C. and is stirred at −50° C. for 1 hr during which time a white precipitate is formed. The reaction mixture is cooled to −80° C. and treated dropwise with acetaldehyde (1.2 mL). The white precipitate gradually disappeared during the addition. The reaction mixture is warmed to −20° C. and stirred for 30 min. The reaction mixture is then poured into aqueous 2M HCl solution (120 mL). The resulting mixture is stirred at room temperature while a stream of air is blown into the reaction vessel to assist in the evaporation of THF. The white precipitate which forms is collected by filtration and dissolved in dichloromethane (5 mL) and Et₃N (5 mL). The reaction mixture is treated with p-toluenesulfonyl chloride (0.38 g, 2.0 mmol) and stirred overnight. The reaction mixture is treated with NaHCO₃ solution and the organic phase is collected, dried over Na₂SO₄, filtered and concentrated. The residue is purified by chromatography (silica gel) to give the title compound (0.39 g, 32%).

Example 68

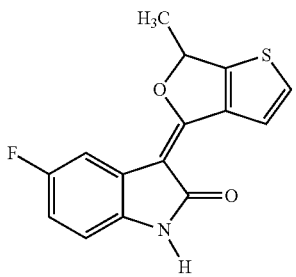 [SMILES: CC1O/C(=C2/C(=O)Nc3ccc(F)cc32)c2ccsc21]

5-Fluoro-3-(6-methyl-6H-thieno[2,3-c]furan-4-ylidene)-1,3-dihydro-indol-2-one

A solution of 5-fluoro-1,3-dihydro-indol-2-one (453 mg, 3.0 mmol.) in THF (3 mL) is cooled to 0° C. under an Argon atmosphere and treated with a solution of lithium bis(trimethylsilyl)amide (6.0 mL of a 1 M solution in THF, 6.0 mmol) dropwise. The resulting solution is stirred at 0° C. for 10 min and warmed to room temperature. A solution of 6-ethyl-6H-thieno[2,3-c]furan-4-one, (310 mg, 2.0 mmol) in THF (5 mL) is added dropwise to the reaction mixture. The resulting solution is stirred for 4 h. The reaction mixture is poured into aqueous 10% HCl solution (50 mL). The resulting mixture is heated to 90° C. for 45 min and stirred at room temperature for 36 h. The precipitate which formed is collected by filtration and dried. The solid obtained is purified by chromatography (silica gel, ethyl acetate/hexanes) to give the title compound as a yellow solid.

Preparation 36

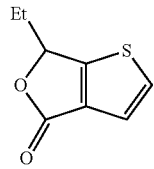 [SMILES: CCC1OC(=O)c2ccsc21]

6-Ethyl-6H-thieno[2,3-c]furan-4-one

A solution of thiophene-3-carboxylic acid (1.00 g, 7.8 mmol) in THF (10 mL) is added dropwise to a cold (−80° C.)

solution of lithium bistrimethylsilylamide (8.6 mL of a 2M solution in solvent) in THF (15 mL). The resulting pale yellow solution is warmed to −50° C. and is stirred at −50° C. for 1 hr during which time a white precipitate is formed. The reaction mixture is cooled to −80° C. and treated dropwise with propionaldehyde (1.2 mL, 16.6 mmol). The reaction mixture is warmed to −20° C. and stirred for 30 min. The reaction mixture is then poured into aqueous 2M HCl solution (120 mL). The resulting suspension is stirred at room temperature while a stream of air is blown into the reaction vessel to assist in the evaporation of THF. The white precipitate which forms is collected by filtration and dissolved in Dichloromethane (5 mL) and Et$_3$N (5 mL). The reaction mixture is treated with p-toluenesulfonyl chloride (0.38 g, 2.0 mmol) and stirred overnight. The reaction mixture is treated with NaHCO$_3$ solution and the organic phase is collected, dried over Na$_2$SO$_4$, filtered and concentrated to give the title compound (0.33 g, 25%).

Example 69

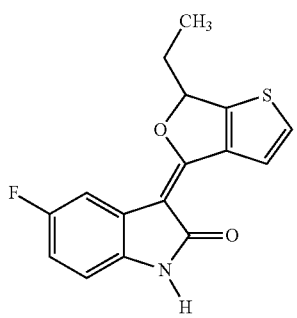 [SMILES: CCC1O/C(=C2/C(=O)Nc3ccc(F)cc32)c2ccsc21]

3-(6-Ethyl-6H-thieno[2,3-c]furan-4-ylidene)-5-fluoro-1,3-dihydro-indol-2-one

A solution of 5-fluoro-1,3-dihydro-indol-2-one (440 mg, 2.9 mmol.) in THF (3 mL) is cooled to 0° C. under an Argon atmosphere and treated with a solution of lithium bis(trimethylsilyl)amide (5.8 mL of a 1 M solution in THF, 5.8 mmol) dropwise. The resulting solution is stirred at 0° C. for 10 min and warmed to room temperature. A solution of 6-ethyl-6H-thieno[2,3-c]furan-4-one, (328 mg, 1.94 mmol) in THF (4 mL) and added dropwise to the reaction mixture. The resulting solution is stirred for 4 h. The reaction mixture is poured into aqueous 10% HCl solution (100 mL). The resulting mixture is heated to 90° C. for 45 min and stirred at room temperature for 36 h. The precipitate which formed is collected by filtration and dried. The solid obtained is purified by chromatography (30% EtOAc/hexane). The product containing fractions are concentrated to give the title compound as a yellow solid (190 mg, 33%).

Preparation 37

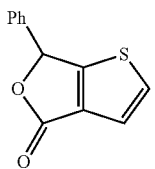

6-Phenyl-6H-thieno[2,3-c]furan-4-one

A solution of thiophene-3-carboxylic acid (2.00 g, 15.6 mmol) in THF (20 mL) is added dropwise to a cold (−80° C.) solution of lithium bistrimethylsilylamide (17.2 mL of a 2M solution 34 mmol) in THF (30 mL). The resulting pale yellow solution is warmed to −50° C. and is stirred at −50° C. for 1 hr during which time a white precipitate is formed. The reaction mixture is cooled to −80° C. and treated dropwise with benzaldehyde (3.0 mL). The white precipitate gradually disappeared during the addition. The reaction mixture is warmed to −20° C. and stirred for 30 min. The reaction mixture is then poured into aqueous 2M HCl solution (120 mL). The resulting mixture is stirred at room temperature while a stream of air is blown into the reaction vessel to assist in the evaporation of THF. The white precipitate which forms is collected by filtration and dissolved in Dichloromethane (20 mL) and Et$_3$N (12 mL). The reaction mixture is treated with TsCl (3.42 g, 17.2 mmol) and stirred overnight. The reaction mixture is treated with NaHCO$_3$ solution and the organic phase is collected, dried over Na$_2$SO$_4$, filtered and concentrated. The residue is purified by chromatography (silica gel, 10% ethylacetate/hexane) to give the title compound (0.39 g, 12%).

Example 70

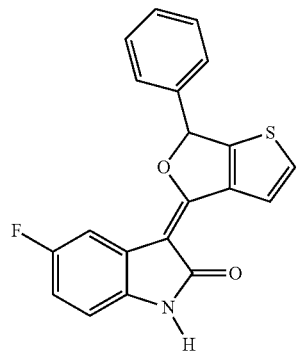 [SMILES: O=C1Nc2ccc(F)cc2/C1=C1\OC(c2ccccc2)c2sccc21]

5-Fluoro-3-(6-phenyl-6H-thieno[2,3-c]furan-4-ylidene)-1,3-dihydro-indol-2-one

A solution of 5-fluoro-1,3-dihydro-indol-2-one (340 mg, 2.25 mmol.) in THF (3 mL) is cooled to 0° C. under an Argon atmosphere and treated with a solution of lithium bis(trimethylsilyl)amide (4.5 mL of a 1 M solution in THF, 4.5 mmol) dropwise. The resulting solution is stirred at 0° C. for 10 min and then warmed to room temperature. A solution of 6-phenyl-6H-thieno[2,3-c]furan-4-one, (320 mg, 1.5 mmol) in THF (6 mL) is added dropwise to the reaction mixture. The resulting solution is stirred for 4 h. and then poured into aqueous 10% HCl solution (50 mL). The resulting mixture is heated to 90° C. for 45 min and stirred at room temperature for 36 h. The precipitate which formed is collected by filtration and dried. The solid obtained is purified by chromatography (silica gel, ethyl acetate/hexane) to give the title compound as a yellow solid (15 mg, 3%).

Preparation 38

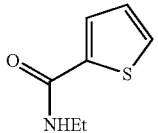

Thiophene-2-carboxylic acid ethylamide

Neat thiophene-2-carbonyl chloride (1.46 g, 10 mmol) is added dropwise to a solution of ethylamine (70% wt/water) in Dichloromethane (8 mL) and Et₃N at 0° C. Additional ethylamine (2.5 ml, 70% wt/water) is added to the reaction mixture and the reaction is stirred at 0° C. for 2 hrs and the warmed to room temperature for 2 h. The reaction mixture is transferred to a separatory funnel and the organic layer is washed sequentially with aqueous 1N HCl solution, water and saturated aqueous NaHCO₃ solution. The organic phase is collected, dried over Na₂SO₄, filtered and concentrated to give the title compound (1.4 g, 90%).

Preparation 39

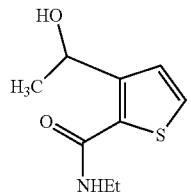

3-Hydroxymethyl-thiophene-2-carboxylic acid ethylamide

A solution of thiophene-2-carboxylic acid ethylamide (465 mg, 3 mmol) in dry THF (12 mL) is cooled to −78° C. under an argon atmosphere. Tert-BuLi (5.3 mL of a 1.7 M solution in pentane, 9.0 mmol) is added dropwise at −78° C. and the reaction mixture is stirred for 3 h. The reaction mixture is treated with neat acetaldehyde (3 mL, 53 mmol) and is stirred at −78° C. for 2 h and then warmed to room temperature overnight. The reaction mixture is quenched by the addition of water (35 mL). The reaction mixture is transferred to a separatory funnel and the organic phase is collected. The aqueous layer is extracted 5 times with Dichloromethane. The combined organic extracts are washed with water, and saturated aqueous NaCl, dried over Na₂SO₄ and concentrated. The residue is purified by chromatography (silica gel, 25% EtOAc/hexane) to give the title compound (298 mg, 15 mmol) in 50% yield.

Preparation 40

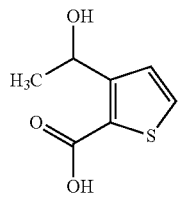

3-Hydroxymethyl-thiophene-2-carboxylic acid

A solution of 3-(1-Hydroxy-ethyl)-thiophene-2-carboxylic acid ethylamide (298 mg, 1.5 mmol) in 15 ml of aqueous 6N HCl solution is heated at 100° C. for 1.5 h. The reaction mixture is cooled to room temperature and the pH is adjusted to ~8.5 with 30% aqueous NaOH solution and saturated aqueous sodium bicarbonate solution. The resulting solution is extracted with Dichloromethane. The aqueous layer is collected and acidified with aqueous 6N HCl until the pH ~1. The resulting solution is extracted with tBuOH-Ether. The combined organic extracts are dried and concentrated to give the title compound (25 mg, 10%).

Preparation 41

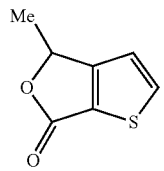

4H-Thieno[2,3-c]furan-6-one

A solution of 3-hydroxymethyl-thiophene-2-carboxylic acid (25 mg, 0.15 mmol) in dichloromethane (4 ml) and triethylamide (1.5 mL) is treated with p-toluenesulfonyl chloride (50 mg, 0.26 mmol) and the reaction mixture is stirred at room temperature overnight. The reaction mixture is concentrated and the product is purified by chromatography (silica gel, ethylacetate/hexane) to give the title compound. This material was used directly in the preparation of Example 70.

Example 71

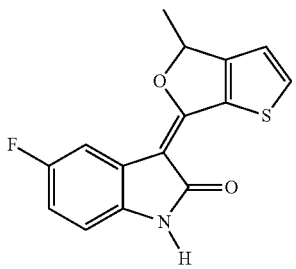 [SMILES: CC1O/C(=C2/C(=O)Nc3ccc(F)cc32)c2sccc21]

5-Fluoro-3-(4-methyl-4H-thieno[2,3-c]furan-6-ylidene)-1,3-dihydro-indol-2-one A solution of 5-fluoro-1,3-dihydro-indol-2-one in THF is cooled to 0° C. under an argon atmosphere and treated with a solution of lithium bis(trimethylsilyl)amide dropwise. The resulting solution is stirred at 0° C. for 10 min and warmed room temperature. A solution of 4-methyl-4H-thieno[2,3-c]furan-6-one (0.15 mmol), in THF is added dropwise to the reaction mixture. The resulting solution is stirred for 4 h. The reaction mixture is poured into aqueous 10% HCl solution. The resulting mixture is heated to 90° C. for 45 min and stirred at room temperature for 36 h. The precipitate which formed is collected by filtration and dried. The solid obtained is purified by chromatography (35% EtOAc-Hexanes) to give the title compound as a yellow solid (38 mg, 87%).

Preparation 42

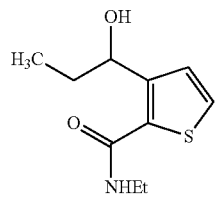

3-(1-hydroxy-propyl)-thiophene-2-carboxylic acid ethylamide

Following the method described in Preparation 39, thiophene-2-carboxylic acid ethylamide (3 mmol) is converted to the title compound.

Preparation 43

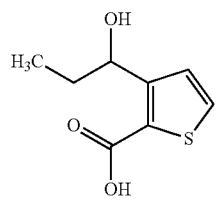

3-(1-Hydroxy-propyl)-thiophene-2-carboxylic acid

Following the method described in Preparation 40, 3-(1-hydroxy-propyl)-thiophene-2-carboxylic acid ethylamide is converted to the title compound.

Preparation 44

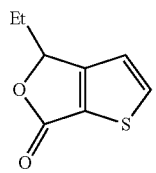

4-Ethyl-4H-thieno[2,3-c]furan-6-one

A solution of 3-(1-Hydroxy-propyl)-thiophene-2-carboxylic acid (25 mg) in Dichloromethane (4 ml) and triethylamide (1.5 mL) is treated with TsCl (50 mg) and reaction is stirred at room temperature overnight. The reaction mixture is concentrated and the product is purified by chromatography (silica gel, 20% ethyl acetate/hexane) to give the title compound (67 mg, 13% yield).

Example 72

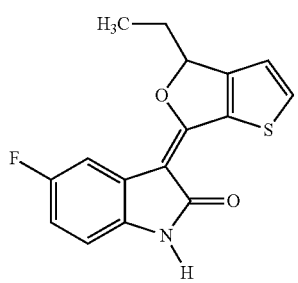 [SMILES: CCC1O/C(=C2/C(=O)Nc3ccc(F)cc32)c2sccc21]

3-(4-Ethyl-4H-thieno[2,3-c]furan-6-ylidene)-5-fluoro-1,3-dihydro-indol-2-one

A solution of 5-fluoro-1,3-dihydro-indol-2-one (91 mg, 0.6 mmol.) in THF (1 mL) is cooled to 0° C. under an Argon atmosphere and treated with a solution of lithium bis(trimethylsilyl)amide (1.2 mL of a 1 M solution in THF, 1.2 mmol) dropwise. The resulting solution is stirred at 0° C. for 10 min and warmed to room temperature. A solution of 4-ethyl-4H-thieno[2,3-c]furan-6-one, (67 mg, 0.4 mmol) in THF (1.5 mL) is added dropwise to the reaction mixture. The resulting solution is stirred for 4 h. The reaction mixture is poured into aqueous 10% HCl solution (50 mL). The resulting mixture is heated to 90° C. for 45 min and stirred at room temperature for 36 h. The precipitate which formed is collected by filtration and dried to give the title compound as a yellow solid (68 mg, 57%).

Example 73

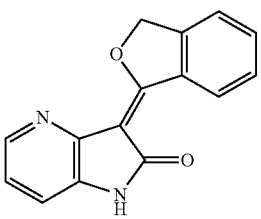 [SMILES: O=C1Nc2cccnc2/C1=C1\OCc2ccccc21]

3-(3H-Isobenzofuran-1-ylidene)-1,3-dihydro-pyrrolo[3,2-b]pyridin-2-one

To a solution of 1,3-dihydro-pyrrolo[3,2-b]pyridin-2-one (50 mg, 0.37 mmol) in anhydrous N,N-dimethylformamide (5.0 ml) was added 1.0M LiHMDS/THF solution (0.74 ml, 0.74 mmol) under $N_2$. After the mixture was stirred at room temperature for 10 minutes, phthalide was added (40 mg, 0.30 mmol), and then it was continuously stirred at room temperature for 4 hours. The mixture was poured into 2M HCl (4.0 ml), heated at 50° C. for 20 minutes and then poured into water (100 ml). After cooled to room temperature, the mixture was basified to pH 9 with saturated $NaHCO_3$ solution, and was stirred at room temperature overnight. The resulting solid was filtered, washed with water, dried under vacuum and triturated with chloroform to give 3-(3H-isobenzofuran-1-ylidene)-1,3-dihydro-pyrrolo[3,2-b]pyridin-2-one as a yellow solid (12 mg, 16%).

$^1$H NMR (500 MHz, $d_6$-DMSO) δ ppm 5.84 (s, 2H) 7.05 (dd, J=7.32, 4.88 Hz, 1H) 7.11 (dd, J=7.81, 1.46 Hz, 1H) 7.58-7.63 (m, 1H) 7.70-7.73 (m, 2H) 8.13 (d, J=3.42 Hz, 1H) 9.75 (d, J=7.81 Hz, 1H) 10.53 (s, 1H)

Example 74

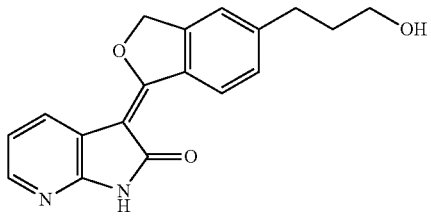 [SMILES: O=C1Nc2ncccc2/C1=C1\OCc2cc(CCCO)ccc21]

3-[5-(3-Hydroxy-propyl)-3H-isobenzofuran-1-ylidene]-1,3-dihydro-pyrrolo[2,3-b]pyridin-2-one To a stirred solution of 1,3-dihydro-pyrrolo[2,3-b]pyridin-2-one (193 mg (1.44 mmol) in anhydrous tetrahydrofuran (10 ml) under N2 was added 1.0M LiHMDS/THF solution (2.9 ml, 2.9 mmol). The mixture was stirred at room temperature for 10 minutes, then 5-[3-(tetrahydro-pyran-2-yloxy)-propyl]-3H-isobenzofuran-1-one (200 mg, 0.72 mmol) was added. The mixture was stirred at room temperature for 2.5 hours and poured into 1M $H_2SO_4$ solution (20 ml). The mixture was heated at 55° C. for 15 minutes, cooled to room temperature and poured into an ice water (200 ml). The mixture was basified to pH 9 with NaOH solution and stirred overnight. The solid was filtered, washed with water and dried under vacuum to give 3-[5-(3-hydroxy-propyl)-3H-isobenzofuran-1-ylidene]-1,3-dihydro-pyrrolo[2,3-b]pyridin-2-one as a brown solid (20 mg, 9%).

$^1$H NMR (500 MHz, $d_6$-DMSO) δ ppm 1.74-1.83 (m, 2H) 2.77 (t, J=7.81 Hz, 2H) 3.45 (q, J=5.37 Hz, 2H) 4.54 (t, J=5.13 Hz, 1H) 5.80 (s, 2H) 6.97 (dd, J=7.08, 5.13 Hz, 1H) 7.45 (d, J=7.81 Hz, 1H) 7.51 (s, 1H) 7.93-8.04 (m, 2H) 9.48 (d, J=8.30 Hz, 1H) 10.97 (s, 1H)

LR MS (EI): 308 (M+)

The present invention is not to be limited in scope by the exemplified embodiments which are intended as illustrations of single aspects of the invention only. Indeed, various modifications of the invention in addition to those described herein will become apparent to those skilled in the art from the foregoing description.

All references cited herein are hereby incorporated by reference in their entirety.

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof

What is claimed is:
1. A compound represented by the formula:

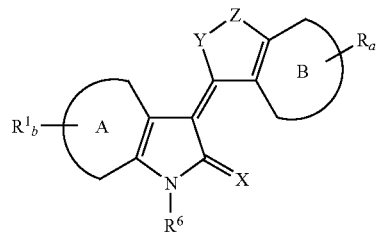

wherein:
X is O or S;
Y is O, S or $NR^3$;
Z is $[C(R^2)_2]_c$;
the ring system A is

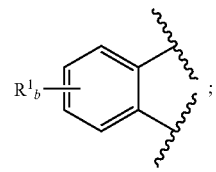

the ring system B represents a 5 membered aryl group and is selected from the group consisting of:

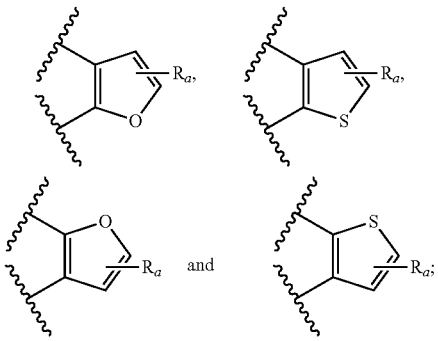

$R^1$ is selected from the group consisting of halogen, aryl, $C_1$ to $C_8$ alkyl, $CF_3$, $OCF_3$, $OCF_2H$, $S(O)_fR^2$, $(CR^3R^4)_d$ $C(O)OR^2$, $O(CR^3R^4)_eC(O)OR^2$, $NR^2$ $(CR^3R^4)_dC(O)R^2$, $NR^2(CR^3R^4)_dC(O)OR^2$, $OP(O)$ $(OR^2)_2$, $OC(O)OR^2$, $OCH_2O$, $NR^2(CH_2)_eN(R^2)_2$, $O(CH_2)_eN(R^2)_2$, $(CR^3R^4)_dCN$, $O(CR^3R^4)_eCN$, $(CR^3R^4)_dAr$, $NR^2(CR^3R^4)_dAr$, $O(CR^3R^4)_dAr$, $S(O)_f$ $(CR^3R^4)_dAr$, $(CR^3R^4)_dSO_2R^2$, $(CR^3R^4)_dC(O)N$ $(R^2)_2$, $NR^2(CR^3R^4)_dC(O)N(R^2)_2$, $O(CR^3R^4)_dC(O)N$ $(R^2)_2$, $S(O)_f$ $(CR^3R^4)_eC(O)N(R^2)_2$, $(CR^3R^4)_dOR^2$, $NR^2(CR^3R^4)_e$ $OR^2$, $O(CR^3R^4)_eOR^2$, $S(O)_f(CR^3R^4)_d$ $OR^2$, $C(O)(CR^3R^4)_dR^3$, $NR^2C(O)(CR^3R^4)_dR^3$, $OC(O)(CR^3R^4)_d$ $N(R^2)_2$, $C(O)(CR^3R^4)_dN(R^2)_2$, $NR^2C(O)(CR^3R^4)_d$ $N(R^2)_2$, $OC(O)(CR^3R^4)_dN(R^2)_2$, $(CR^3R^4)_dR^3$, $NR^2(CR^3R^4)_dR^3$, $O(CR^3R^4)_dR^3$, $S(O)_f$ $(CR^3R^4)_dR^3$, $(CR^3R^4)_dN(R^2)_2$, $NR^2(CR^3R^4)_e$ $N(R^2)_2$, $O(CR^3R^4)_e$ $N(R^2)_2$, $S(O)_f(CR^3R^4)_dN(R^2)_2$, $N(R^5)_2$, $OR^5$, $C(O)R^5$, $S(O)_fR^5$, $C(O)ArNR^2C(O)Ar$, $NR^2ArNR^2C(O)Ar$, $OArNR^2C(O)Ar$, $SArNR^2C(O)Ar$, $C(O)ArC(O)(NR^2)_2$, $OArC(O)(NR^2)_2$, $NR^2ArC(O)(NR^2)_2$, $SArC(O)(NR^2)_2C(O)ArC(O)NR^2Ar$, $OArC(O)NR^2Ar$, $NR^2ArC(O)NR^2Ar$ and $SArC(O)NR^2Ar$;

$R^2$ is selected from the group consisting of hydrogen, $C_1$ to $C_8$ alkyl, $C_1$ to $C_8$ alkenyl, $C_1$ to $C_8$ alkynyl, $C_1$ to $C_4$ alkylol, lower alkylphenyl, phenyl, $(CR^3R^4)_dAr$, $OC(O)R^7$, $(CR^3R^4)_dC(O)OR^7$, $(CR^3R^4)_dSO_2R^7$, $(CR^3R^4)_dSO_2N(R^7)_2$, $(CR^3R^4)_dOR^7$, $(CR^3R^4)_dOSO_2R^7$, $(CR^3R^4)_dP(O)(OR^7)_2$, $(CR^3R^4)_dR^7$, $(CR^3R^4)_eN(R^7)_2$ and $(CR^3R^4)_eNR^7C(O)N(R^7)_2$ wherein $N(R^2)_2$ and $N(R^7)_2$ may form a 3-7 membered heterocyclic ring and $[C(R^2)_2]_c$ may form a 3-7 membered carbocyclic or heterocyclic ring, wherein said heterocyclic ring may be substituted with one or more of $R^3$;

R is selected from the group consisting of halogen, $C_1$ to $C_8$ alkyl, $CF_3$, $OCF_3$, $OCF_2H$, $(CR^3R^4)_dCN$, $NR^2(CR^3R^4)_eCN$, $O(CR^3R^4)_eCN$, $S(O)_fR^2$, $(CR^3R^4)_dC(O)OR^2$, $(CR^3R^4)_dC(O)R^2$, $(CR^3R^4)_dC(OR^2)_2$, $NR^2(CR^3R^4)_dC(O)OR^2$, $O(CR^3R^4)_dC(O)OR^2$, $S(O)_f(CR^3R^4)_dC(O)OR^2$, $(CR^3R^4)_dAr$, $NR^2(CR^3R^4)_dAr$, $O(CR^3R^4)_dAr$, $S(O)_f(CR^3R^4)_dAr$, $(CR^3R^4)_dSO_2R^2$, $NR^2(CR^3R^4)_dS(O)_fR^2$, $O(CR^3R^4)_dS(O)_fR^2$, $S(O)_f(CR^3R^4)_eS(O)_fR^2$, $(CR^3R^4)_dC(O)N(R^2)_2$, $NR^2(CR^3R^4)_dC(O)N(R^2)_2$, $O(CR^3R^4)_dC(O)N(R^2)_2$, $S(O)_f(CR^3R^4)_eC(O)N(R^2)_2$, $(CR^3R^4)_dOR^2$, $NR^2(CR^3R^4)_eOR^2$, $O(CR^3R^4)_eOR^2$, $S(O)_f(CR^3R^4)_dOR^2$, $(CR^3R^4)_dOSO_2R^2$, $NR^2(CR^3R^4)_eOSO_2R^2$, $O(CR^3R^4)_eOSO_2R^2$, $S(O)_f(CR^3R^4)_eOSO_2R^2$, $(CR^3R^4)_dP(O)(OR^2)_2$, $NR^2(CR^3R^4)_dP(O)(OR^2)_2$, $O(CR^3R^4)_dP(O)(OR^2)_2$, $S(O)_f(CR^3R^4)_eP(O)(OR^2)_2$, $C(O)(CR^3R^4)_d R^3$, $NR^2C(O)(CR^3R^4)_dR^3$, $OC(O)(CR^3R^4)_dN(R^2)_2$, $C(O)(CR^3R^4)_dN(R^2)_2$, $C(O)NR^2(CR^3R^4)_eN(R^2)_2$, $NR^2C(O)(CR^3R^4)_dN(R^2)_2$, $OC(O)(CR^3R^4)_dN(R^2)_2$, $(CR^3R^4)_dR^3$, $NR^2(CR^3R^4)_dR^3$, $O(CR^3R^4)_dR^3$, $S(O)_f(CR^3R^4)_dR^3$, $HNC(O)R^2$, $HN-C(O)OR^2$, $(CR^3R^4)_d N(R^2)_2$, $NR^2(CR^3R^4)_eN(R^2)_2$, $O(CR^3R^4)_eN(R^2)_2$, $S(O)_f(CR^3R^4)_dN(R^2)_2$, $OP(O)(OR^2)_2$, $OC(O)OR^2$, $OCH_2O$, $HN-CH=CH$, $-N(COR^2)CH_2CH_2$, $HC=N-NH$, $N=CH-S$, $(CR^3R^4)_dC=C(CR^3R^4)_d R^2$, $(CR^3R^4)_dC=C(CR^3R^4)_dOR^2$, $(CR^3R^4)_dC=C(CR^3R^4)_dN(R^2)_2$, $(CR^3R^4)_dCC(CR^3R^4)_dR^2$, $(CR^3R^4)_d CC(CR^3R^4)_eOR^2$, $(CR^3R^4)_dCC(CR^3R^4)_eN(R^2)_2$, $(CR^3R^4)_dC(O)(CR^3R^4)_dR^2$, $(CR^3R^4)_dC(O)(CR^3R^4)_d OR^2$ and $(CR^3R^4)_dC(O)(CR^3R^4)_dN(R^2)_2$ and $(CR^3R^4)_dR^5$;

$R^3$ and $R^4$ may be selected from the group consisting of H, F, hydroxy, $C_1$-$C_4$ alkyl, $(CR^8R^9)_dOR^8$, $(CR^8R^9)_dO(CR^8R^9)_eOR^8$, $(CR^8R^9)_dCOOR^8$ and $(CR^8R^9)_dN(R^8)_2$ or $CR^3R^4$ may represent a carbocyclic or heterocyclic ring of from 3 to 6 carbons or, alternatively, $(CR^3R^4)_d$ and $(CR^3R^4)_e$ may form a 3-7 membered carbocyclic or heterocyclic ring;

$R^5$ is an aryl group or a substituted oxindole;

$R^6$ is selected from the group consisting of hydrogen, $C_1$-$C_8$ alkyl, hydroxymethyl and phenyl;

$R^7$ is selected from the group consisting of hydrogen, hydroxyl, F, $C_1$ to $C_8$ alkyl, $C_2$ to $C_8$ alkenyl, $C_2$ to $C_8$ alkynyl, $C_1$ to $C_4$ alkylol, lower alkylphenyl and phenyl;

$R^8$ and $R^9$ are selected from the group consisting of hydrogen, hydroxyl, F, $C_2$ to $C_8$ alkyl, $C_2$ to $C_8$ alkenyl, $C_2$ to $C_8$ alkynyl, $C_1$ to $C_4$ alkylol, lower alkylphenyl and phenyl;

a is 0 or an integer of from 1 to 3;
b is 0 or an integer of from 1 to 2;
c is an integer of from 1 to 2;
d is 0 or an integer of from 1 to 5;
e is an integer of from 1 to 4;
f is 0 or an integer of from 1 to 2, and further provided any of said alkyl or aryl radicals may be substituted with one or two halo, hydroxy, lower alkyloxy or lower alkyl amino radicals, including cycloalkylamino radicals and wherein the alkyl, or the cycloalkyl amino ring, can include an enchained oxygen, sulfur or additional nitrogen atom and may be substituted with one or two halo or lower alkyl radicals;

or a pharmaceutically acceptable salts thereof.

2. The compound of claim 1 wherein Y is O.
3. The compound of claim 1 wherein X is O.
4. The compound of claim 1 wherein X is O and Y is O.
5. The compound of claim 1 wherein b is 0 or b is 1 and $R^1$ is F.
6. The compound of claim 4 wherein $R^6$ is H.
7. The compound of claim 6 wherein A is

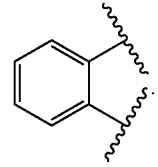 [SMILES: *c1ccccc1*]

8. The compound of claim 7 wherein B is selected from the group consisting of

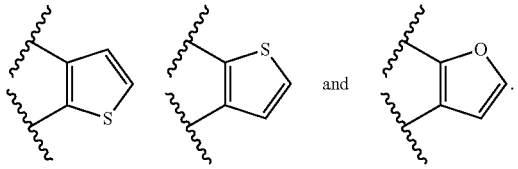 [SMILES: *c1ccsc1* ; *c1ccsc1* ; *c1ccoc1*]

9. The compound of claim 5 wherein c is 1.
10. The compound of claim 9 wherein one of $R^2$ is hydrogen and the other $R^2$ is selected from the group consisting of hydrogen, methyl, ethyl, n-propyl, i-propyl and phenyl, $CH_2COOH$, $CH_2SO_2CH_3$, $CH_2SO_2N(R^2)_2$.
11. The compound of claim 5 wherein a is 0 or a is 1 or 2 and is selected from the group consisting of halogen, lower alkyl, lower alkenyl, lower alkylether and amino lower alkyl groups.
12. The compound of claim 11 wherein R is a amino lower alkyl group and said amino lower alkyl group comprises from 1 to 3 enchained nitrogen atoms and from 0 to 2 enchained oxygen atoms and wherein one or more of the hydrogen atoms in said lower alkyl may be substituted with a hydroxyl, keto or carboxy group.
13. The compound of claim 11 where R is a lower alkyl ether group comprising from 1 to 3 enchained oxygen atoms and wherein one or more of the hydrogen atoms in said lower alkyl may be substituted with a hydroxyl, keto or carboxy group.
14. The compound of claim 12 wherein said amino lower alkyl group is selected from the group consisting of 2-morpholin-4-ylmethyl, 2-(2-morpholin-4-yl-ethyl), 3-(4-hydroxy-piperidin-1-yl)-propyl, 3-Diethylamino-propyl, 2-(3-{4-[2-hydroxy-ethoxy)-ethyl]-piperazin-1-yl}-propyl, 2-[3-(3-hydroxy-piperidin-1-yl)-propyl, 3-[2-methoxy-ethyl)-methyl-amino[-propyl, 3-[(2-methoxy-ethyl)-methyl-amino]-propyl, 3-[(2,3-Dihydroxy-propyl)-methyl-amino]-propyl, 3-(4-methyl-piperazine-1-yl)-propyl and 3-[(2-Diethylamino-ethyl)-methyl-amino]-propyl.

15. The compound of claim 4 wherein c=1;

A is phenyl;

B is

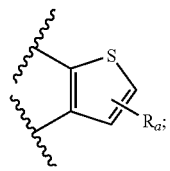

R is selected from the group consisting of $(CR^3R^4)_d N(R^2)_2$, $NR^2(CR^3R^4)_e N(R^2)_2$, $O(CR^3R^4)_e N(R^2)_2$ and $C(O)NR^2(CR^3R^4)_d N(R^2)_2$; and a is 1.

16. The compound of claim 4 wherein c=1,

A is phenyl;

B is

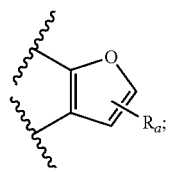

R is selected from the group consisting of $(CR^3R^4)_d N(R^2)_2$, $NR^2(CR^3R^4)_e N(R^2)_2$, $O(CR^3R^4)_e N(R^2)_2$ and $C(O)NR^2(CR^3R^4)_d N(R^2)_2$; and a is 1.

17. A method for treating a disease related to unregulated tyrosine kinase signal transduction, which comprises administering to a subject in need thereof, a pharmaceutically effective amount of at least one compound according to claim 1, or a pharmaceutically acceptable salt thereof; wherein the disease is selected from the group consisting of diabetic retinopathy, age-related macular degeneration, retinopathy of prematurity, arthritis, restenosis, hepatic cirrhosis, atherosclerosis, surgical adhesions, glomerulonephritis, diabetic nephropathy, malignant nephrosclerosis, thrombotic microangiopathy, transplant rejection, glomerulopathies, psoriasis, diabetes mellitus, wound healing, and inflammation.

18. A pharmaceutical composition comprising a pharmaceutically effective amount of at least one compound of claim 1, or a pharmaceutically acceptable salt thereof, and at least one pharmaceutically acceptable carrier.

19. A compound selected from the group consisting of:

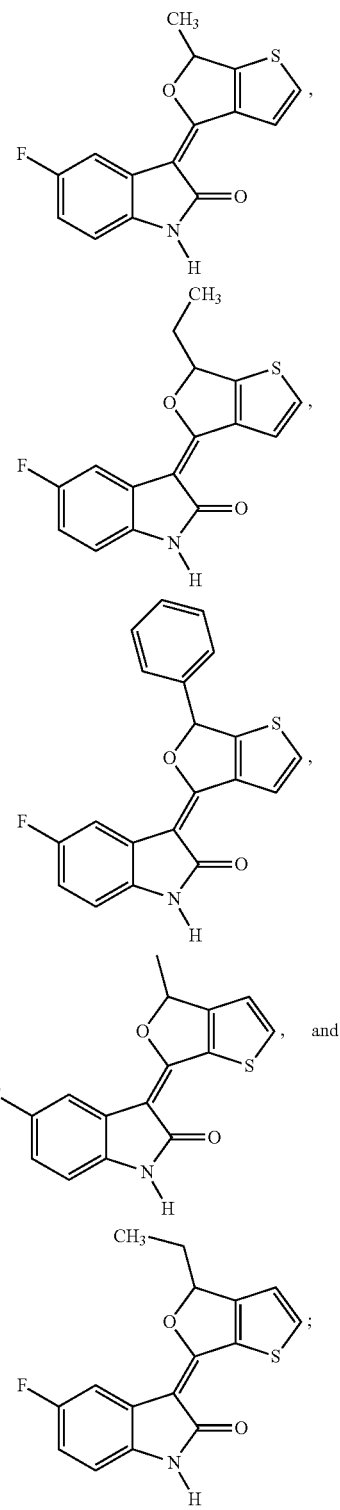

or a pharmaceutically acceptable salt thereof.

20. A pharmaceutical composition comprising a pharmaceutically effective amount of at least one compound of claim 19, or a pharmaceutically acceptable salt thereof, and at least one pharmaceutically acceptable carrier.

21. A method for treating a disease selected from the group consisting of diabetic retinopathy, age-related macular degeneration, retinopathy of prematurity, arthritis, restenosis, hepatic cirrhosis, atherosclerosis, surgical adhesions, glomerulonephritis, diabetic nephropathy, malignant nephrosclerosis, thrombotic microangiopathy, transplant rejection, glomerulopathies, psoriasis, diabetes mellitus, wound healing, and inflammation, which comprises administering to a subject in need thereof, a pharmaceutically effective amount at least one compound according to claim 19, or a pharmaceutically acceptable salt thereof.

\* \* \* \* \*